(12) United States Patent
Khairatkar-Joshi et al.

(10) Patent No.: US 9,186,360 B2
(45) Date of Patent: *Nov. 17, 2015

(54) TREATMENT OF RESPIRATORY DISORDERS USING TRPA1 ANTAGONISTS

(75) Inventors: Neelima Khairatkar-Joshi, Thane (IN); Abhay Kulkarni, Navi Mumbai (IN); Indranil Mukhopadhyay, Navi Mumbai (IN); Vidya Ganapati Kattige, Thane (IN); Vikram Mansingh Bhosale, Mumbai (IN); Dinesh Pradeep Wale, Osmanabad (IN); Abraham Thomas, Navi Mumbai (IN); Sukeerthi Kumar, Navi Mumbai (IN); Sachin Sundarlal Chaudhari, Navi Mumbai (IN)

(73) Assignee: GLENMARK PHARMACEUTICALS S.A., La Chaux-de-Fonds (CH)

(*) Notice: Subject to any disclaimer, the term of this patent is extended or adjusted under 35 U.S.C. 154(b) by 528 days.

This patent is subject to a terminal disclaimer.

(21) Appl. No.: 13/495,271

(22) Filed: Jun. 13, 2012

(65) Prior Publication Data

US 2012/0316136 A1  Dec. 13, 2012

Related U.S. Application Data

(60) Provisional application No. 61/498,740, filed on Jun. 20, 2011.

(30) Foreign Application Priority Data

Jun. 13, 2011  (IN) .......................... 1722/MUM/2011
Mar. 9, 2012  (IN) ............................ 635/MUM/2012

(51) Int. Cl.
| A61K 31/519 | (2006.01) |
| A61K 31/517 | (2006.01) |
| A61K 31/15 | (2006.01) |
| A61K 31/675 | (2006.01) |
| A61K 31/522 | (2006.01) |

(52) U.S. Cl.
CPC ................ A61K 31/522 (2013.01); A61K 31/15 (2013.01); A61K 31/517 (2013.01); A61K 31/519 (2013.01); A61K 31/675 (2013.01)

(58) Field of Classification Search
CPC ... A61K 31/522; A61K 31/15; A61K 31/675; A61K 31/517; A61K 31/519

USPC ............... 514/81, 267, 266.2, 266.23, 265.1, 514/262.1, 260.1, 264.1, 640, 263.2
See application file for complete search history.

(56) References Cited

U.S. PATENT DOCUMENTS

| 7,671,061 | B2 * | 3/2010 | Moran et al. ............. 514/263.35 |
| 8,507,503 | B2 * | 8/2013 | Kumar et al. ............. 514/260.1 |
| 2011/0124666 | A1 | 5/2011 | Gijsen et al. | |
| 2011/0144137 | A1 | 6/2011 | Jordt et al. | |
| 2012/0046305 | A1 | 2/2012 | Moran et al. | |

FOREIGN PATENT DOCUMENTS

| WO | 2004/055054 A1 | 7/2004 |
| WO | 2005/089206 A2 | 9/2005 |
| WO | 2007/073505 A2 | 6/2007 |
| WO | 2008/094909 A2 | 8/2008 |
| WO | 2009/002933 A1 | 12/2008 |
| WO | 2009/089082 A1 | 7/2009 |
| WO | 2009/140517 A1 | 11/2009 |
| WO | 2009/144548 A1 | 12/2009 |
| WO | 2009/158719 A2 | 12/2009 |
| WO | 2010/004390 A1 | 1/2010 |
| WO | 2010/109239 A1 | 9/2010 |
| WO | 2010/109287 A1 | 9/2010 |
| WO | 2010/109328 A1 | 9/2010 |
| WO | 2010/109334 A2 | 9/2010 |
| WO | 2010/125469 A1 | 11/2010 |
| WO | 2010/132838 A1 | 11/2010 |
| WO | 2011/114184 A1 | 9/2011 |
| WO | 2011/132017 A1 | 10/2011 |
| WO | 2012/050641 A2 | 4/2012 |

OTHER PUBLICATIONS

International Search Report dated Sep. 19, 2012, for corresponding International Patent Application No. PCT/IB2012/052942.
Written Opinion dated Sep. 19, 2012, for corresponding International Patent Application No. PCT/IB2012/052942.
International Preliminary Report on Patentability issued Dec. 17, 2013, for corresponding International Patent Application No. PCT/IB2012/052942.

* cited by examiner

*Primary Examiner* — Jennifer M Kim
(74) *Attorney, Agent, or Firm* — Pergament Gilman & Cepeda LLP; Milagros A. Cepeda; Edward D. Pergament

(57) ABSTRACT

The present patent application relates to treatment of a respiratory disorder using TRPA1 antagonists. Particularly, the present patent application relates to treatment of a respiratory disorder using a TRPA1 antagonist, wherein the TRPA1 antagonist is administered by inhalation route to a subject in need thereof.

7 Claims, 5 Drawing Sheets

TREATMENT OF RESPIRATORY DISORDERS USING TRPA1 ANTAGONISTS

PRIORITY DOCUMENTS

This patent application claims priority to Indian Provisional Patent Application numbers 1722/MUM/2011 (filed on Jun. 13, 2011) and 635/MUM/2012 (filed on Mar. 9, 2012), and Unites States Provisional Patent Application No. 61/498,740 (filed on Jun. 20, 2011), the contents of each of which are incorporated by reference herein.

TECHNICAL FIELD

The present patent application relates to treatment of a respiratory disorder using transient receptor potential ankyrin-1 receptor ("TRPA1") antagonists. Particularly, the present patent application relates to treatment of a respiratory disorder using a TRPA1 antagonist, wherein the TRPA1 antagonist is administered by inhalation route to a subject in need thereof.

BACKGROUND

Transient Receptor Potential (TRP) ion channels or receptors constitute a superfamily of cation channels that consists of 28 members with a wide range of physiological functions. TRP receptors have been classified into seven subfamilies viz., TRPC (canonical), TRPV (vanilloid), TRPM (melastatin), TRPP (polycystin), TRPML (mucolipin), TRPA (ankyrin) and TRPN(NOMPC) families.

TRPA1, also known as ANKTM1, is a large transmembrane protein of 1119 amino acids in human with six predicted membrane-spanning domains and a single pore loop characteristic of all other TRP receptor proteins. TRPA1 possesses a long N-terminal region with up to 18 predicted ankyrin repeats. TRPA1 is believed to be most closely related to TRPV3, and is more closely related to TRPV1 and TRPV2 than to TRPV5 and TRPV6.

It is believed TRPA1 is expressed in nociceptive neurons, which sense the peripheral damage and transmit pain signals and on C fibers in the bronchopulmonary region. TRPA1 is membrane bound, and most likely acts as a heterodimeric voltage gated channel. TRPA1 plays a variety of pathophysiological roles as a sensor of irritating chemicals and cold, and is a participant in both airway inflammation and airway hyper-responsiveness.

The TRPA1 receptor activation in the airways by noxious stimuli, including cold temperatures (generally, less than about 17° C.), pungent natural compounds (e.g., mustard, cinnamon and garlic), tobacco smoke, tear gas and environmental irritants, is supposed to be one of the mechanisms for neurogenic inflammation in the airways. Neurogenic inflammation is an important component of chronic airway diseases like chronic obstructive pulmonary disease ("COPD") and asthma.

Activation of TRPA1 receptor by its agonists is reported to cause pain, neuropeptide release, and neurogenic inflammation and airway sensory responses. Signaling events downstream of TRPA1 activation include intracellular $Ca^{+2}$ modulation, release of inflammatory cytokines and neuropeptide release, in general plasma extravasation, bronchoconstriction, and respiratory depression during respiratory disease condition in particular. TRPA1 antagonists would abrogate the TRPA1 receptor mediated downstream signaling events. TRPA1 receptor blockade is perceived as a novel strategy for therapeutic intervention of pain and respiratory disorders.

Respiratory disorders related to airway inflammation include a number of severe lung diseases including asthma and COPD. The airways of asthmatic patients are infiltrated by inflammatory leukocytes, of which the eosinophil is believed to be the most prominent component. Inflammatory sensitization of airway neurons is believed to increase nasal sensitivity, heighten the sense of irritation, and promote fluid secretion, airway narrowing, and bronchoconstriction.

Oxidative stress is a hallmark of most acute and chronic inflammatory airway conditions, including viral infections, asthma, rhinitis, and COPD. TRPA1-activating stimuli such as cigarette smoke, chlorine, aldehydes, and scents are among the most prevalent triggers of asthma as well as COPD. Endogenous TRPA1 agonists, including reactive oxygen species (ROS) and lipid peroxidation products, are potent drivers of allergen-induced airway inflammation in asthma. During inflammation, ROS are generated by infiltrating macrophages and neutrophils.

PCT Application Publication Nos. WO 2004/055054, WO 2005/089206, WO 2007/073505, WO 2008/0949099, WO 2009/089082, WO 2009/002933, WO 2009/158719, WO 2010/109334, WO 2009/144548, WO 2010/004390, WO 2010/109287, WO 2010/109329, WO 2010/109328, WO 2010/125469 and WO 2011/114184 describe various transient receptor potential ("TRP") receptor modulators.

SUMMARY

The present invention relates to treatment of a respiratory disorder using a TRPA1 antagonist, wherein the TRPA1 antagonist is administered by inhalation route to a subject in need thereof.

The inventors of the present invention have surprisingly found that the TRPA1 antagonists, which have high potency (e.g., $IC_{50}$ for inhibiting human TRPA1 receptor activity of less than 2 micromolar) combined with marked selectivity in the TRPA1 receptor over other types of TRP receptors, are effective in the treatment of respiratory disorders when administered to a subject by an inhalation route (e.g., by mouth and/or intranasal administration).

Thus, in an embodiment, the present invention relates to a method of reducing eosinophil or neutrophil count in a subject having a respiratory disorder, said method comprising administering to the subject by inhalation route an effective amount of a TRPA1 antagonist, wherein the TRPA1 antagonist which has an $IC_{50}$ for inhibiting human TRPA1 receptor activity of less than 2 micromolar, thereby reducing said eosinophil or neutrophil count in said subject. In an aspect, the method further comprises increasing the measurement of forced expiratory volume in 1 sec (FEV1) of said subject.

In a preferred embodiment, the TRPA1 antagonist has an $IC_{50}$ for inhibiting human TRPA1 receptor activity of less than 1 micromolar, or less than 700 nanomolar or more preferably, less than 500 nanomolar.

In a preferred embodiment, the respiratory disorder includes airway inflammation, asthma, rhinitis, cough, bronchitis, or COPD. More preferably, the respiratory disorder is asthma or COPD.

Particularly contemplated in one embodiment, is the administration of TRPA1 antagonists which has high potency (e.g., $IC_{50}$ for inhibiting human TRPA1 receptor activity of less than 2 micromolar) combined with marked selectivity in the TRPA1 receptor over other types of TRP receptors, via an inhalation route for treatment of asthma or COPD, both of which are separately contemplated.

In a preferred embodiment, the present invention relates to a method of treating asthma or COPD in a subject, said method comprising administering to the subject by inhalation route an effective amount of a TRPA1 antagonist which has an IC$_{50}$ for inhibiting human TRPA1 receptor activity of less than 2 micromolar or less than 1 micromolar or preferably less than 700 nanomolar or 500 nanomolar.

In another embodiment, the present invention relates to a method of treating a respiratory disorder (such as asthma or COPD) by reducing the eosinophil or neutrophil count and/or airway hyper-reactivity/responsiveness in a subject, said method comprising administering to the subject by inhalation route an effective amount of a TRPA1 antagonist which has an IC$_{50}$ for inhibiting human TRPA1 receptor activity of less than 2 micromolar, or less than 1 micromolar, or preferably less than 700 nanomolar or more preferably less than 500 nanomolar.

In yet another embodiment, the present invention relates to a method of reducing eosinophil or neutrophil count and/or increasing FEV1 in a subject having a respiratory disorder (such as asthma or COPD), said method comprising administering to the subject by inhalation route an effective amount of a TRPA1 antagonist has an IC$_{50}$ for inhibiting human TRPV1, TRPV3, TRPV4 and TRPM8 receptor activity greater than at least 10 times the IC$_{50}$ for inhibiting human TRPA1 receptor activity. Preferably, the TRPA1 antagonist has an IC$_{50}$ for inhibiting human TRPV1, TRPV3, TRPV4 and TRPM8 receptor activity greater than at least 100 times the IC$_{50}$ for inhibiting human TRPA1 receptor activity. In an aspect, the TRPA1 antagonist is a selective TRPA1 antagonist. In an aspect, TRPA1 antagonist useful in the context of the invention, is selected from one of the following formulae: (A) or (B) or (C) or (D)

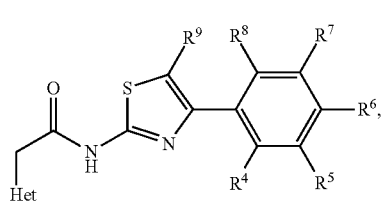
(A)

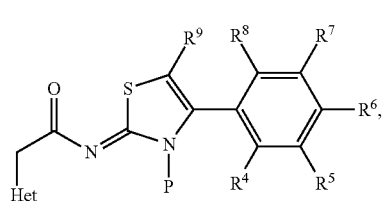
(B)

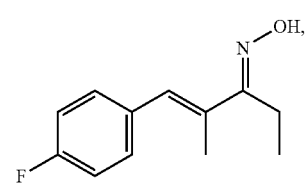
(C)

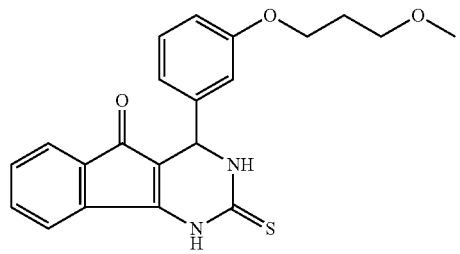
(D)

or a pharmaceutically-acceptable salt thereof, wherein, 'Het' is selected from the group consisting of

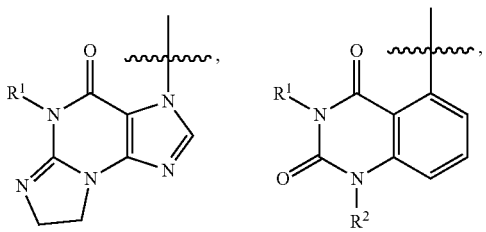

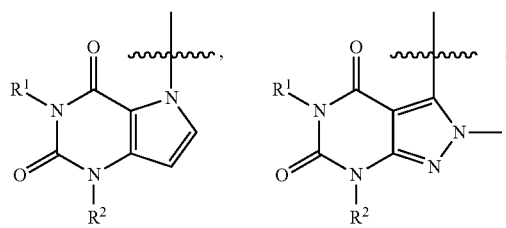

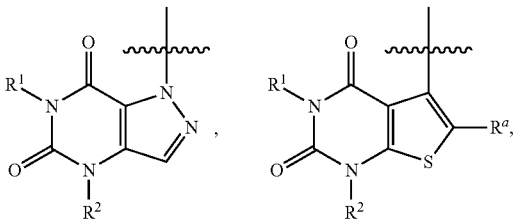

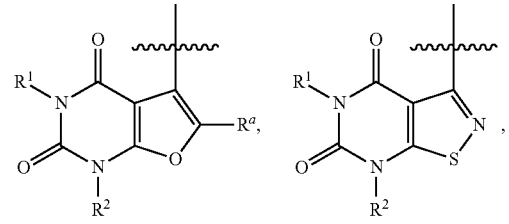

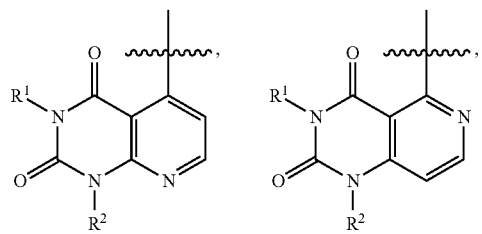

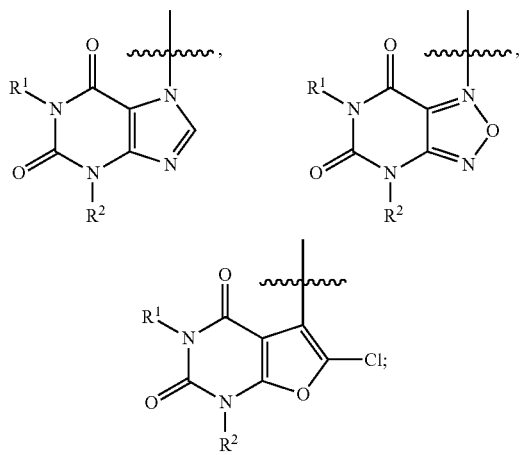

P is selected from

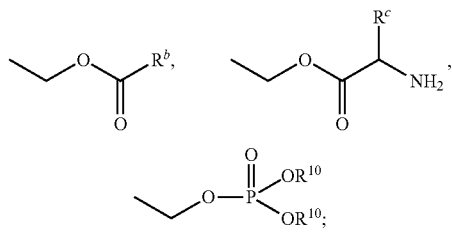

R¹, R² and Rᵃ, which may be the same or different, are each independently hydrogen or (C₁-C₄)alkyl;

Rᵇ and Rᶜ independently selected from hydrogen, substituted or unsubstituted alkyl arylalkyl, amino acid and heterocyclic ring;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

R¹⁰ is selected from hydrogen, alkyl, arylalkyl and pharmaceutically acceptable cation.

In an embodiment, the present invention relates to a method of reducing eosinophil or neutrophil count and/or increasing FEV1 in a subject having a respiratory disorder, said method comprising administering to the subject by inhalation route an effective amount of a TRPA1 antagonist of formulae: (XII) or (D)

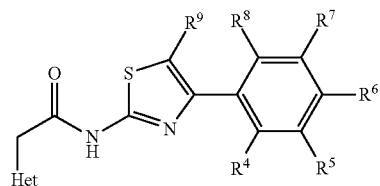

(XII)

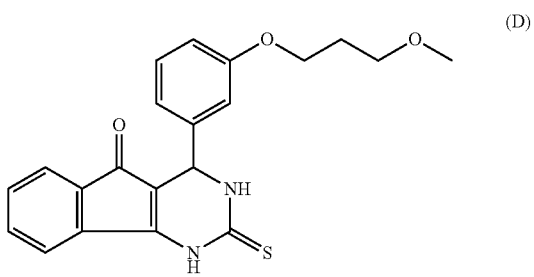

(D)

or a pharmaceutically-acceptable salt thereof, wherein, 'Het' is selected from the group consisting of

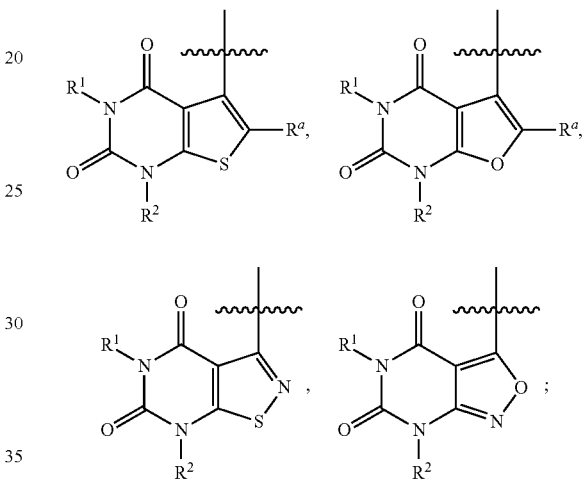

R¹, R² and Rᵃ, which may be the same or different, are each independently hydrogen or (C₁-C₄)alkyl;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

In an embodiment, the present invention relates to a method of reducing eosinophil or neutrophil count and/or increasing FEV1 in a subject having a respiratory disorder, said method comprising administering to the subject by inhalation route an effective amount of a TRPA1 antagonist is (Compound 52)

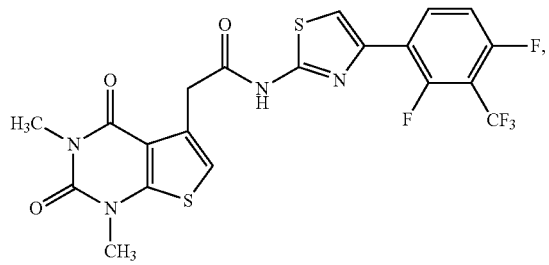

-continued

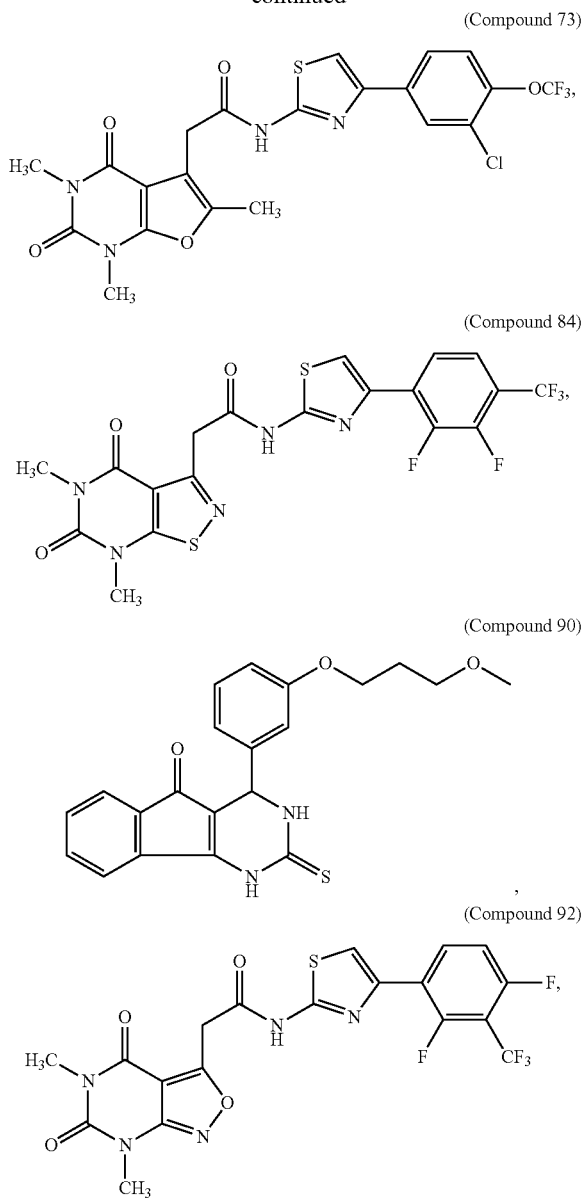

(Compound 73)

(Compound 84)

(Compound 90)

(Compound 92)

or a pharmaceutically acceptable salt thereof.

In the context of present invention, the inhalation route comprises intranasal or oral inhalation or both, particularly wherein the TRPA1 antagonist is administered to nose, lungs or pulmonary region of the subject.

The present invention also provides a pharmaceutical composition for inhalation administration comprising a TRPA1 antagonist which has an $IC_{50}$ for inhibiting human TRPA1 receptor activity of less than 2 micromolar, or less than 1 micromolar, or preferably less than 700 nanomolar, or more preferably less than 500 nanomolar. The pharmaceutical compositions suitable for administration by inhalation route typically include dry powder inhaler (DPI) formulations, metered dose inhaler (MDI) formulations, nasal sprays, insufflations, and formulations suitable for nebulization.

In another embodiment, the present invention relates to a method of reducing eosinophil or neutrophil count and/or increasing FEV1 in a subject having a respiratory disorder, said method comprising administering to the subject by inhalation route an effective amount of a TRPA1 antagonist which has an $IC_{50}$ for inhibiting human TRPA1 receptor activity of less than 2 micromolar. It is specifically contemplated that the inhibition of human TRPA1 receptor activity is the principal, but not the exclusive, therapeutic mode of action of the TRPA1 antagonist.

As contemplated herein, the TRPA1 antagonist of the present invention exhibits marked selectivity (e.g., at least 10 fold) for inhibition of human TRPA1 receptor activity over the inhibitory action of the same compound or biological molecule in the other TRP receptor family members. Specifically contemplated is a TRPA1 antagonist that exhibits selectivity of at least 10 fold for inhibition of human TRPA1 receptor activity over the inhibitory action of the same compound or biological molecule in human TRPV1, TRPV3, TRPV4 and TRPM8 receptors, each separately contemplated.

Specifically contemplated is a method of treating respiratory disease (such as asthma or COPD) by reducing eosinophil or neutrophil count and/or increasing FEV1 comprising administering a TRPA1 antagonist that exhibits selectivity of at least 10 fold for inhibition of human TRPA1 receptor activity over the inhibitory action of the same compound or biological molecule in human TRPV1, TRPV3, TRPV4 and TRPM8 receptors, each separately contemplated.

In an embodiment, the present invention relates to a method of treating a respiratory disorder (such as asthma or COPD) by reducing eosinophil or neutrophil count and/or increasing FEV1 in a subject, said method comprising administering to the subject by inhalation route an effective amount of a TRPA1 antagonist which has an $IC_{50}$ for inhibiting human TRPA1 receptor activity of less than 2 micromolar or less than 1 micromolar, or preferably less than 700 nanomolar or even more preferably less than 500 nanomolar, and wherein the TRPA1 antagonist has an $IC_{50}$ for inhibiting human TRPV1 receptor activity greater than at least 10 times the $IC_{50}$ for inhibiting human TRPA1 receptor activity. Preferably, the TRPA1 antagonist has an $IC_{50}$ for inhibiting human TRPV1 receptor activity greater than at least 100 times the $IC_{50}$ for inhibiting human TRPA1 receptor activity.

In another embodiment, the present invention relates to a method of treating a respiratory disorder (such as asthma or COPD) by reducing eosinophil or neutrophil count and/or increasing FEV1 in a subject, said method comprising administering to the subject by inhalation route an effective amount of a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar, and wherein the TRPA1 antagonist has an $IC_{50}$ for inhibiting human TRPV3 receptor activity greater than at least 10 times the $IC_{50}$ for inhibiting human TRPA1 receptor activity. Preferably, the TRPA1 antagonist has an $IC_{50}$ for inhibiting human TRPV3 receptor activity greater than at least 100 times the $IC_{50}$ for inhibiting human TRPA1 receptor activity.

In yet another embodiment, the present invention relates to a method of treating a respiratory disorder, such as asthma or COPD by reducing eosinophil or neutrophil count and/or increasing FEV1, in a subject, said method comprising administering to the subject by inhalation route an effective amount of a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar, and wherein the TRPA1 antagonist has an $IC_{50}$ for inhibiting human TRPV4 receptor activity greater than at least 10 times the $IC_{50}$ for inhibiting human TRPA1 receptor activity. Preferably, the TRPA1 antagonist has an $IC_{50}$ for inhibiting human TRPV4 receptor activity greater than at least 100 times the $IC_{50}$ for inhibiting human TRPA1 receptor activity.

In a further embodiment, the present invention relates to a method of treating a respiratory disorder, such as asthma or COPD by reducing eosinophil or neutrophil count and/or increasing FEV1, in a subject, said method comprising administering to the subject by inhalation route an effective amount of a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar, and wherein the TRPA1 antagonist has an $IC_{50}$ for inhibiting human TRPM8 receptor activity greater than at least 10 times the $IC_{50}$ for inhibiting human TRPA1 receptor activity. Preferably, the TRPA1 antagonist has an $IC_{50}$ for inhibiting human TRPM8 receptor activity greater than at least 100 times the $IC_{50}$ for inhibiting human TRPA1 receptor activity.

In an embodiment, the present invention relates to a method of treating a respiratory disorder in a subject by reducing eosinophil or neutrophil count and/or increasing FEV1, said method comprising administering to the subject by nasal or oral inhalation route an effective amount of a TRPA1 antagonist which has an $IC_{50}$ for inhibiting human TRPA1 receptor activity of less than 2 micromolar or less than 1 micromolar, wherein such inhibition of human TRPA1 receptor activity is the principal therapeutic mode of action of the TRPA1 antagonist, and wherein,
  (a) the TRPA1 antagonist has an $IC_{50}$ for inhibiting human TRPV1 receptor activity greater than at least 10 times the $IC_{50}$ for inhibiting human TRPA1 receptor activity; and/or
  (b) the TRPA1 antagonist has an $IC_{50}$ for inhibiting human TRPV3 receptor activity greater than at least 10 times the $IC_{50}$ for inhibiting human TRPA1 receptor activity; and/or
  (c) the TRPA1 antagonist has an $IC_{50}$ for inhibiting human TRPV4 receptor activity greater than at least 10 times the $IC_{50}$ for inhibiting human TRPA1 receptor activity; and/or
  (d) the TRPA1 antagonist has an $IC_{50}$ for inhibiting human TRPM8 receptor activity greater than at least 10 times the $IC_{50}$ for inhibiting human TRPA1 receptor activity.

In an aspect, the TRPA1 antagonist is a selective TRPA1 antagonist.

The present invention also relates to a method of identifying a TRPA1 antagonist useful for treating a respiratory disorder by inhalation administration in a subject, said method comprising:
  (a) determining an $IC_{50}$ for inhibiting human TRPA1 receptor activity of each of the plurality of compounds;
  (b) selecting the compounds which has an $IC_{50}$ for inhibiting human TRPA1 receptor activity of less than 2 micromolar;
  (c) determining $IC_{50}$ of such compounds for inhibiting human TRPV1, TRPV3, TRPV4 and/or TRPM8 receptor activities;
  (d) identifying such compounds which have the $IC_{50}$ for inhibiting human TRPV1, TRPV3, TRPV4 and/or TRPM8 receptor activities greater than at least 10 times the $IC_{50}$ for inhibiting human TRPA1 receptor activity;
  (e) evaluating the in vivo activity of the identified compounds in a respiratory disorder model, wherein the compounds are administered by inhalation route; and
  (f) identifying the compounds to be effective for treating the respiratory disorder.

In an embodiment, the present invention relates to a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar for the treatment of a respiratory disorder, such as asthma or COPD by reducing eosinophil or neutrophil count and/or increasing FEV1, in a subject, wherein an effective amount of the TRPA1 antagonist is administered to the subject by inhalation route, and wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to a TRPA1 antagonist which has an $IC_{50}$ for inhibiting human TRPA1 receptor activity of less than 2 micromolar, or less than 1 micromolar or preferably less than 700 nanomolar, or more preferably less than 500 nanomolar for the treatment of a respiratory disorder, such as asthma or COPD by reducing eosinophil or neutrophil count and/or increasing FEV1, in a subject, wherein an effective amount of the TRPA1 antagonist is administered to the subject by inhalation route, and wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar for the treatment of a respiratory disorder, such as asthma or COPD by reducing eosinophil or neutrophil count and/or increasing FEV1, in a subject, wherein an effective amount of the TRPA1 antagonist is administered to the subject by inhalation route, and wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar for the treatment of a respiratory disorder, such as asthma or COPD by reducing eosinophil or neutrophil count and/or increasing FEV1, in a subject, wherein an effective amount of the TRPA1 antagonist is administered to the subject by inhalation route, and wherein the TRPA1 antagonist has an $IC_{50}$ for inhibiting human TRPM8 receptor activity greater than at least 10 times the $IC_{50}$ for inhibiting human TRPA1 receptor activity.

The present invention, in an embodiment, also provides use of an effective amount of a TRPA1 antagonist which has an $IC_{50}$ for inhibiting human TRPA1 receptor activity of less than 2 micromolar in the manufacture of a composition for inhalation administration for reducing eosinophil or neutrophil count and/or increasing FEV1 in the treatment of a respiratory disorder in a subject. Preferably, the TRPA1 antagonist has an $IC_{50}$ for inhibiting human TRPA1 receptor activity of less than 1 micromolar or less than 700 nanomolar, or more preferably, less than 500 nanomolar.

In another embodiment, the present invention provides use of an effective amount of a TRPA1 antagonist which has an $IC_{50}$ for inhibiting human TRPA1 receptor activity of less than 2 micromolar in the manufacture of a composition for inhalation administration for reducing eosinophil or neutrophil count and/or increasing FEV1 in the treatment of a respiratory disorder in a subject, wherein such inhibition of human TRPA1 receptor activity is the principal therapeutic mode of action of the TRPA1 antagonist.

In an aspect, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another aspect, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another aspect, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further aspect, the present invention relates to use of an effective amount of a TRPA1 antagonist which has an $IC_{50}$ for inhibiting human TRPA1 receptor activity of less than less than 2 micromolar or less than 1 micromolar or preferably less than 700 nanomolar, or more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

The present invention, in an embodiment, also provides use of an effective amount of a TRPA1 antagonist of formulae: (A) or (B) or (C) or (D)

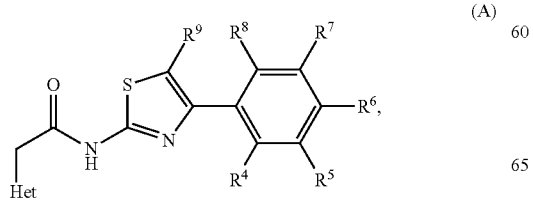

(A)

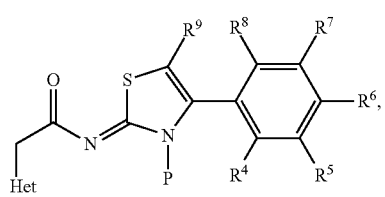

(B)

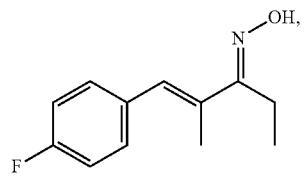

(C)

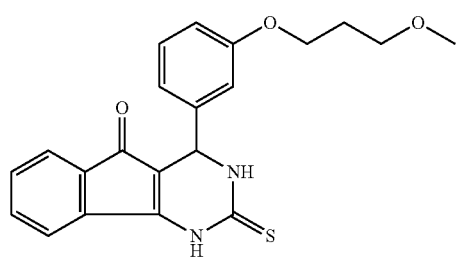

(D)

or a pharmaceutically-acceptable salt thereof, wherein, 'Het' is selected from the group consisting of

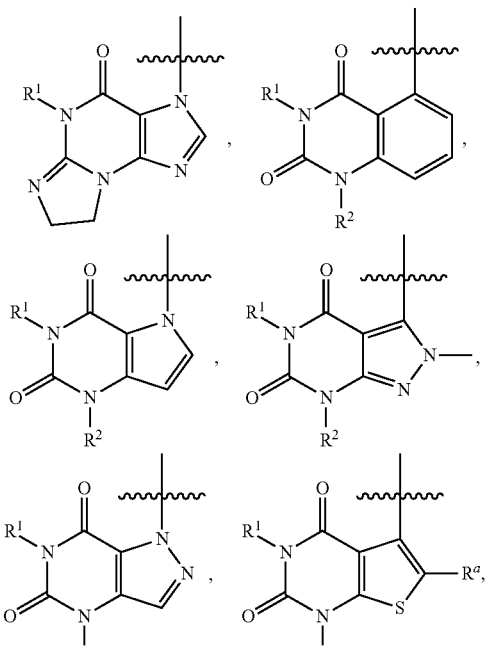

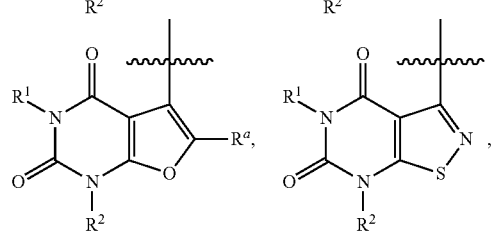

-continued

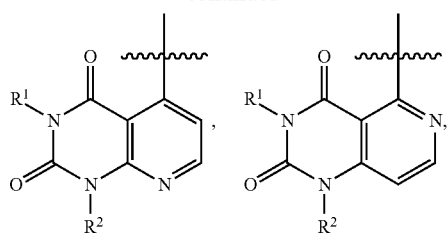

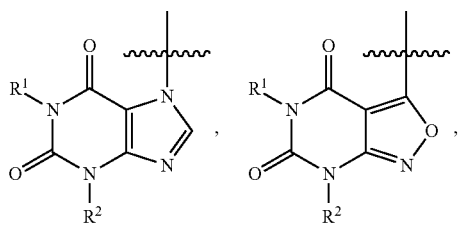

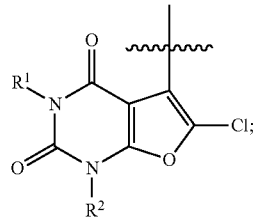

P is selected from

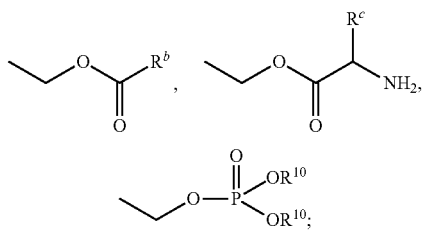

R¹, R² and Rᵃ, which may be the same or different, are each independently hydrogen or (C₁-C₄)alkyl;

Rᵇ and Rᶜ independently selected from hydrogen, substituted or unsubstituted alkyl arylalkyl, amino acid and heterocyclic ring;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

R¹⁰ is selected from hydrogen, alkyl, arylalkyl and pharmaceutically acceptable cation, in the manufacture of a composition for inhalation administration for reducing eosinophil or neutrophil count and/or increasing FEV1 in the treatment of a respiratory disorder in a subject.

The present invention, in an embodiment, also provides use of an effective amount of a TRPA1 antagonist of formulae: (XII) or (D)

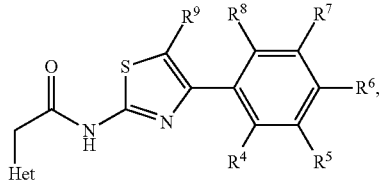

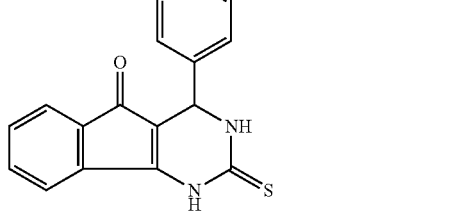

or a pharmaceutically-acceptable salt thereof, wherein, 'Het' is selected from the group consisting of

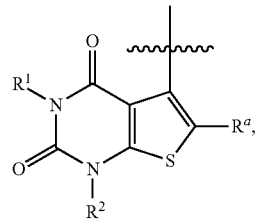 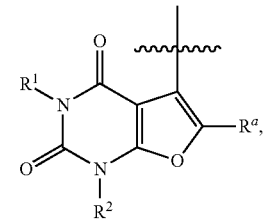

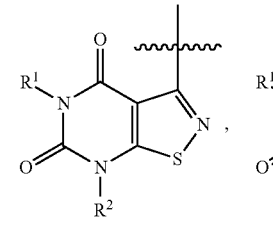 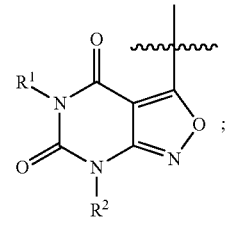

R¹, R² and Rᵃ, which may be the same or different, are each independently hydrogen or (C₁-C₄)alkyl;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl, in the manufacture of a composition for inhalation administration for reducing eosinophil or neutrophil count and/or increasing FEV1 in the treatment of a respiratory disorder in a subject.

The present invention, in an embodiment, also provides use of an effective amount of a TRPA1 antagonist, which is

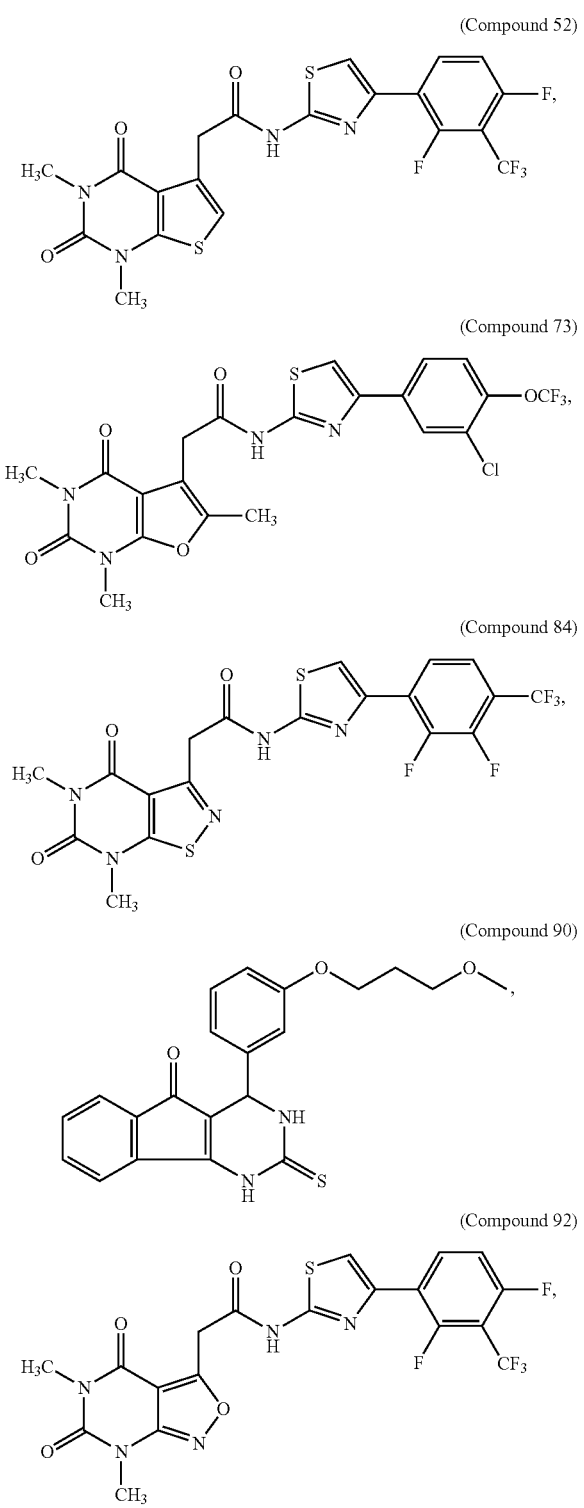

(Compound 52)
(Compound 73)
(Compound 84)
(Compound 90)
(Compound 92)

or a pharmaceutically acceptable salt thereof, in the manufacture of a composition for inhalation administration for reducing eosinophil or neutrophil count and/or increasing FEV1 in the treatment of a respiratory disorder in a subject.

In another embodiment, the present invention provides a TRPA1 antagonist which has an $IC_{50}$ for inhibiting human TRPA1 receptor activity of less than 2 micromolar or less than 1 micromolar, or less than 700 nanomolar, for reducing eosinophil or neutrophil count and/or increasing FEV1 in the treatment of a respiratory disorder in a subject, wherein an effective amount of the TRPA1 antagonist is administered to the subject by inhalation route.

In another embodiment, the present invention provides a method of treating a respiratory disorder by reducing eosinophil or neutrophil count and increasing FEV1 in a subject, said method comprising administering a TRPA1 antagonist that has an $IC_{50}$ for inhibiting human TRPV1, TRPV3, TRPV4 and TRPM8 receptor activity greater than at least 10 times the $IC_{50}$ for inhibiting human TRPA1 receptor activity.

In another embodiment, the present invention provides a pharmaceutical composition for inhalation administration comprising a TRPA1 antagonist that has an $IC_{50}$ for inhibiting human TRPA1 receptor activity of less than 2 micromolar for reducing eosinophil or neutrophil count in a subject having a respiratory disorder.

DETAILED DESCRIPTION

Definitions

Figure 1:
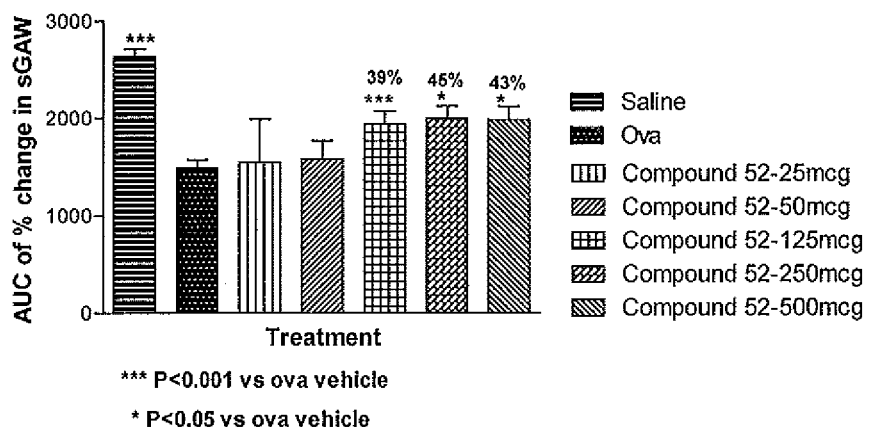
FIG. 1 is a bar graph that represents the effect of Compound 52 on AUC for specific airway conductance in ovalbumin induced asthma model in guinea pigs.

The terms used herein are defined as follows. If a definition set forth in the present application and a definition set forth earlier in a provisional application from which priority is claimed are in conflict, the definition in the present application shall control the meaning of the terms.

The term "effective amount" or "therapeutically effective amount" denotes an amount of the TRPA1 antagonist that, when administered to a subject by inhalation route for treating a respiratory disorder mediated by TRPA1 modulation, is sufficient to produce medically significant therapeutic benefit in a subject. The term "medically significant" denotes an amount sufficient to provide at least a minimal medical benefit in the subject. The effective amount of the TRPA1 antagonist as described herein ranges from 0.01 mcg to 50 mg, or preferably, from 0.05 mcg to 40 mg to be administered by inhalation route to the subject; although larger or smaller amount is not excluded if they fall within the scope of the definition of this paragraph. In an embodiment, the effective amount of TRPA1 antagonist to be administered per day may range from about 1 mcg to about 20 mg, and preferably from about 10 mcg to about 10 mg.

Specifically, the effective amount of Compound 52 or its pharmaceutically acceptable salt may range from about 0.1 mcg to about 40 mg and preferably from about 1 mcg to about 30 mg The effective amount of Compound 73 or its pharmaceutically acceptable salt may range from about 0.1 mcg to about 40 mg and preferably from about 1 mcg to about 30 mg. The effective amount of Compound 84 or its pharmaceutically acceptable salt may range from about 0.1 mcg to about 40 mg and preferably from about 1 mcg to about 30 mg. The effective amount of Compound 90 or its pharmaceutically acceptable salt may range from about 0.1 mcg to about 40 mg and preferably from about 1 mcg to about 30 mg. The effective amount of Compound 92 or its pharmaceutically acceptable salt may range from about 0.1 mcg to about 40 mg and preferably from about 1 mcg to about 30 mg.

The term "compound" (used interchangeably with "agent" or "inhibitor" or "antagonist") includes both chemical molecules, for example, small organic molecules and biological molecules, for example, protein antibodies.

The term "treating" or "treatment" as used herein also covers the prophylaxis, mitigation, maintenance, prevention, amelioration, or suppression of a respiratory disorder modulated by the TRPA1 antagonist in a subject.

By the term "respiratory disorder", it is meant any condition or disease related to respiration or the respiratory system and includes but is not limited to airway inflammation, asthma, emphysema, bronchitis, COPD, sinusitis, rhinitis, cough, bronchospasm, airflow obstruction, exercise-induced bronchospasm, exacerbations, bronchoconstriction, respiratory depression, reactive airways dysfunction syndrome (RADS), acute respiratory distress syndrome (ARDS), irritant induced asthma, occupational asthma, sensory hyperreactivity, multiple chemical sensitivity, and aid in smoking cessation therapy. Preferably, the respiratory disorder is airway inflammation, asthma, emphysema, rhinitis (e.g., allergic rhinitis and associated symptoms), cough, bronchitis, and COPD. More preferably, the respiratory disorder is asthma or COPD.

The term "$IC_{50}$" refers to molar concentration of a compound that is needed to inhibit a given biological process by half.

The term "subject" includes mammals like humans and other animals, such as domestic animals (e.g., household pets including cats and dogs) and non-domestic animals (such as wildlife). Preferably, the subject is a human.

By "pharmaceutically acceptable excipient", it is meant any of the components of a pharmaceutical combination other than the actives and which are approved by regulatory authorities or are generally regarded as safe for human or animal use.

The term "inhalation" in the present context encompasses administration by inhalation route including oral and nasal inhalation route.

The term "composition for inhalation" in the present context includes formulations meant to be administered as dry powder inhalation, metered dose inhalation, nebulization, nasal spray, or insufflation. Preferably, the composition for inhalation is a dry powder inhalation or a metered dose inhalation product.

The term "FEV1" in the present context refers to an amount of air which can be forcibly exhaled from the lungs in the first second of a forced exhalation by a subject. Because asthma causes the air in lungs to be exhaled at a slower rate and in smaller amounts compared to a normal, healthy person, measuring how well the patient can forcibly exhale air can help determine the presence of asthma.

The term "selective TRPA1 antagonist" as used herein refers to a TRPA1 antagonist, which has an $IC_{50}$ for inhibiting human TRPV1, TRPV3, TRPV4 and TRPM8 receptor activity greater than at least 10 times the $IC_{50}$ for inhibiting human TRPA1 receptor activity. Preferably, the TRPA1 antagonist has an $IC_{50}$ for inhibiting human TRPV1, TRPV3, TRPV4 and TRPM8 receptor activity greater than at least 100 times the $IC_{50}$ for inhibiting human TRPA1 receptor activity. Thus, the selective TRPA1 antagonist as contemplated herein is at least 10 fold (or preferably at least 100 fold) selective over TRPV1, TRPV3, TRPV4 and TRPM8 receptors.

Compounds

The compounds useful in the methods and compositions of the present invention include the TRPA1 antagonists that may be administered by an inhalation route (e.g., nasal or oral inhalation or both) to a subject. Accordingly, the exemplary TRPA1 antagonists that are useful for inhalation administration in the present invention are given below. The compounds mentioned below defined under various formulae are few representative compounds, and by no means limit the scope of the invention to only these compounds.

In an embodiment, TRPA1 antagonist useful in the context of the invention, is selected from one of the following formulae: (A) or (B) or (C) or (D)

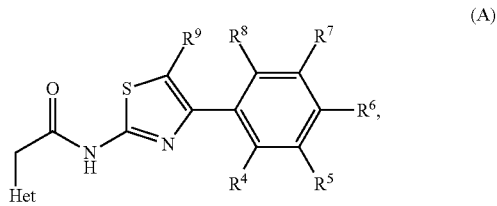

(A)

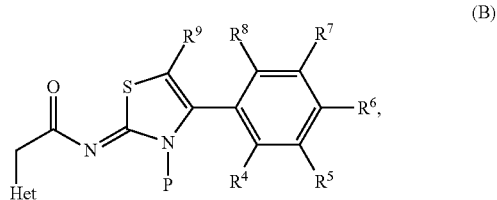

(B)

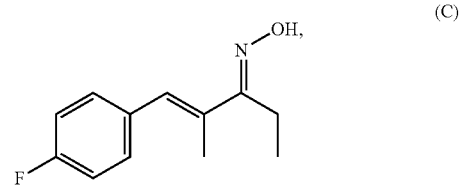

(C)

-continued

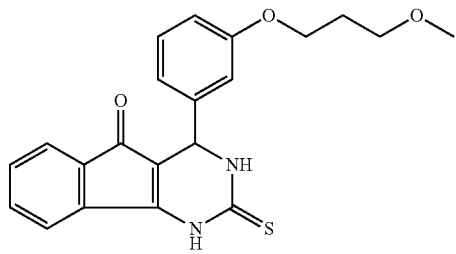

or a pharmaceutically-acceptable salt thereof, wherein, 'Het' is selected from the group consisting of

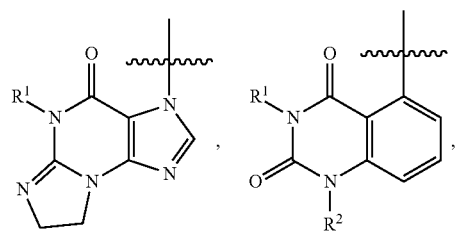

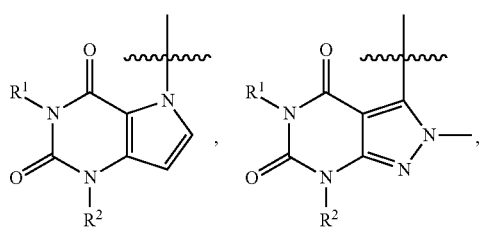

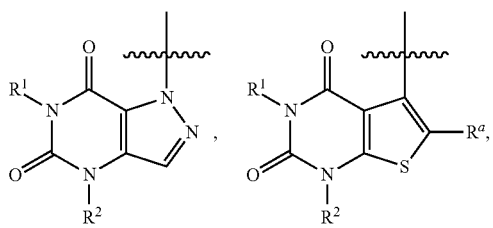

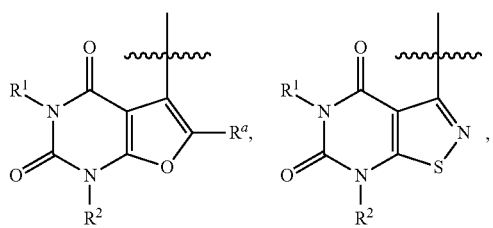

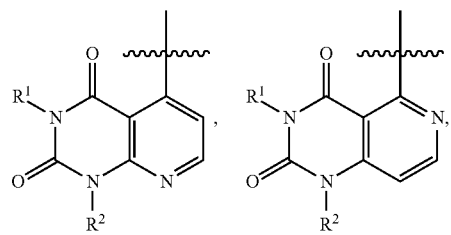

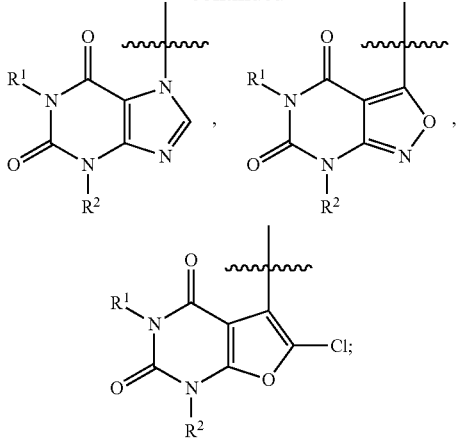

P is selected from

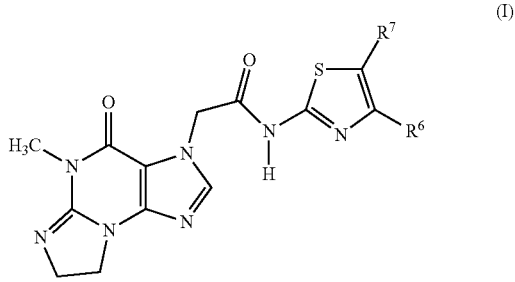

$R^1$, $R^2$ and $R^a$, which may be the same or different, are each independently hydrogen or $(C_1\text{-}C_4)$alkyl;

$R^b$ and $R^c$ independently selected from hydrogen, substituted or unsubstituted alkyl arylalkyl, amino acid and heterocyclic ring;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

$R^{10}$ is selected from hydrogen, alkyl, arylalkyl and pharmaceutically acceptable cation.

In one embodiment, TRPA1 antagonists useful in the context of the invention are selected from those compounds generically or specifically disclosed in WO2009144548. Accordingly, a TRPA1 antagonist useful in the context of the invention has the formula (I):

or a pharmaceutically acceptable salt thereof,
wherein,

R$^6$ represents hydrogen, substituted or unsubstituted alkyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl;

R$^7$ independently represents hydrogen or alkyl.

Few representative TRPA1 antagonists useful in the methods of the invention are mentioned below:

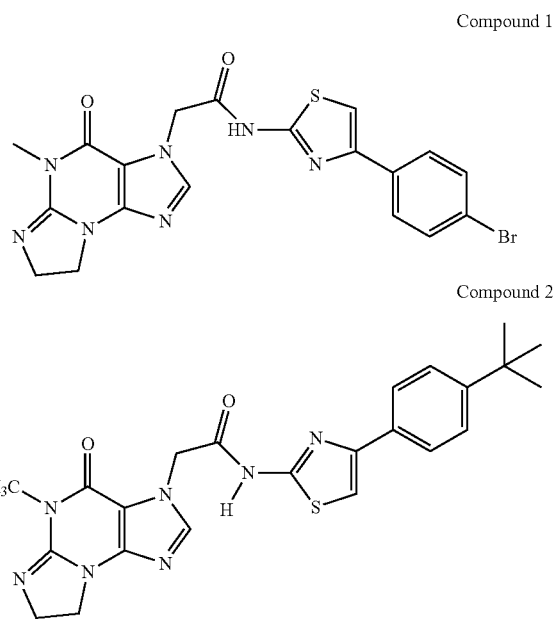

Compound 1

Compound 2

The preparation of above said compounds is described in WO2009144548.

In another embodiment, TRPA1 antagonists useful in the context of the invention are selected from those compounds generically or specifically disclosed in WO2010004390. Accordingly, TRPA1 antagonist useful in the context of the invention has the formula (II):

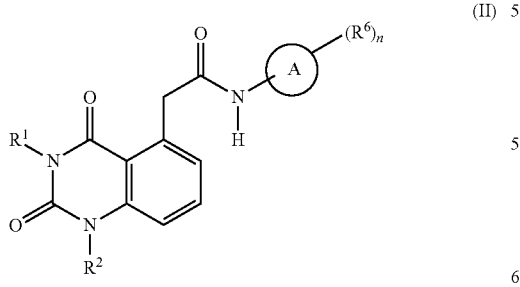

(II)

or pharmaceutically acceptable salts thereof,
wherein,
at each occurrence W and R$^2$ is independently selected from hydrogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, (CR$^x$R$^y$)$_n$OR$^x$, COR$^x$, COOR$^x$, CONR$^x$R$^y$, SO$_2$NR$^x$R$^y$, NR$^x$R$^y$, NR$^x$(CR$^x$R$^y$)$_n$OR$^x$, NR$^x$(CR$^x$R$^y$)$_n$CN(CH$_2$)$_n$NR$^x$R$^y$, (CH$_2$)$_n$CHR$^x$R$^y$, (CR$^x$R$^y$)NR$^x$R$^y$, NR$^x$(CR$^x$R$^y$)$_n$CONR$^x$R$^y$, (CH$_2$)$_n$NHCOR$^x$ and (CH$_2$)$_n$NH(CH$_2$)$_n$SO$_2$R$^x$, (CH$_2$)$_n$NHSO$_2$R$^x$;

R$^x$ and R$^y$ are independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl;

R$^x$ and R$^y$ may be joined together to form an optionally substituted 3 to 7 membered saturated, unsaturated or partially saturated cyclic ring, which may optionally include at least two heteroatoms selected from O, NR$^a$ or S;

ring A is selected from phenyl, pyridinyl, pyrazolyl, thiazolyl and thiadiazolyl; each occurrence of R$^6$ is independently hydrogen, cyano, nitro, —NR$^x$R$^y$, halogen, hydroxyl, haloalkyl, haloalkoxy, cycloalkylalkoxy, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, R$^x$ and R$^y$ are independently selected from hydrogen, hydroxyl, halogen, substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, and substituted or unsubstituted heteroarylalkyl;

at each occurrence of 'n' is independently selected from 1 to 5.

According to one embodiment, specifically provided are compounds of the formula (IIa)

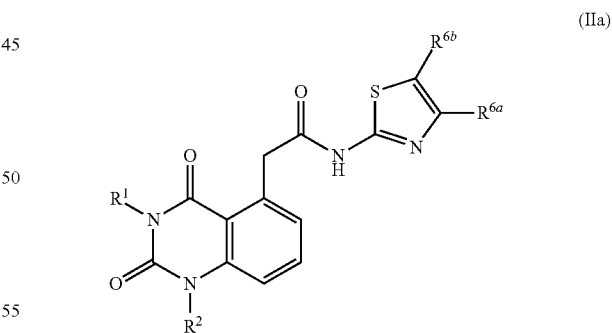

(IIa)

or pharmaceutically acceptable salts thereof,
wherein,

R$^1$ and R$^2$ are as defined above for the compound of formula (II);

R$^{6a}$ and R$^{6b}$ are independently selected from hydrogen, cyano, nitro, —NR$^x$R$^y$, halogen, hydroxyl, haloalkyl, haloalkoxy, cycloalkylalkoxy, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, —C(O)OR$^x$, —OR$^x$, —C(O)NR$^x$R$^y$, —C(O)R$^x$, —SO$_2$R$^x$, —SO$_2$—NR$^x$R$^y$.

Few representative TRPA1 antagonists useful in the context of the invention are mentioned below:

Compound 3
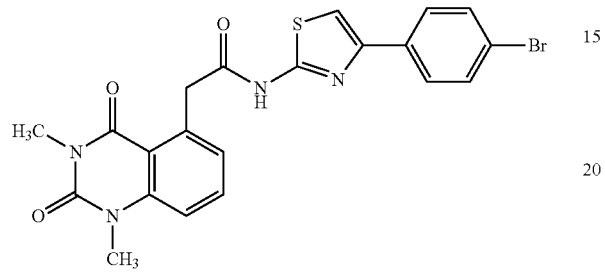

Compound 4
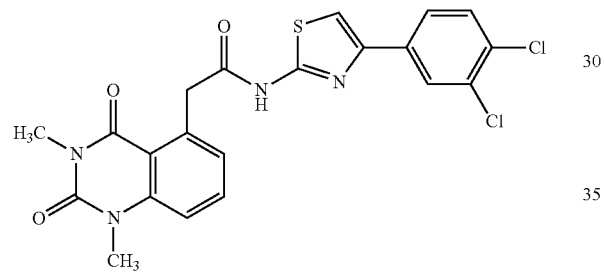

Compound 5
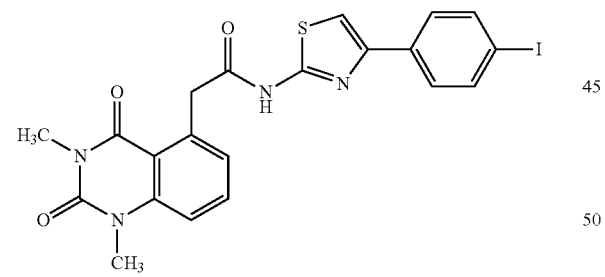

Compound 6
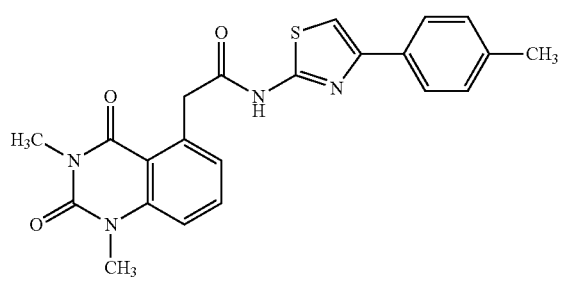

-continued

Compound 7
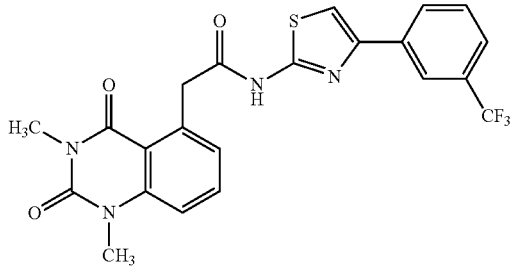

Compound 8
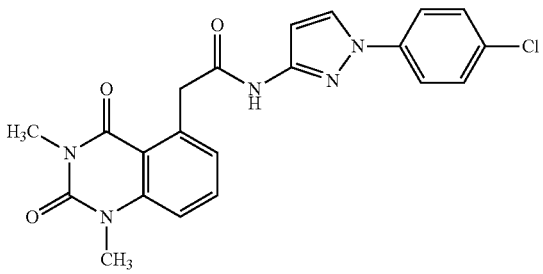

Compound 9
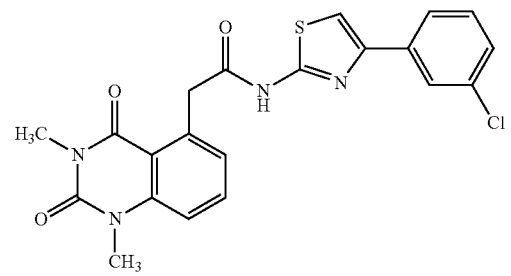

Compound 10
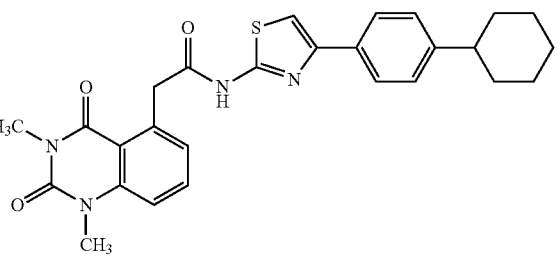

Compound 11
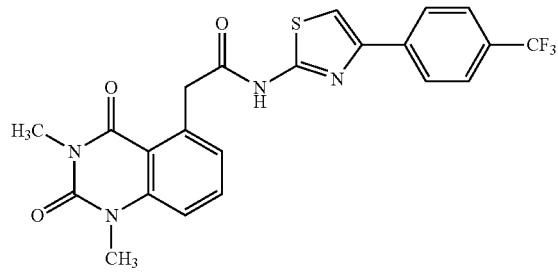

Compound 12
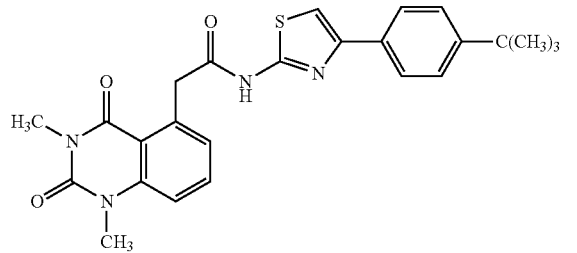
Compound 17
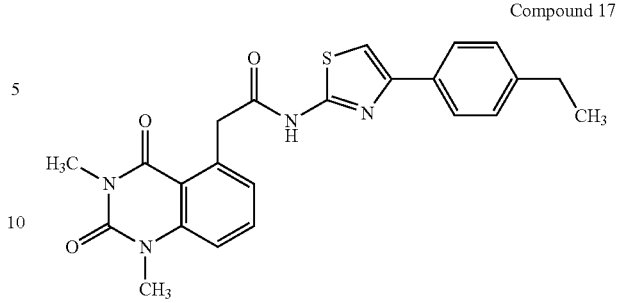
Compound 13
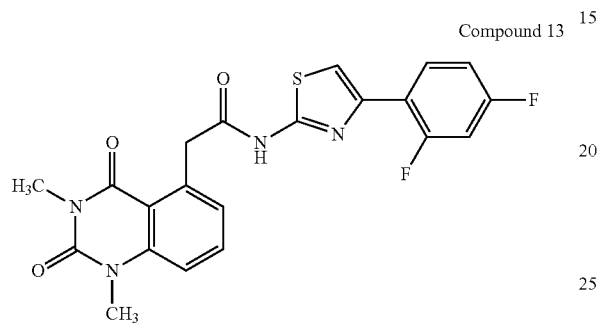
Compound 18
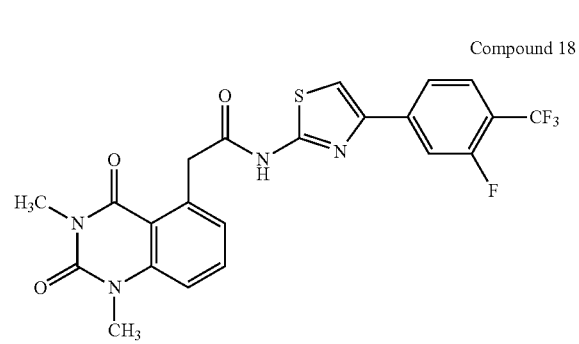
Compound 14
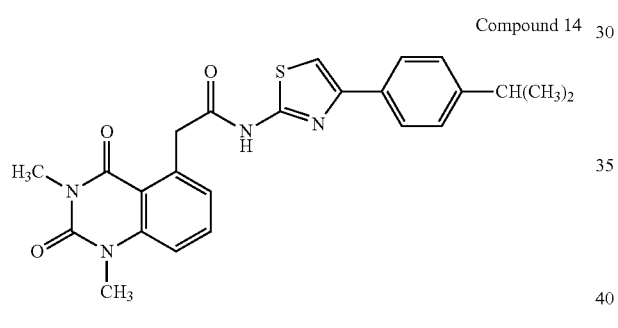
Compound 19
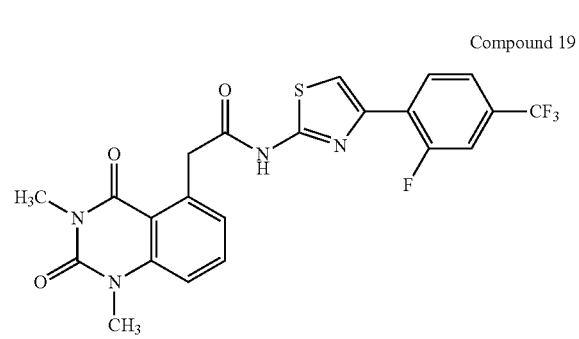
Compound 15
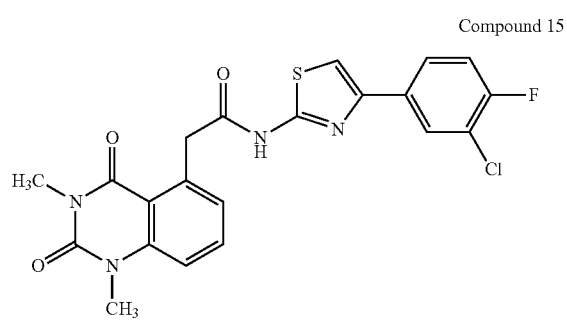
Compound 20
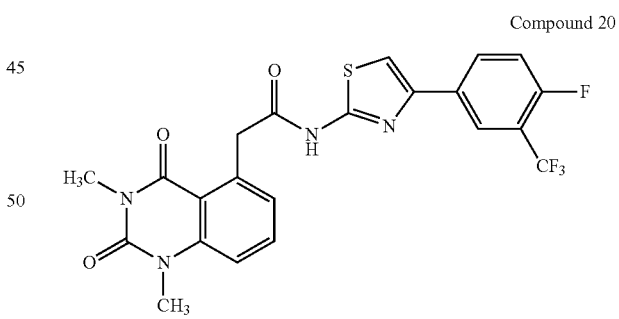
Compound 16
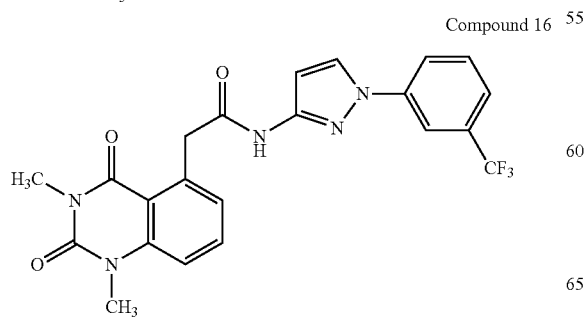
Compound 21
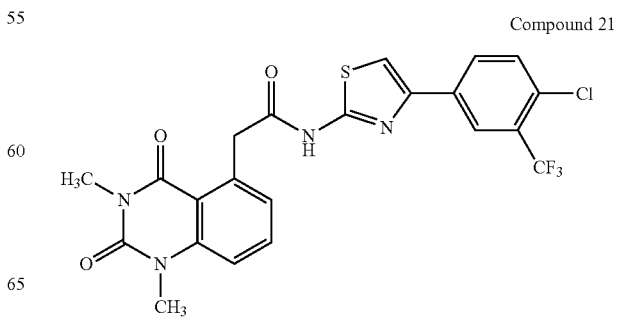

Compound 22
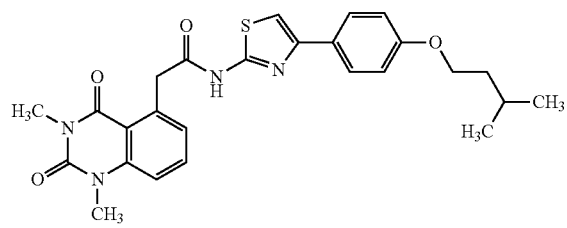
Compound 23
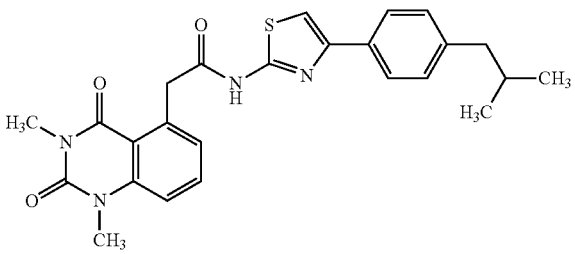
Compound 24
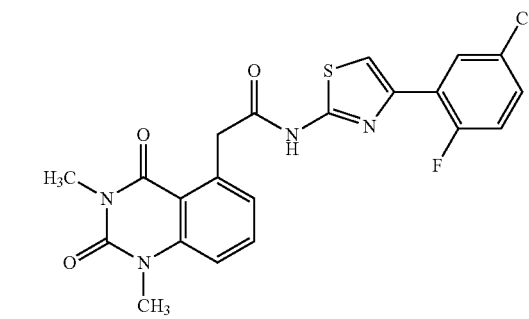
Compound 25
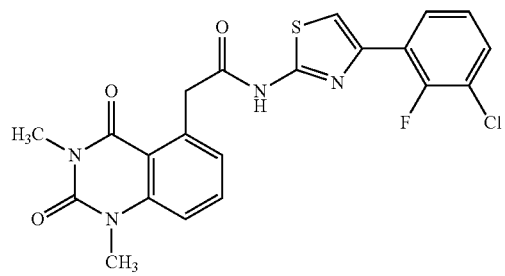
Compound 26
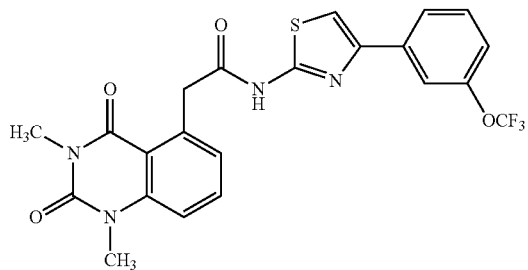
Compound 27
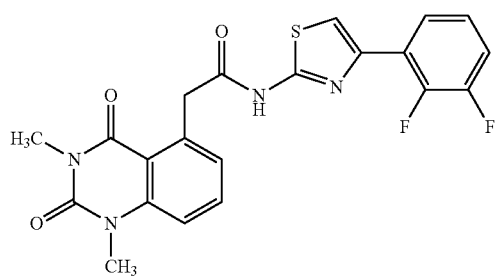
Compound 28
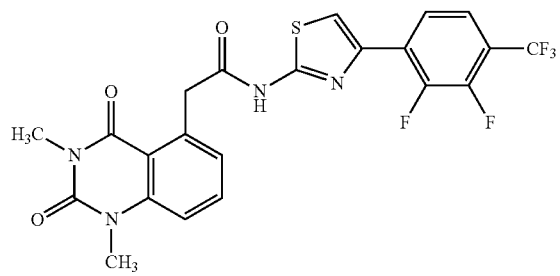
Compound 29
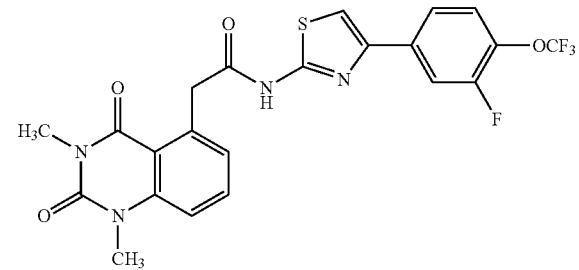
Compound 30
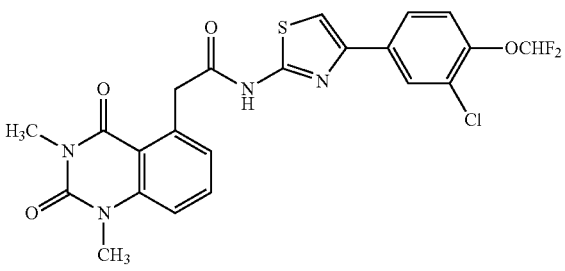
Compound 31
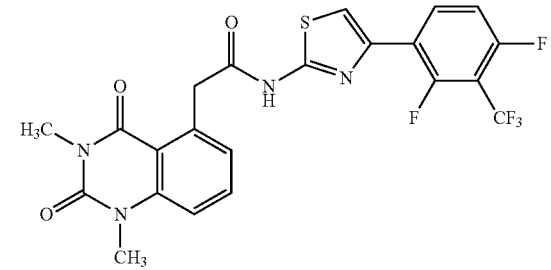

Compound 32

[Chemical structure of Compound 32]

Compound 33

[Chemical structure of Compound 33]

The preparation of above said compounds is described in WO2010004390.

In one embodiment, TRPA1 antagonists useful in the context of the invention are selected from those compounds generically or specifically disclosed in WO2010109287. Accordingly, TRPA1 antagonist useful in the context of the invention has the formula (III):

[Chemical structure of Formula (III)]

or a pharmaceutically acceptable salt thereof, wherein, $Z_1$ is $NR^a$ or $CR^a$;
$Z_2$ is $NR^b$ or $CR^b$;
$Z_3$ is N or C;
with the proviso that when $Z_2$ is $CR^b$ then both $Z_1$ and $Z_3$ are not nitrogen at the same time;

at each occurrence, $R^a$ and $R^b$ which may be same or different, are independently selected from hydrogen, hydroxyl, cyano, halogen, substituted or unsubstituted alkyl, haloalkyl, alkenyl, alkynyl, cycloalkyl, cycloalkylalkyl, —$(CR^xR^y)_nOR^x$, —$COR^x$, —$COOR^x$, —$CONR^xR^y$, —$S(O)_mNR^xR^y$, —$NR^xR^y$, —$NR^x(CR^xR^y)_nOR^x$, —$(CH_2)_nNR^xR^y$, —$(CH_2)_nCHR^xR^y$, —$(CH_2)NR^xR^y$, —$NR^x(CR^xR^y)_nCONR^xR^y$, —$(CH_2)_nNHCOR^x$, —$(CH_2)_nNH(CH_2)_nSO_2R^x$ and $(CH_2)_nNHSO_2R^x$; alternatively either of $R^a$ or $R^b$ is absent;

$R^1$ and $R^2$, which may be same or different, are independently selected from hydrogen, hydroxyl, substituted or unsubstituted alkyl, haloalkyl, alkenyl, alkynyl, cycloalkyl, cycloalkylalkyl, arylalkyl, $(CR^xR^y)_nOR^x$, $COR^x$, $COOR^x$, $CONR^xR^y$, $(CH_2)_nNR^xR^y$, $(CH_2)_nCHR^xR^y$, $(CH_2)NR^xR^y$ and $(CH_2)_nNHCOR^x$;

$R^3$ is selected from hydrogen, substituted or unsubstituted alkyl, alkenyl, haloalkyl, alkynyl, cycloalkyl, cycloalkylalkyl, cycloalkenyl;

L is a linker selected from —$(CR^xR^y)_n$—, —O—$(CR^xR^y)_n$—, —C(O)—, —$NR^x$—, —$S(O)_mNR^x$—, —$NR^x(CR^xR^y)_n$— and —$S(O)_mNR^x(CR^xR^y)_n$;

U is selected from substituted or unsubstituted aryl, substituted or unsubstituted five membered heterocycles selected from the group consisting of thiazole, isothiazole, oxazole, isoxazole, thiadiazole, oxadiazole, pyrazole, imidazole, furan, thiophene, pyroles, 1,2,3-triazoles and 1,2,4-triazole; and substituted or unsubstituted six membered heterocycles selected from the group consisting of pyrimidine, pyridine and pyridazine;

V is selected from hydrogen, cyano, nitro, —$NR^xR^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —$C(O)OR^x$, —$OR^x$, —$C(O)NR^xR^y$, —$C(O)R^x$ and —$SO_2NR^xR^y$; or U and V together may form an optionally substituted 3 to 7 membered saturated or unsaturated cyclic ring, that may optionally include one or more heteroatoms selected from O, S and N;

at each occurrence, $R^x$ and $R^y$ are independently selected from the group consisting of hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl; and at each occurrence 'm' and 'n' are independently selected from 0 to 2, both inclusive.

Few representative TRPA1 antagonists useful in the context of the invention are mentioned below:

Compound 34

[Chemical structure of Compound 34]

Compound 35

[Chemical structure of Compound 35]

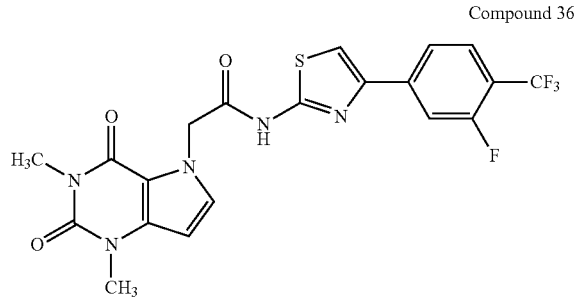
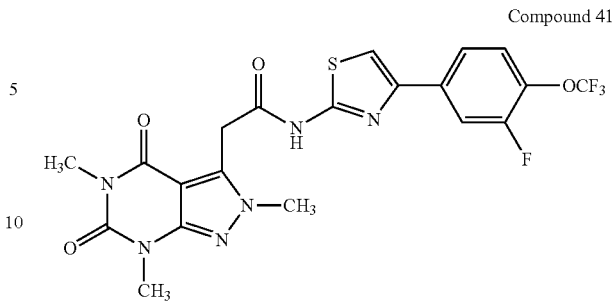
The preparation of above said compounds is described in WO2010109287.
In one embodiment, TRPA1 antagonists useful in the context of the invention are selected from those compounds generically or specifically disclosed in WO 2010109334. Accordingly, TRPA1 antagonists useful in the context of the invention has the formula (IV)

(IV)

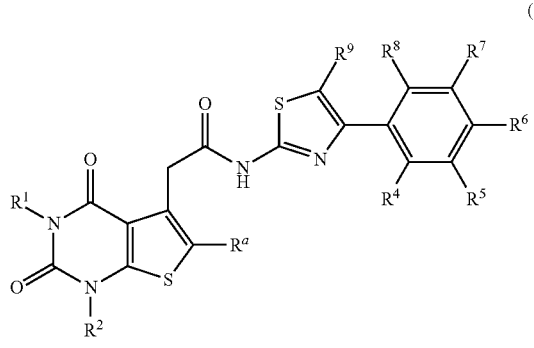

or a pharmaceutically-acceptable salt thereof
wherein, $R^1$, $R^2$ and $R^a$, which may be the same or different, are each independently hydrogen or $(C_1-C_4)$alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

Few representative TRPA1 antagonists useful in the context of the invention are mentioned below:

Compound 46

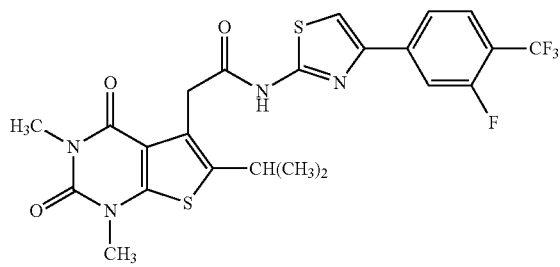

Compound 47

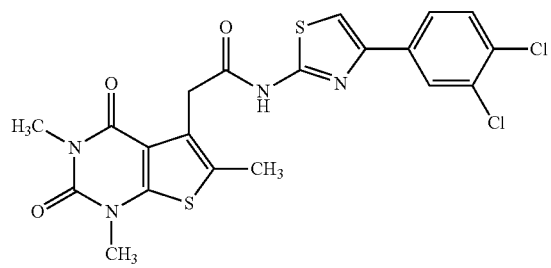

Compound 48

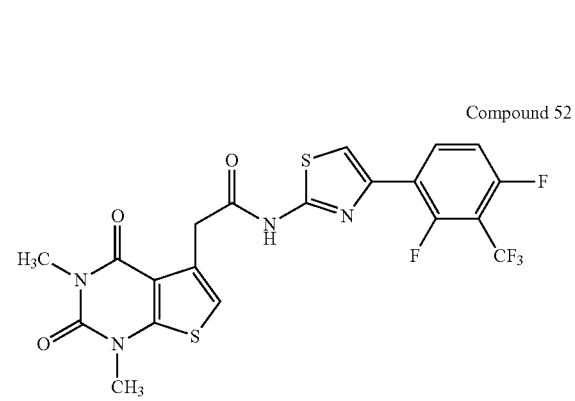

Compound 49

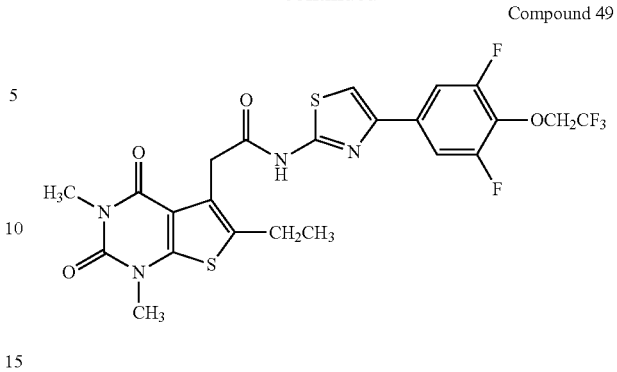

Compound 50

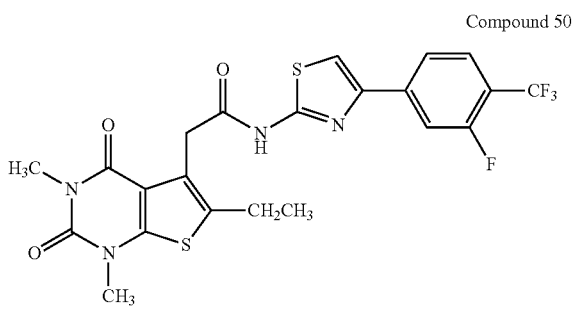

Compound 51

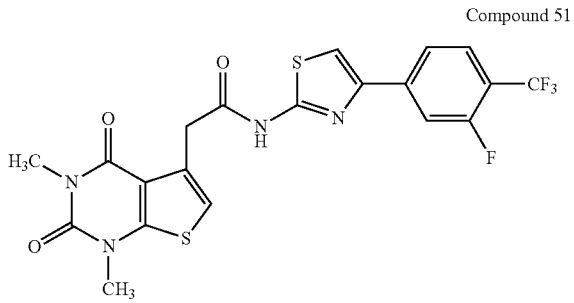

Compound 52

The preparation of above said compounds is described in WO2010109334.

In one embodiment, TRPA1 antagonists useful in the context of the invention are selected from those compounds generically or specifically disclosed in WO2010109329. Accordingly, TRPA1 antagonists useful in the context of the invention has the formula (V)

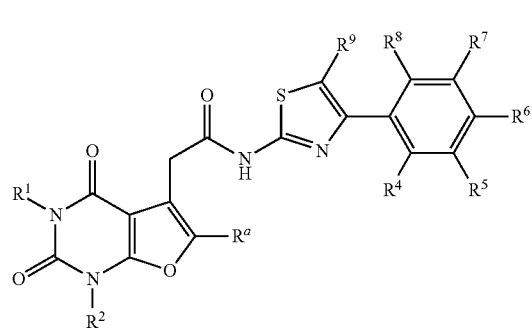

(V)

or a pharmaceutically acceptable salt thereof,
wherein,
R$^1$, R$^2$ and R$^a$ which may be the same or different, are each independently hydrogen or (C$_1$-C$_4$) alkyl; and
R$^4$, R$^5$, R$^6$, R$^7$, R$^8$ and R$^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

Few representative TRPA1 antagonists useful in the context of the invention are mentioned below:

Compound 53

Compound 54

Compound 55

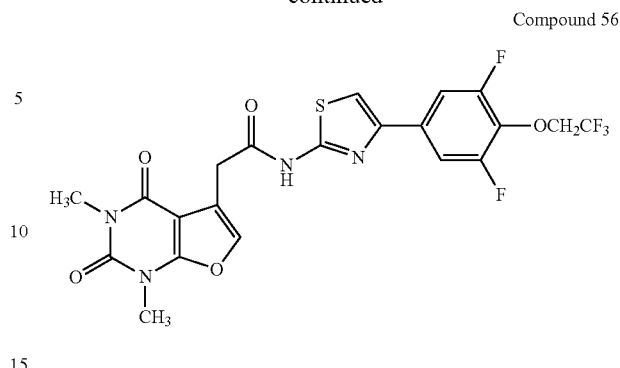

Compound 56

Compound 57

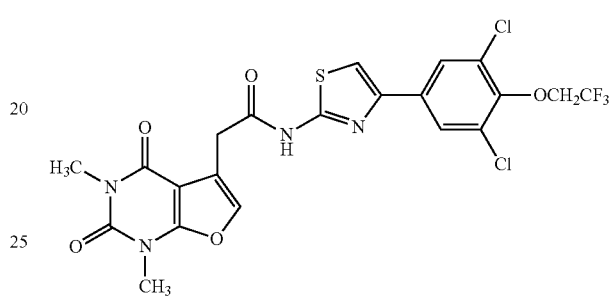

Compound 58

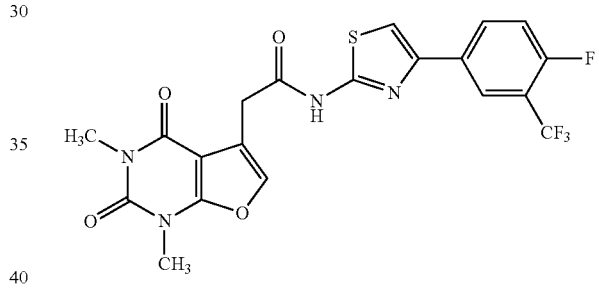

Compound 59

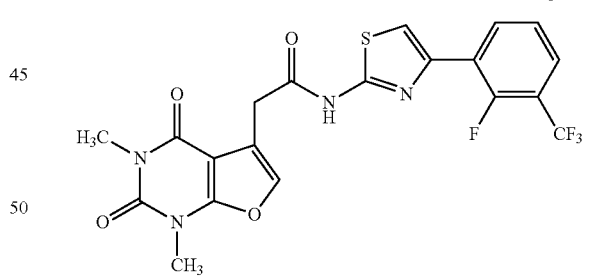

Compound 60

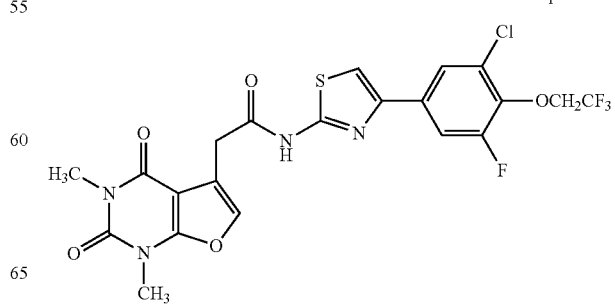

Compound 61
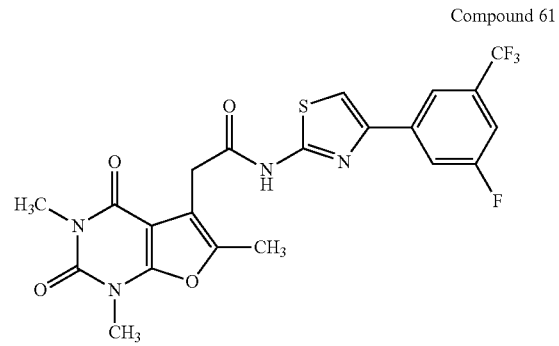
Compound 62
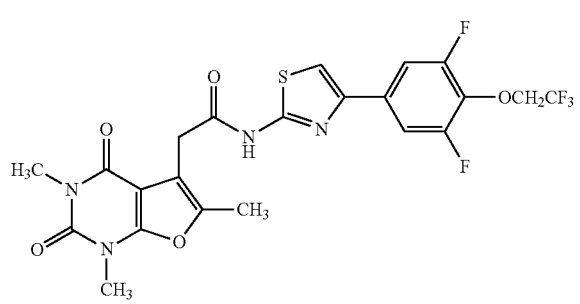
Compound 63
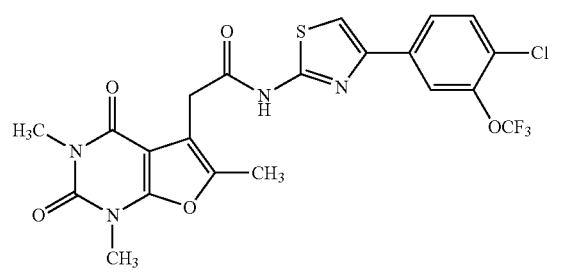
Compound 64
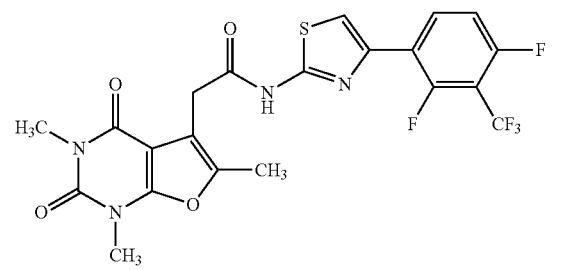
Compound 65
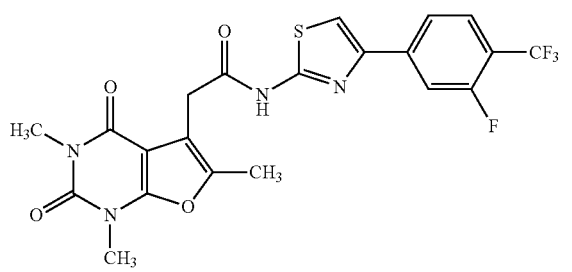
Compound 66
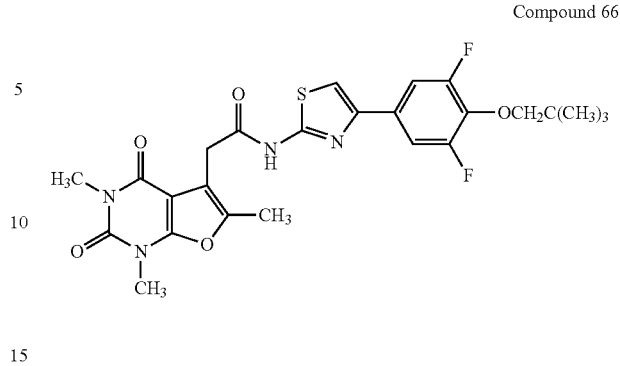
Compound 67
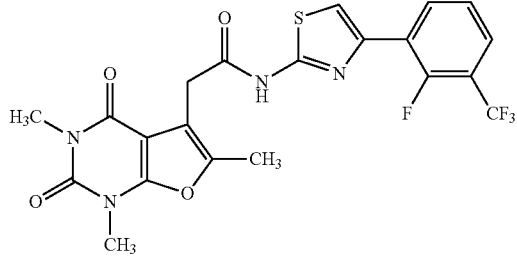
Compound 68
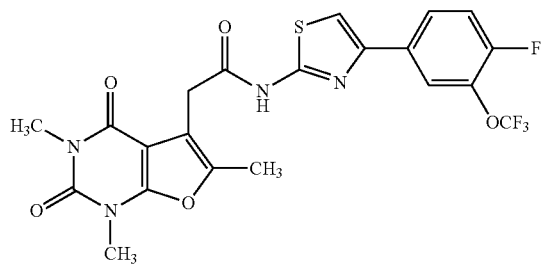
Compound 69
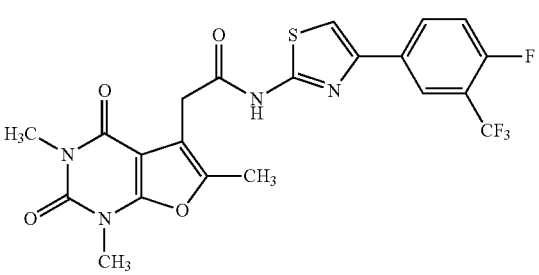
Compound 70
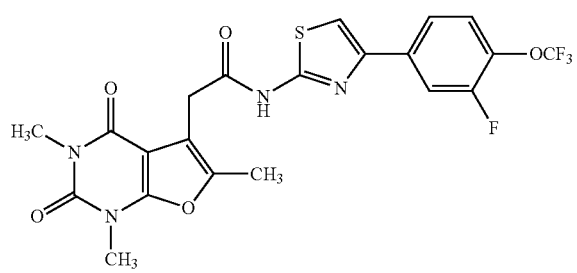

Compound 71
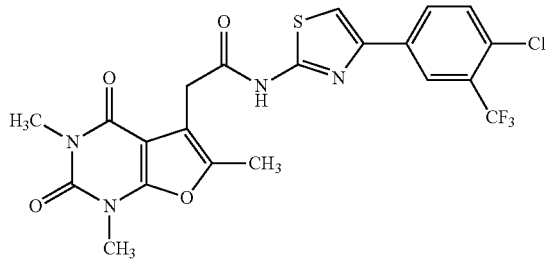

Compound 72
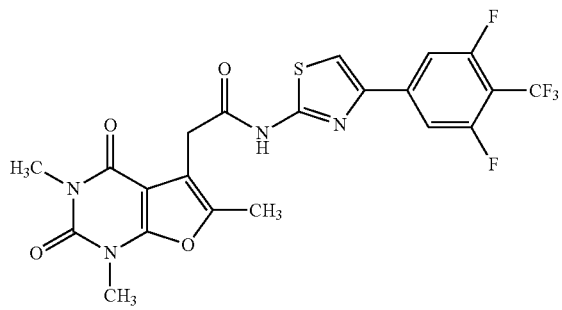

Compound 73
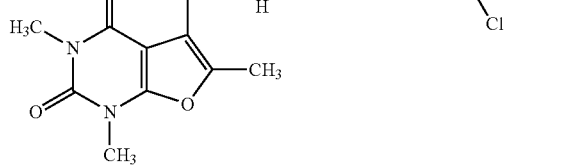

Compound 74
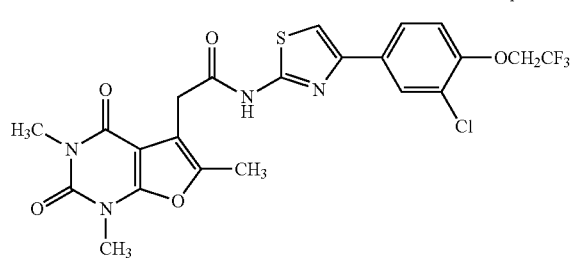

Compound 75
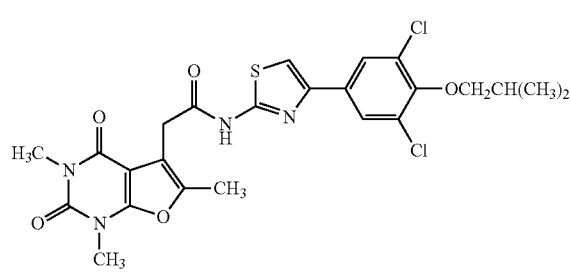

Compound 76
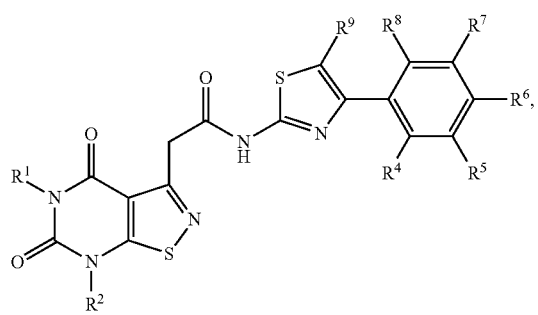

The preparation of above said compounds is described in WO2010109329.

In one embodiment, TRPA1 antagonists useful in the context of the invention are selected from those compounds generically or specifically disclosed in WO2010109328. Accordingly, TRPA1 antagonists useful in the context of the invention has the formula (VI)

(VI)

or a pharmaceutically-acceptable salt thereof
wherein, $R^1$ and $R^2$, which may be the same or different, are each independently hydrogen or $(C_1$-$C_4)$alkyl; and $R^4, R^5, R^6, R^7, R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

Few representative TRPA1 antagonists useful in the context of the invention are mentioned below:

Compound 77
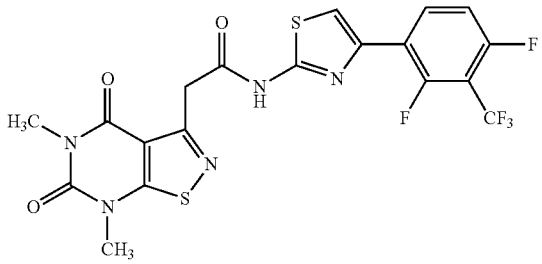

Compound 78
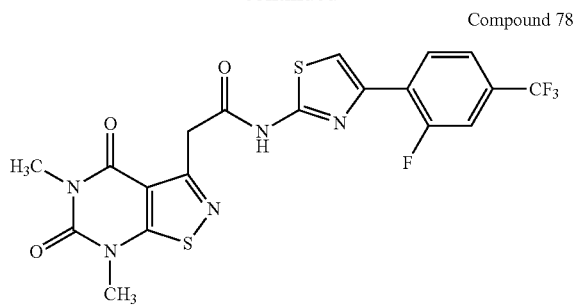

Compound 79
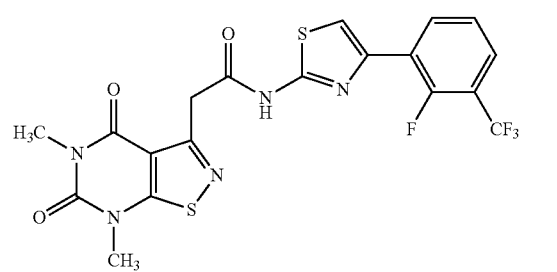

Compound 80
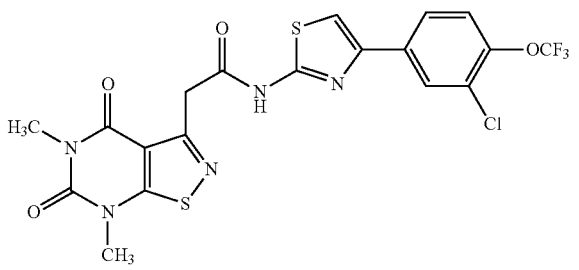

Compound 81
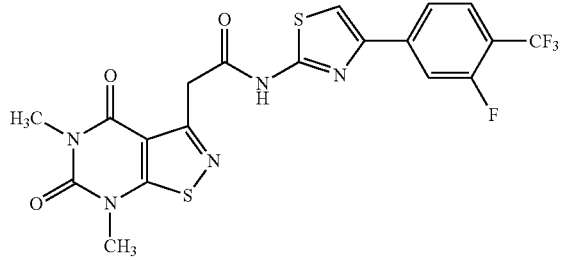

Compound 82
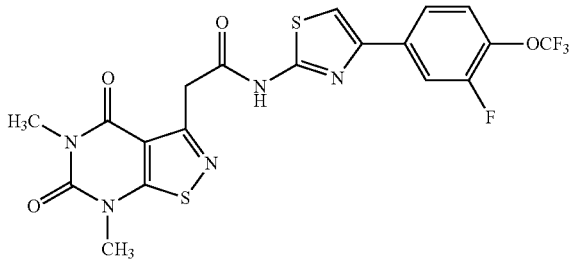

Compound 83

Compound 84
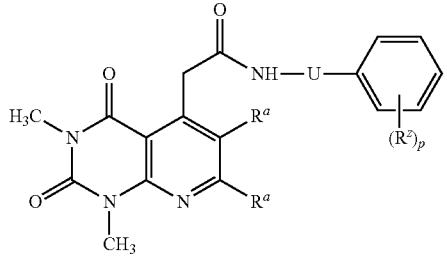

The preparation of above said compounds is described in WO2010109328.

In one embodiment, TRPA1 antagonists useful in the context of the invention are selected from those compounds generically or specifically disclosed in WO2010125469. Accordingly, TRPA1 antagonists useful in the context of the invention have the formulas (VIIa, VIIb and VIIc):

(VIIa)

(VIIb)
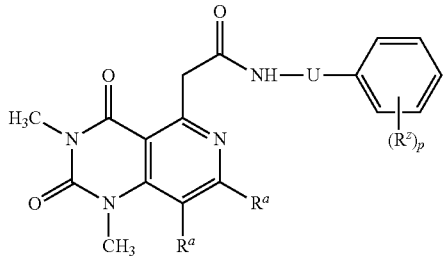

-continued

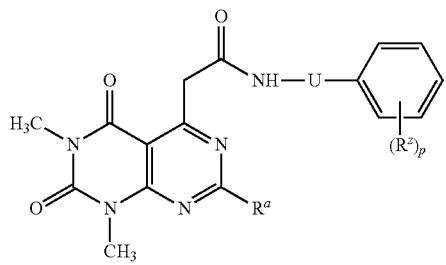

(VIIc)

or pharmaceutically acceptable salt thereof,
wherein, at each occurrence, $R^a$ is selected from hydrogen, cyano, halogen, substituted or unsubstituted alkyl, haloalkyl, alkenyl, alkynyl, alkoxy, cycloalkyl and cycloalkylalkyl;

U is substituted or unsubstituted five membered heterocycle, for example selected from the group consisting of

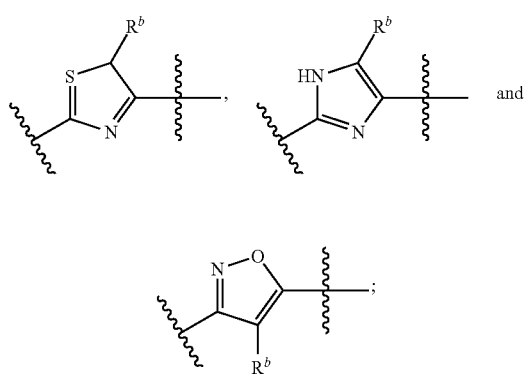

and at each occurrence, $R^b$ is independently selected from hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

at each occurrence, $R^z$ is independently selected from halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring, heterocyclylalkyl, COOR$^x$, CONR$^x$R$^y$, S(O)$_m$NR$^x$R$^y$, NR$^x$(CR$^x$R$^y$)$_n$OR$^x$, (CH$_2$)$_n$NR$^x$R$^y$, NR$^x$(CR$^x$R$^y$)$_n$CONR$^x$R$^y$, (CH$_2$)$_n$NHCOR$^x$, (CH$_2$)$_n$NH(CH$_2$)$_n$SO$_2$R$^x$ and (CH$_2$)$_n$NHSO$_2$R$^x$;

at each occurrence, $R^x$ and $R^y$ are independently selected from hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl;

at each occurrence, 'm' and 'n' are independently selected from 0 to 2, both inclusive; and 'p' is independently selected from 0 to 5, both inclusive.

Few representative TRPA1 antagonists useful in the context of the invention are mentioned below:

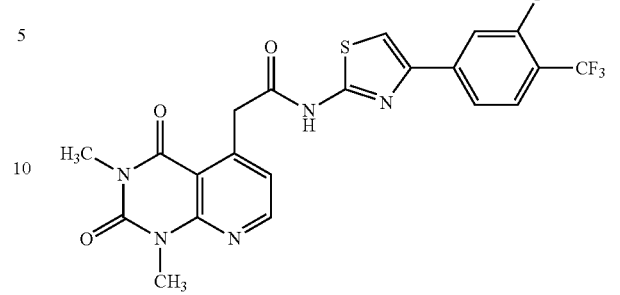

Compound 85

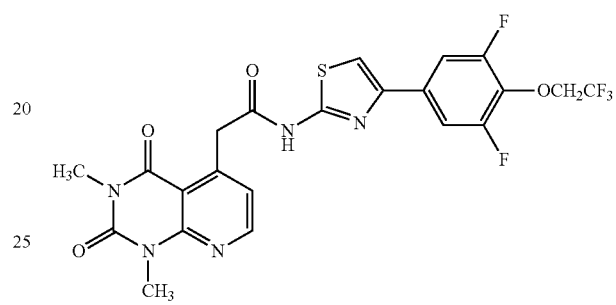

Compound 86

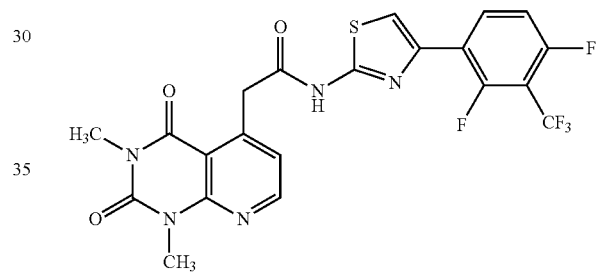

Compound 87

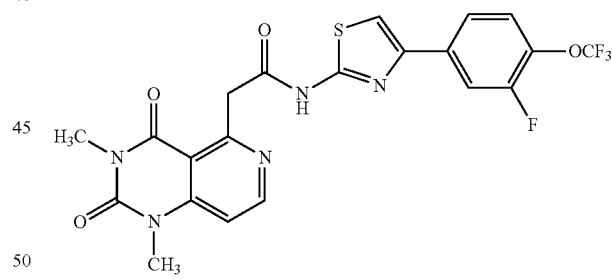

Compound 88

The preparation of above said compounds is described in WO2010125469.

In one embodiment, the TRPA1 antagonist useful in the context of the invention is Compound 89:

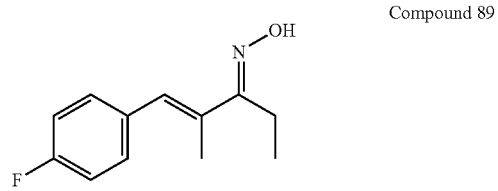

Compound 89

In one embodiment, the TRPA1 antagonist useful in the context of the invention is Compound 90:

Compound 90

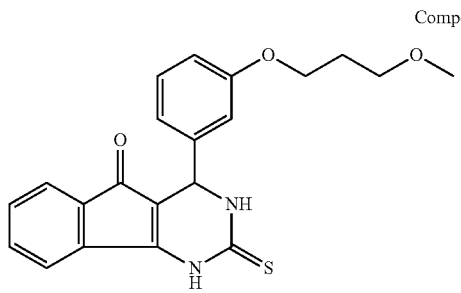

In an embodiment, TRPA1 antagonists useful in the context of the invention has the formula (VIII)

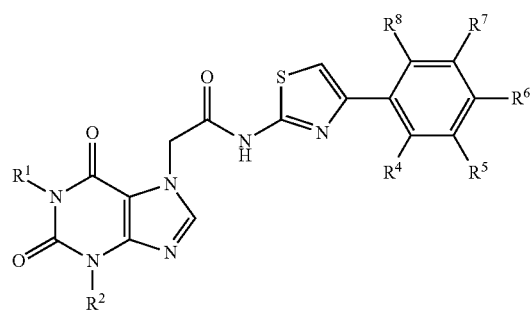

or a pharmaceutically-acceptable salt thereof
wherein,
$R^1$, $R^2$ and $R^a$, which may be the same or different, are each independently hydrogen or $(C_1-C_4)$alkyl;
$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

A representative TRPA1 antagonist useful in the context of the invention is Compound 91:

Compound 91

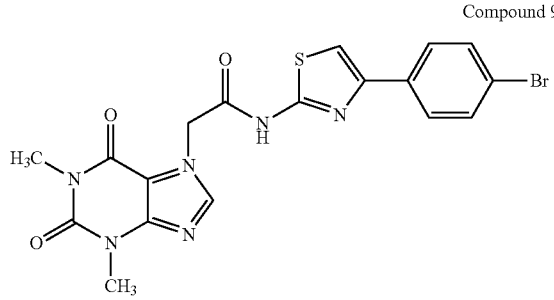

The Compound 91 may be prepared, for example, by following the process provided for the preparation of similar compounds in PCT publication No. WO2007073505.

In another embodiment, TRPA1 antagonists useful in the context of the invention are selected from those compounds generically or specifically disclosed in WO2011/114184. Accordingly, a TRPA1 antagonist useful in the context of the invention has the formula (IX):

(IX)

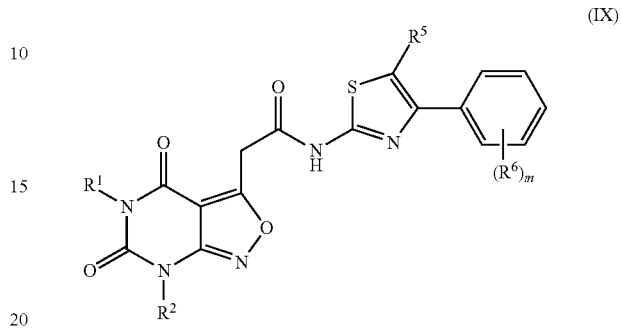

or a pharmaceutically-acceptable salt thereof
wherein at each occurrence, $R^1$ and $R^2$ are independently selected from hydrogen or substituted or unsubstituted alkyl;
at each occurrence, $R^5$ is selected from hydrogen, halogen or substituted or unsubstituted alkyl;
at each occurrence, $R^6$ is selected from hydrogen, cyano, nitro, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl.

A representative TRPA1 antagonist useful in the methods of the invention is mentioned below:

Compound 92

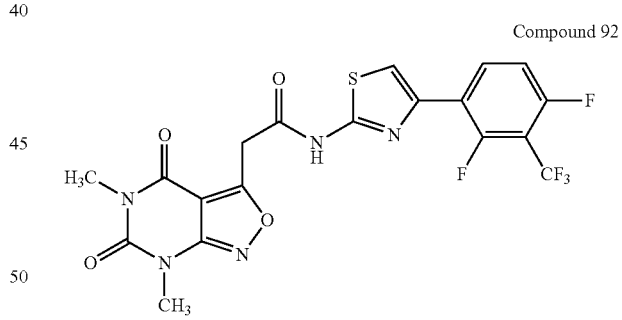

In another embodiment TRPA1 antagonist useful in the context of the invention has the formula (X):

(X)

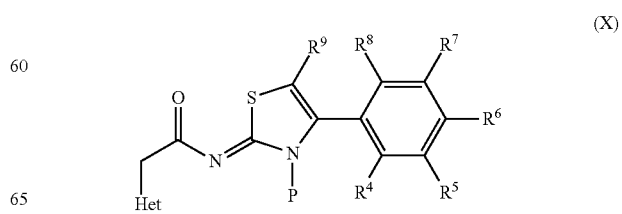

wherein,

'Het' is selected from groups consisting of

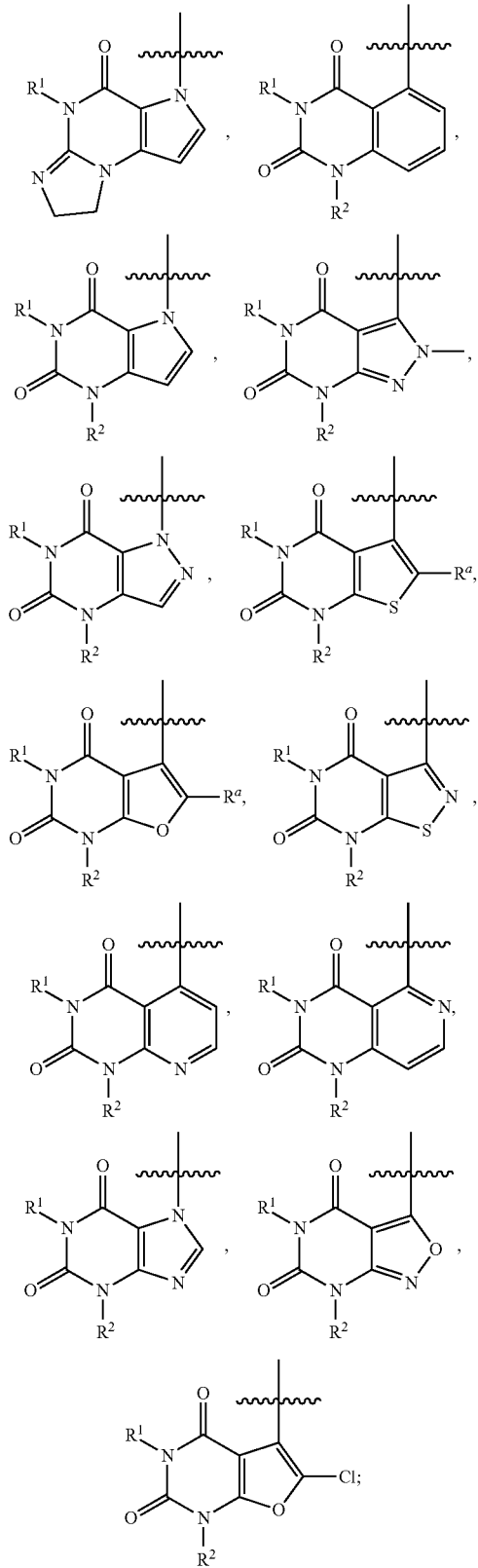

P is selected from

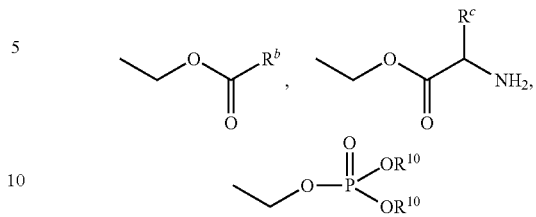

$R^1$, $R^2$ and $R^a$, which may be the same or different, are each independently hydrogen or $(C_1-C_4)$alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

$R^b$ and $R^c$ independently selected from hydrogen, substituted or unsubstituted alkyl arylalkyl, amino acid and heterocyclic ring;

$R^{10}$ is selected from hydrogen, alkyl, arylalkyl and pharmaceutically acceptable cation.

Few representative TRPA1 antagonists useful in the context of the invention are mentioned below:

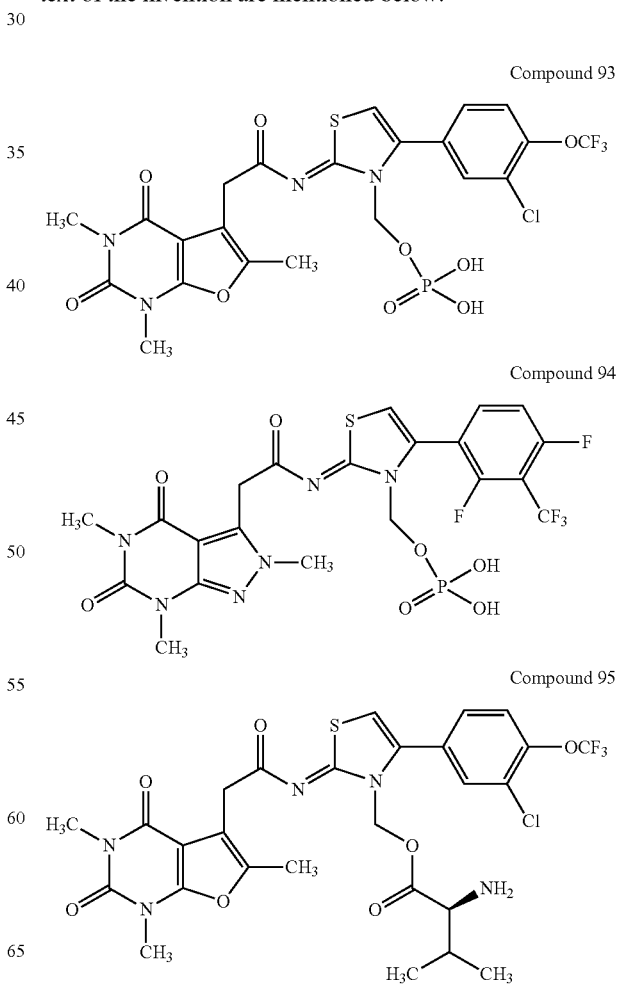

-continued

Compound 96
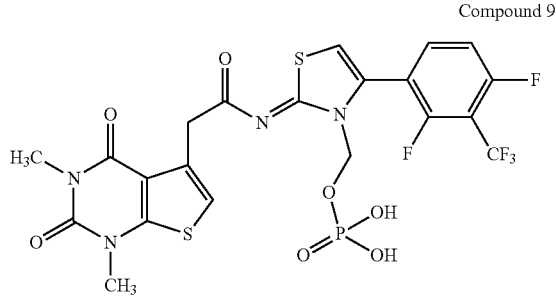

Compound 97
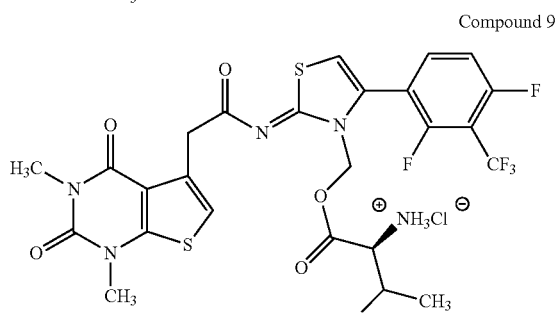

Compound 98
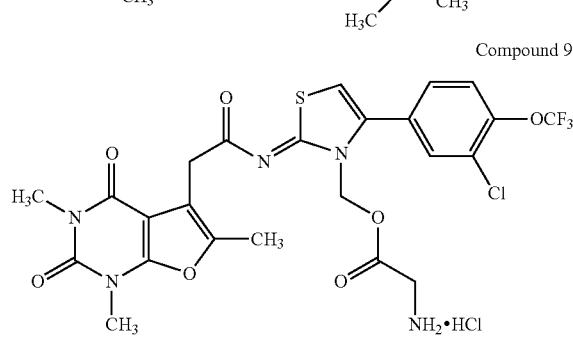

In another embodiment, TRPA1 antagonists useful in the context of the invention are selected from those compounds generically or specifically disclosed in WO2011114184. Accordingly, TRPA1 antagonist useful in the context of the invention has the formula (XI):

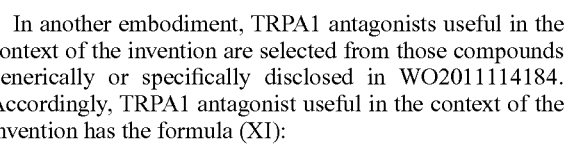

(XI)

or a pharmaceutically acceptable salt thereof,
wherein, $R^1$, and $R^2$ are independently hydrogen or $(C_1-C_4)$alkyl; and $R^4$, $R^5$, $R^6$, $R^7$, $R^8$ and $R^9$, which may be same or different, are each independently selected from halogen haloalkyl, dialkylamino, and haloalkoxy.

Few representative TRPA1 antagonists useful in the context of the invention are mentioned below:

Compound 99
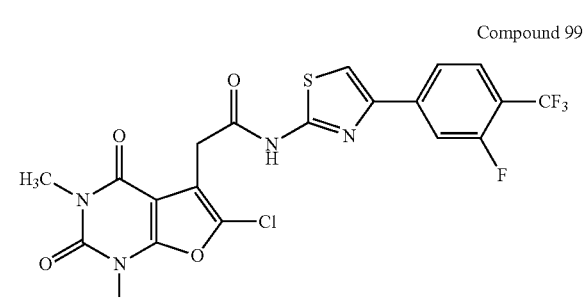

Compound 100
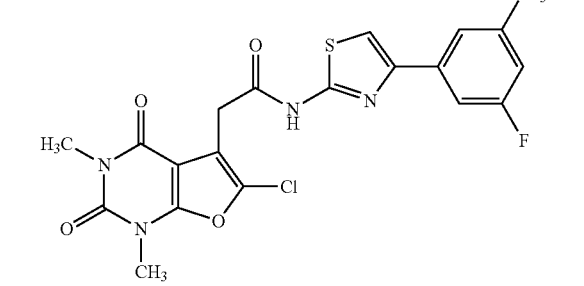

Compound 101
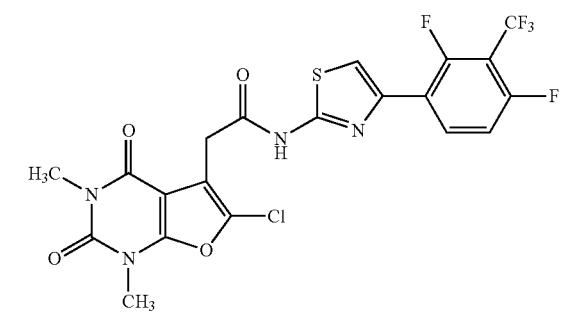

Compound 102
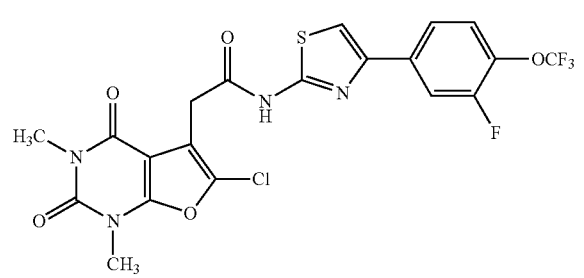

Compound 103
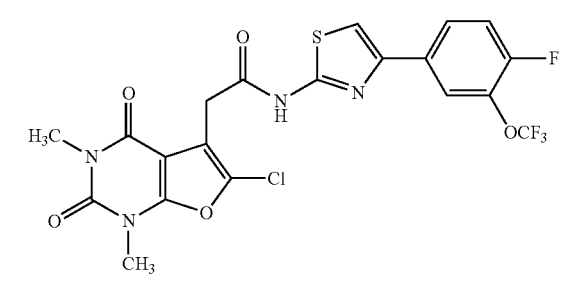

-continued

Compound 104

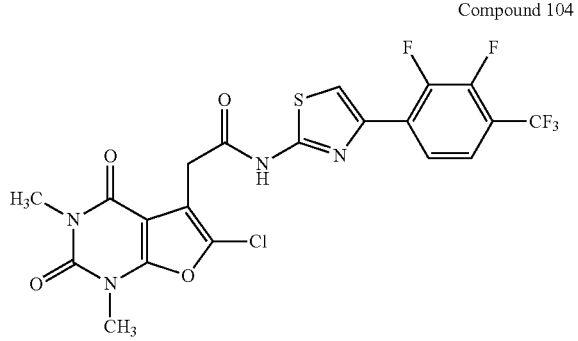 [SMILES: Cn1c(=O)c2c(CC(=O)Nc3nc(-c4ccc(C(F)(F)F)c(F)c4F)cs3)c(Cl)oc2n(C)c1=O]

The preparation of above said compounds is described in WO2011114184.

In an embodiment, TRPA1 antagonists useful in the context of the invention, is selected from one of the following formulae: (XII) or (D)

(XII)

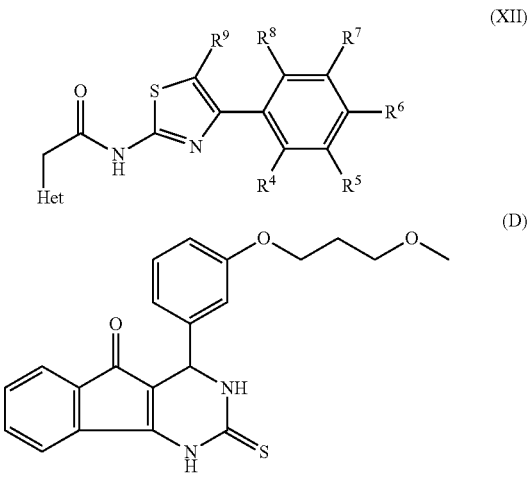

(D)

or a pharmaceutically-acceptable salt thereof, wherein, 'Het' is selected from the group consisting of

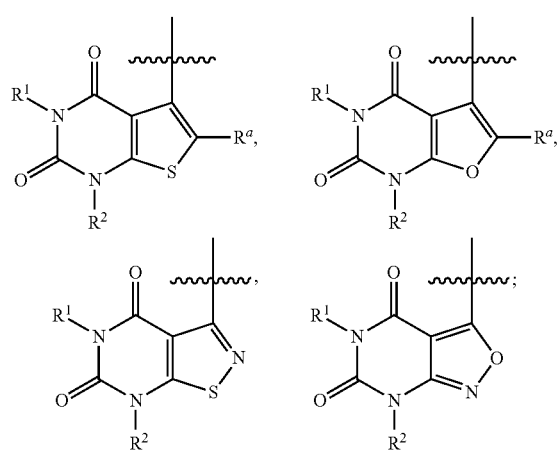

$R^1$, $R^2$ and $R^a$, which may be the same or different, are each independently hydrogen or $(C_1-C_4)$alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

Few representative TRPA1 antagonists of the formula (XII) useful in the context of the invention are compound 52, compound 73, compound 84 and compound 94 as described above.

Method of Treatment or Use

The present invention relates to treatment of a respiratory disorder using a TRPA1 antagonist, wherein the TRPA1 antagonist is administered by inhalation route to a subject in need thereof.

The inventors of the present invention have surprisingly found that the TRPA1 antagonists, which have high potency (e.g., $IC_{50}$ for inhibiting human TRPA1 receptor activity of less than 2 micromolar) combined with marked selectivity in the TRPA1 receptor over other types of TRP receptors, are effective in the treatment of respiratory disorders when administered to a subject by an inhalation route (e.g., by mouth and/or intranasal administration).

In an embodiment, the present invention relates to a method of treating a reducing eosinophil or neutrophil count in a subject having respiratory disorder in a subject, said method comprising administering to the subject by inhalation route an effective amount of a TRPA1 antagonist which has an $IC_{50}$ for inhibiting human TRPA1 receptor activity of less than 2 micromolar, thereby reducing said eosinophil or neutrophil count in said subject.

Preferably, the TRPA1 antagonists used in the method of treatment in accordance with the present invention have an $IC_{50}$ for inhibiting human TRPA1 receptor activity of less than 1 micromolar or less than 700 nanomolar, or more preferably, less than 500 nanomolar.

It is believed that reduction of eosinophil or neutrophil count and increase in FEV1 are important components of the treatment of respiratory disorders such as asthma and COPD. It is also believed that there exits an inverse correlation between eosinophil or neutrophil count and FEV1 value in human. For example, Ulrik C S, 1995 (Peripheral eosinophil counts as a marker of disease activity in intrinsic and extrinsic asthma; Clinical and Experimental Allergy; 1995, Volume 25, pages 820-827) discloses the relationship between eosinophil count and severity of asthmatic symptoms. It describes that in childhood and adulthood subjects, there exists an inverse correlation between number of eosinophils and FEV1% (r=−0.75, P<0.001, and r=−0.80, P<0.001, respectively).

Further, Peleman R A, 1999 (The cellular composition of induced sputum in chronic obstructive pulmonary disease; European Respiratory Journal; 1999, Volume 13, pages 839-843) discloses the relationship between percentage of neutrophils and FEV1 in patients with COPD. It describes that in patients with COPD, an inverse correlation was noted between percentage of neutrophils and FEV1 (r=−0.48, p<0.05).

In an embodiment, the present invention relates to a method of treating a respiratory disorder by reducing eosinophil or neutrophil count in a subject, said method comprising administering to the subject by inhalation route an effective amount of TRPA1 antagonists which are amides of 4-aryl-2-amino-thiazole compounds, wherein aryl may be substituted or unsubstituted phenyl.

In yet another embodiment, the present invention relates to a method of reducing eosinophil or neutrophil count and/or increasing FEV1 in a subject having a respiratory disorder (such as asthma or COPD), said method comprising administering to the subject by inhalation route an effective amount of a TRPA1 antagonist has an $IC_{50}$ for inhibiting human TRPV1, TRPV3, TRPV4 and TRPM8 receptor activity greater than at least 10 times the $IC_{50}$ for inhibiting human TRPA1 receptor activity. Preferably, the TRPA1 antagonist has an $IC_{50}$ for inhibiting human TRPV1, TRPV3, TRPV4 and TRPM8 receptor activity greater than at least 100 times the $IC_{50}$ for inhibiting human TRPA1 receptor activity. In an aspect, the TRPA1 antagonist is a selective TRPA1 antagonist. In an aspect, TRPA1 antagonist useful in the context of the invention, is selected from one of the following formulae: (A) or (B) or (C) or (D)

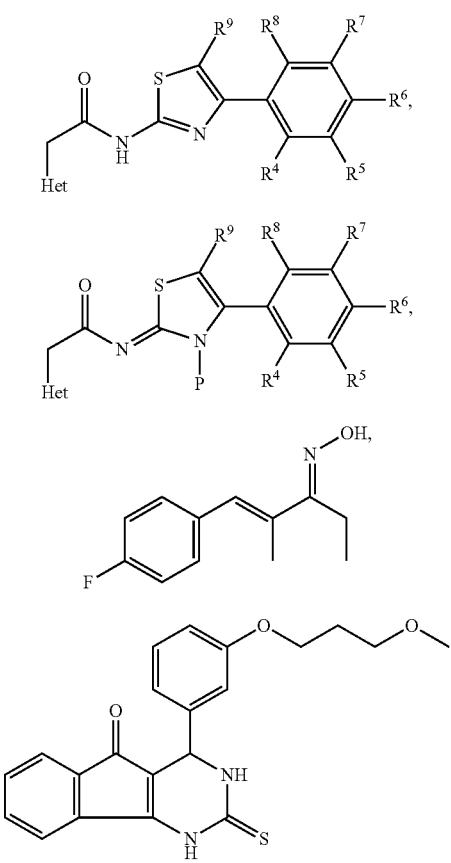

or a pharmaceutically-acceptable salt thereof, wherein, 'Het' is selected from the group consisting of

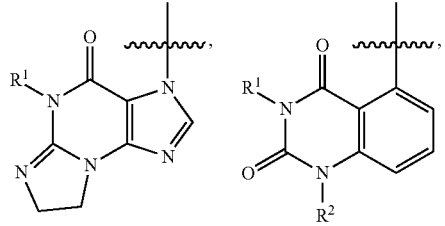

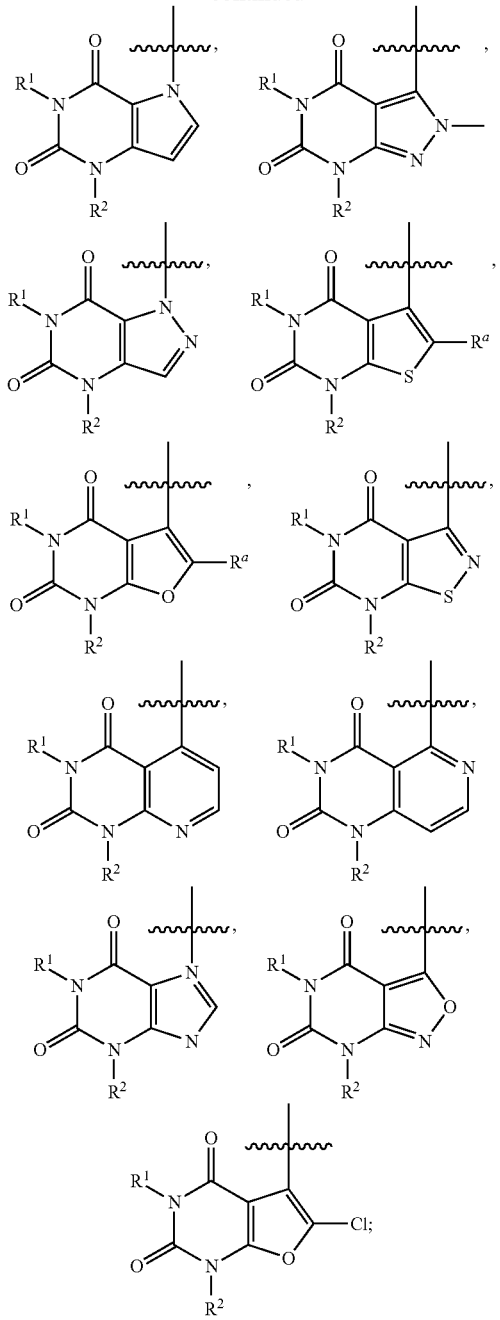

P is selected from

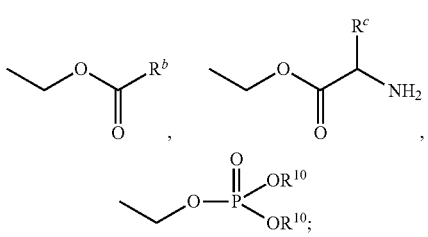

$R^1$, $R^2$ and $R^a$, which may be the same or different, are each independently hydrogen or $(C_1-C_4)$alkyl;

$R^b$ and $R^c$ independently selected from hydrogen, substituted or unsubstituted alkyl arylalkyl, amino acid and heterocyclic ring;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

$R^{10}$ is selected from hydrogen, alkyl, arylalkyl and pharmaceutically acceptable cation.

In an embodiment, the present invention relates to a method of reducing eosinophil or neutrophil count and/or increasing FEV1 in a subject having a respiratory disorder in a subject, said method comprising administering to the subject by inhalation route an effective amount of a TRPA1 antagonist of formulae (XII) or (D)

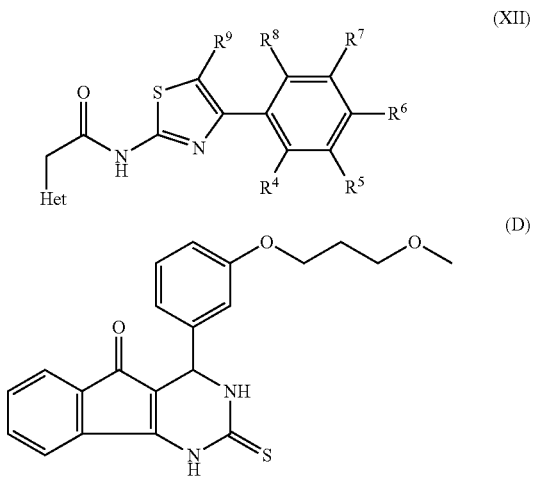
(XII)

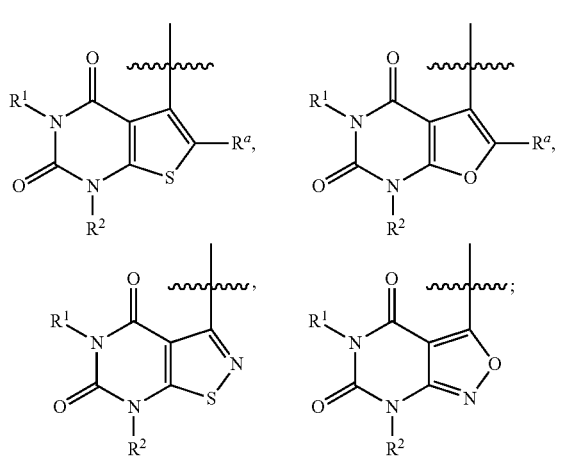
(D)

or a pharmaceutically-acceptable salt thereof, wherein, 'Het' is selected from the group consisting of

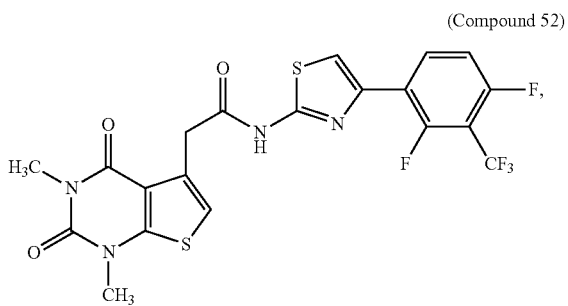 [SMILES: Cn1c(=O)c2c(CC(=O)Nc3nc(-c4ccc(F)c(C(F)(F)F)c4F)cs3)csc2n(C)c1=O]

$R^1$, $R^2$ and $R^a$, which may be the same or different, are each independently hydrogen or ($C_1$-$C_4$)alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

In an embodiment, the present invention relates to a method of reducing eosinophil or neutrophil count and/or increasing FEV1 in a subject having a respiratory disorder, said method comprising administering to the subject by inhalation route an effective amount of a TRPA1 antagonist is

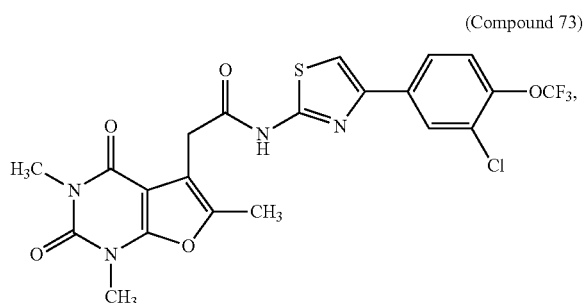
(Compound 52)

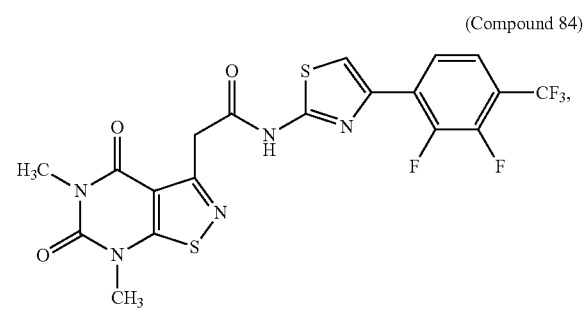 [SMILES: Cn1c(=O)c2c(CC(=O)Nc3nc(-c4ccc(C(F)(F)F)c(F)c4F)cs3)nsc2n(C)c1=O]
(Compound 73)

(Compound 84)

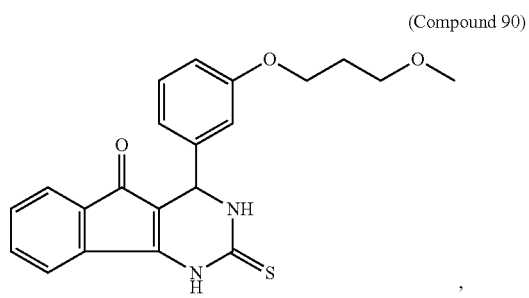 [SMILES: COCCCOc1cccc(C2NC(=S)NC3=C2C(=O)c2ccccc23)c1]
(Compound 90)

(Compound 92)

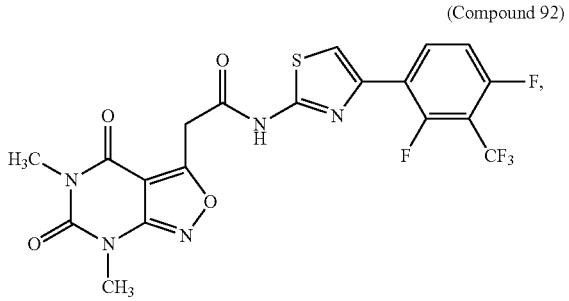 [SMILES: Cn1c(=O)c2c(CC(=O)Nc3nc(-c4ccc(F)c(C(F)(F)F)c4F)cs3)onc2n(C)c1=O]

or a pharmaceutically acceptable salt thereof.

Preferably, the TRPA1 antagonists may be selected from Compound 52, Compound 73, Compound 84, Compound 90, Compound 92 or a pharmaceutically acceptable salt thereof.

Thus, in a specific embodiment, the present invention relates to a method of treating a respiratory disorder (such as asthma or COPD) by reducing eosinophil or neutrophil count and/or increasing FEV1, in a subject, said method comprising administering to the subject by inhalation route an effective amount of Compound 52 or its pharmaceutically acceptable salt.

In another specific embodiment, the present invention relates to a method of treating a respiratory disorder (such as asthma or COPD) by reducing eosinophil or neutrophil count and/or increasing FEV1 in a subject, said method comprising administering to the subject by inhalation route an effective amount of Compound 73 or its pharmaceutically acceptable salt.

In yet another specific embodiment, the present invention relates to a method of treating a respiratory disorder (such as asthma or COPD) by reducing eosinophil or neutrophil count and/or increasing FEV1, in a subject, said method comprising administering to the subject by inhalation route an effective amount of Compound 84 or its pharmaceutically acceptable salt.

In another specific embodiment, the present invention relates to a method of treating a respiratory disorder (such as asthma or COPD) by reducing eosinophil or neutrophil count and/or increasing FEV1, in a subject, said method comprising administering to the subject by inhalation route an effective amount of Compound 90 or its pharmaceutically acceptable salt.

In a further specific embodiment, the present invention relates to a method of treating a respiratory disorder (such as asthma or COPD) by reducing eosinophil or neutrophil count and/or increasing FEV1, in a subject, said method comprising administering to the subject by inhalation route an effective amount of Compound 92 or its pharmaceutically acceptable salt.

The $IC_{50}$ value is believed to be measure of the effectiveness of a compound in inhibiting biological or biochemical function. This quantitative measure generally indicates molar concentration of a particular compound (or substance) that is needed to inhibit a given biological process by half. In other words, it is the half maximal (50%) inhibitory concentration (IC) of the compound. The $IC_{50}$ of a drug compound can be determined by constructing a concentration-response curve so as to examine the effect of different concentrations of antagonist on reversing agonist activity. The $IC_{50}$ values can be calculated for a given antagonist by determining the concentration needed to inhibit half of the maximum biological response of the agonist. These values can be used to compare the potency of two antagonists.

As contemplated herein, the $IC_{50}$ value is measured by the following method. The inhibition of TRPA1 receptor activation is measured as inhibition of allylisothiocyanate (AITC) induced cellular uptake of radioactive calcium. Test solution of test compound is prepared in a suitable solvent using appropriate method. Human TRPA1 expressing CHO cells are grown in suitable medium. Cells are treated with test compounds followed by addition of AITC. Cells are washed and lysed. Radioactivity in the lysate is measured in Packard Top count after addition of liquid scintillant. The concentration response curves for compounds are plotted as a % of maximal response obtained in the absence of test antagonist, and the $IC_{50}$ values are calculated from such concentration response curve by nonlinear regression analysis using GraphPad PRISM software.

In a preferred embodiment, the present invention relates to a method of reducing eosinophil or neutrophil count and increasing FEV1 in a subject having a respiratory disorder in a subject, said method comprising administering to the subject by inhalation route an effective amount of a TRPA1 antagonist which has an $IC_{50}$ for inhibiting human TRPA1 receptor activity of less than 2 micromolar or less than 1 micromolar or preferably less than 700 nanomolar, or more preferably less than 500 nanomolar.

Asthma and COPD are major chronic diseases related to airway obstruction. The Global Initiative for Chronic Obstructive Lung Disease provides guidelines for the distinction between asthma and COPD. Asthma is believed to be a chronic inflammatory disease wherein the airflow limitation is more or less reversible while it is more or less irreversible in case of COPD. Asthma among other things is believed to be triggered by inhalation of sensitizing agents (like allergens) unlike noxious agents (like particles and certain gases) in case of COPD. Though both are believed to have an inflammatory component, the inflammation in asthma is believed to be mostly eosinophilic and CD-4 driven, while it is believed to be mostly neutrophilic and CD-8 driven in COPD. Human airways are innervated by a generous supply of efferent, cholinergic, parasympathetic autonomic nerves.

Asthma is clinically classified according to the frequency of symptoms, forced expiratory volume in 1 second ($FEV_1$), peak expiratory flow rate and severity (e.g., acute, intermittent, mild persistent, moderate persistent, and severe persistent). Asthma may also be classified as allergic (extrinsic) or non-allergic (intrinsic), based on whether symptoms are precipitated by allergens or not. Asthma can also be categorized according to following types viz., nocturnal asthma, bronchial asthma, exercise induced asthma, occupational asthma, seasonal asthma, silent asthma, and cough variant asthma.

TRPA1 is an irritant-sensing ion channel expressed on the airway chemosensory nerves of bronchopulmonary region and may function as an integrator of chemical and immunological stimuli modulating inflammation in the airways. Various respiratory irritants including environmental pollutants, cigarette smoke, chlorine and aldehydes are believed to directly activate TRPA1 and are among the most prevalent triggers of asthma and COPD. Cigarette smoke constituents such as acrolein and crotonaldehyde, by stimulation of TRPA1, mediate airway neurogenic inflammatory responses evoked by cigarette smoke. Thus, in chronic respiratory condition such as COPD, TRPA1 pathway plays a major role in mediating cigarette smoke induced bronchial inflammation.

COPD, also known as chronic obstructive lung disease (COLD), chronic obstructive airway disease (COAD), or chronic obstructive respiratory disease (CORD), is believed to be the co-occurrence of chronic bronchitis (characterized by a long-term cough with mucus) and emphysema (characterized by destruction of the lungs over time), a pair of commonly co-existing diseases of the lungs in which the airways become narrowed. This leads to a limitation of the flow of air to and from the lungs, causing shortness of breath. An acute exacerbation of COPD is a sudden worsening of COPD symptoms (shortness of breath, quantity and color of phlegm) that typically lasts for several days and is believed to be triggered by an infection with bacteria or viruses or by environmental pollutants. Based on the $FEV_1$ values, COPD can be classified as mild, moderate, severe and very severe.

In one embodiment, the present invention relates to a method of treating a respiratory disorder by reducing eosinophil or neutrophil count and increasing FEV1 in a subject, said method comprising administering to the subject by inhalation route an effective amount of TRPA1 antagonist which has an $IC_{50}$ for inhibiting human TRPA1 receptor activity of less than 2 micromolar or less than 1 micromolar or preferably less than 700 nanomolar or more preferably less than 500 nanomolar. Preferably, the TRPA1 antagonist is selected from Compound 52, Compound 73, Compound 84, Compound 90, Compound 92 or a pharmaceutically acceptable salt thereof.

Thus specifically, in an embodiment, the present invention relates to a method of treating a respiratory disorder by reducing eosinophil or neutrophil count and increasing FEV1 in a subject, said method comprising administering to the subject by inhalation route an effective amount of Compound 52 or its pharmaceutically acceptable salt.

In another specific embodiment, the present invention relates to a method of treating a respiratory disorder by reducing eosinophil or neutrophil count and increasing FEV1 in a subject, said method comprising administering to the subject by inhalation route an effective amount of Compound 73 or its pharmaceutically acceptable salt.

In yet another specific embodiment, the present invention relates to a method of treating a respiratory disorder by reducing eosinophil or neutrophil count and increasing FEV1 in a subject, said method comprising administering to the subject by inhalation route an effective amount of Compound 84 or its pharmaceutically acceptable salt.

In another specific embodiment, the present invention relates to a method of treating a respiratory disorder by reducing eosinophil or neutrophil count and increasing FEV1 in a subject, said method comprising administering to the subject by inhalation route an effective amount of Compound 90 or its pharmaceutically acceptable salt.

In a further specific embodiment, the present invention relates to a method of treating a respiratory disorder by reducing eosinophil or neutrophil count and increasing FEV1 in a subject, said method comprising administering to the subject by inhalation route an effective amount of Compound 92 or its pharmaceutically acceptable salt.

In an embodiment, the present invention relates to a method of treating a respiratory disorder (such as asthma or COPD) by reducing the eosinophil or neutrophil count and/or airway hyper-reactivity/responsiveness in a subject, said method comprising administering to the subject by inhalation route an effective amount of a TRPA1 antagonist which has an $IC_{50}$ for inhibiting human TRPA1 receptor activity of less than 2 micromolar or less than 1 micromolar or preferably less than 700 nanomolar or more preferably less than 500 nanomolar.

Specifically, in an embodiment, the present invention relates to a method of treating a respiratory disorder by reducing eosinophil or neutrophil count and/or airway hyper-reactivity/responsiveness in a subject, said method comprising administering to the subject by inhalation route a therapeutically effective amount of Compound 52 or its pharmaceutically acceptable salt.

In another specific embodiment, the present invention relates to a method of treating a respiratory disorder by reducing eosinophil or neutrophil count and/or airway hyper-reactivity/responsiveness in a subject, said method comprising administering to the subject by inhalation route a therapeutically effective amount of Compound 73 or its pharmaceutically acceptable salt.

In yet another specific embodiment, the present invention relates to a method of treating a respiratory disorder by reducing eosinophil or neutrophil count and/or airway hyper-reactivity/responsiveness in a subject, said method comprising administering to the subject by inhalation route a therapeutically effective amount of Compound 84 or its pharmaceutically acceptable salt.

In a further specific embodiment, the present invention relates to a method of treating a respiratory disorder by reducing eosinophil or neutrophil count and/or airway hyper-reactivity/responsiveness in a subject, said method comprising administering to the subject by inhalation route a therapeutically effective amount of Compound 90 or its pharmaceutically acceptable salt.

In another specific embodiment, the present invention relates to a method of treating a respiratory disorder by reducing eosinophil or neutrophil count and/or airway hyper-reactivity/responsiveness in a subject, said method comprising administering to the subject by inhalation route a therapeutically effective amount of Compound 92 or its pharmaceutically acceptable salt.

In another embodiment, the present invention relates to a method of treating a respiratory disorder (such as asthma or COPD) by reducing eosinophil or neutrophil count and/or increasing FEV1 in a subject, said method comprising administering to the subject by inhalation route a TRPA1 antagonist in an amount ranging from about 1 mcg to about 20 mg or preferably from about 10 mcg to about 10 mg. Preferably, the TRPA1 antagonist is selected from Compound 52 or Compound 73 or Compound 84 or Compound 90 or Compound 92 or a pharmaceutically acceptable salt thereof.

In the context of the present invention, the inhalation route comprises nasal or oral inhalation or both wherein the TRPA1 antagonists are administered to intra-tracheal region of the subject. The compositions suitable for administration by inhalation route include dry powder inhaler (DPI) formulations, metered dose inhaler (MDI) formulations, nasal sprays, and formulations suitable for nebulization.

As contemplated herein, the TRPA1 antagonists of the present invention exhibits marked selectivity (at least 10 fold) for inhibition of human TRPA1 receptor activity over the other TRP receptor family members such as human TRPV1, TRPV3, TRPV4 and TRPM8 receptors.

In an embodiment, the present invention relates to a method of treating a respiratory disorder (such as asthma or COPD) by reducing eosinophil or neutrophil count and/or increasing FEV1 in a subject, said method comprising administering to the subject by inhalation route an effective amount of a TRPA1 antagonist which has an $IC_{50}$ for inhibiting human TRPA1 receptor activity of less than 2 micromolar or preferably less than 1 micromolar, or preferably less than 700 nanomolar, or even more preferably less than 500 nanomolar, and wherein the TRPA1 antagonist has an $IC_{50}$ for inhibiting human TRPV1 receptor activity greater than at least 10 times the $IC_{50}$ for inhibiting human TRPA1 receptor activity. Preferably, the TRPA1 antagonist has an $IC_{50}$ for inhibiting human TRPV1 receptor activity greater than at least 100 times the $IC_{50}$ for inhibiting human TRPA1 receptor activity.

In another aspect, the present invention relates to a method of treating a respiratory disorder (such as asthma or COPD) by reducing eosinophil or neutrophil count and/or increasing FEV1 in a subject, said method comprising administering to the subject by inhalation route an effective amount of a TRPA1 antagonist which has an $IC_{50}$ for inhibiting human TRPA1 receptor activity of 2 micromolar or preferably less than 1 micromolar, or preferably less than 700 nanomolar, or even more preferably less than 500 nanomolar, and wherein the TRPA1 antagonist has an $IC_{50}$ for inhibiting human TRPV3 receptor activity greater than at least 10 times the $IC_{50}$ for inhibiting human TRPA1 receptor activity. Preferably, the TRPA1 antagonist has an $IC_{50}$ for inhibiting human TRPV3 receptor activity greater than at least 100 times the $IC_{50}$ for inhibiting human TRPA1 receptor activity.

In yet another aspect, the present invention relates to a method of treating a respiratory disorder (such as asthma or COPD) by reducing eosinophil or neutrophil count and/or increasing FEV1 in a subject, said method comprising administering to the subject by inhalation route an effective amount of a TRPA1 antagonist which has an $IC_{50}$ for inhibiting human TRPA1 receptor activity of less than 2 micromolar or preferably less than 1 micromolar, or preferably less than 700 nanomolar, or even more preferably less than 500 nanomolar, and wherein the TRPA1 antagonist has an $IC_{50}$ for inhibiting human TRPV4 receptor activity greater than at least 10 times the $IC_{50}$ for inhibiting human TRPA1 receptor activity. Preferably, the TRPA1 antagonist has an $IC_{50}$ for inhibiting human TRPV4 receptor activity greater than at least 100 times the $IC_{50}$ for inhibiting human TRPA1 receptor activity.

In a further aspect, the present invention relates to a method of treating a respiratory disorder (such as asthma or COPD) by reducing eosinophil or neutrophil count and/or increasing FEV1, in a subject, said method comprising administering to the subject by inhalation route an effective amount of a TRPA1 antagonist which has an $IC_{50}$ for inhibiting human TRPA1 receptor activity of less than 2 micromolar or preferably less than 1 micromolar, or preferably less than 700 nanomolar, or even more preferably less than 500 nanomolar, and wherein the TRPA1 antagonist has an $IC_{50}$ for inhibiting human TRPM8 receptor activity greater than at least 10 times the $IC_{50}$ for inhibiting human TRPA1 receptor activity. Preferably, the TRPA1 antagonist has an $IC_{50}$ for inhibiting human TRPM8 receptor activity greater than at least 100 times the $IC_{50}$ for inhibiting human TRPA1 receptor activity.

In an embodiment, the present invention relates to a method of treating a respiratory disorder in a subject by reducing eosinophil or neutrophil count and/or increasing FEV1, said method comprising administering to the subject by nasal or oral inhalation route an effective amount of a TRPA1 antagonist which has an $IC_{50}$ for inhibiting human TRPA1 receptor activity of less than 2 micromolar or less than 1 micromolar, wherein such inhibition of human TRPA1 receptor activity is the principal therapeutic mode of action of the TRPA1 antagonist, and wherein, (a) the TRPA1 antagonist has an $IC_{50}$ for inhibiting human TRPV1 receptor activity greater than at least 10 times the $IC_{50}$ for inhibiting human TRPA1 receptor activity; and/or (b) the TRPA1 antagonist has an $IC_{50}$ for inhibiting human TRPV3 receptor activity greater than at least 10 times the $IC_{50}$ for inhibiting human TRPA1 receptor activity; and/or (c) the TRPA1 antagonist has an $IC_{50}$ for inhibiting human TRPV4 receptor activity greater than at least 10 times the $IC_{50}$ for inhibiting human TRPA1 receptor activity; and/or (d) the TRPA1 antagonist has an $IC_{50}$ for inhibiting human TRPM8 receptor activity greater than at least 10 times the $IC_{50}$ for inhibiting human TRPA1 receptor activity.

In an aspect, the TRPA1 antagonist is selective TRPA1 antagonist.

The present invention also relates to a method of identifying a TRPA1 antagonist useful for treating a respiratory disorder, such as asthma or COPD, by inhalation administration in a subject, said method comprising:

(a) determining an $IC_{50}$ for inhibiting human TRPA1 receptor activity of each of the plurality of compounds;

(b) selecting the compounds which has an $IC_{50}$ for inhibiting human TRPA1 receptor activity of less than 2 micromolar;

(c) determining $IC_{50}$ of such compounds for inhibiting human TRPV1, TRPV3, TRPV4 and/or TRPM8 receptor activities;

(d) identifying such compounds which have the $IC_{50}$ for inhibiting human TRPV1, TRPV3, TRPV4 and/or TRPM8 receptor activities greater than at least 10 times the $IC_{50}$ for inhibiting human TRPA1 receptor activity;

(e) evaluating the in vivo activity of the identified compounds in a respiratory disorder model, wherein the compounds are administered by inhalation route; and (f) identifying the compounds to be effective for treating the respiratory disorder.

In an embodiment, the present invention relates to a TRPA1 antagonist which has an $IC_{50}$ for inhibiting human TRPA1 receptor activity of less than 2 micromolar for the treating a respiratory disorder by reducing eosinophil or neutrophil count and/or increasing FEV1 in a subject by administering an effective amount of the TRPA1 antagonist by inhalation route. Preferably, the TRPA1 antagonist has an $IC_{50}$ for inhibiting human TRPA1 receptor activity of less than 1 micromolar or less than 700 nanomolar, or more preferably, less than 500 nanomolar.

In another aspect, the present invention relates to a TRPA1 antagonist which has an $IC_{50}$ for inhibiting human TRPA1 receptor activity of less than less than 2 micromolar or less than 1 micromolar, or preferably less than 700 nanomolar, or even more preferably less than 500 nanomolar for the treating asthma or COPD by reducing eosinophil or neutrophil count and/or increasing FEV1 in a subject by administering an effective amount of the TRPA1 antagonist by inhalation route.

In yet another aspect, the present invention relates to a TRPA1 antagonist which has an $IC_{50}$ for inhibiting human TRPA1 receptor activity of less than less than 2 micromolar or less than 1 micromolar, or preferably less than 700 nanomolar, or even more preferably less than 500 nanomolar for the treating a respiratory disorder by reducing the eosinophil or neutrophil count and/or airway hyper-reactivity/responsiveness in a subject by administering an effective amount of the TRPA1 antagonist by inhalation route.

In another aspect, the present invention relates to a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar, for the treating a respiratory disorder by reducing eosinophil or neutrophil count and/or increasing FEV1, such as asthma or COPD, in a subject by administering an effective amount of the TRPA1 antagonist by inhalation route, wherein such inhibition of human TRPA1 receptor activity is the principal therapeutic mode of action of the TRPA1 antagonist. It is contemplated that inhibition of human TRPA1 receptor activity could be principal but not exclusive mode of action of the TRPA1 antagonist.

Particularly contemplated are TRPA1 antagonists for which inhibition of human TRPA1 receptor activity is principal but not exclusive mode of action of the TRPA1 antagonist, with the proviso that this embodiment of the invention does include compounds 52, 73, 76, 84, 90 and 92. Also particularly contemplated are TRPA1 antagonists for which inhibition of human TRPA1 receptor activity is principal but not exclusive mode of action of the TRPA1 antagonist, with the proviso that this embodiment of the invention does include compounds 2, 3, 7, 13, 18, 19, 20, 21, 28, 51, 59, 77, 78, 79, 80, 81, 82, 83, 84, 85, 87, and 88.

In an embodiment, the present invention relates to Compound 52 or its pharmaceutically acceptable salt for the treating a respiratory disorder by reducing eosinophil or neutrophil count and/or increasing FEV1 in a subject comprising administering to the subject an effective amount of the Compound 52 or its pharmaceutically acceptable salt by inhalation route.

In another embodiment, the present invention relates to Compound 73 or its pharmaceutically acceptable salt for the treating a respiratory disorder by reducing eosinophil or neutrophil count and/or increasing FEV1 in a subject comprising administering to the subject an effective amount of the Compound 73 or its pharmaceutically acceptable salt by inhalation route.

In yet another embodiment, the present invention relates to Compound 84 or its pharmaceutically acceptable salt for the treating a respiratory disorder by reducing eosinophil or neutrophil count and/or increasing FEV1 in a subject comprising administering to the subject an effective amount of the Compound 84 or its pharmaceutically acceptable salt by inhalation route.

In another embodiment, the present invention relates to Compound 90 or its pharmaceutically acceptable salt for the treating a respiratory disorder by reducing eosinophil or neutrophil count and/or increasing FEV1 in a subject comprising administering to the subject an effective amount of the Compound 90 or its pharmaceutically acceptable salt by inhalation route.

In a further embodiment, the present invention relates to Compound 92 or its pharmaceutically acceptable salt for the treating a respiratory disorder by reducing eosinophil or neutrophil count and/or increasing FEV1 in a subject comprising administering to the subject an effective amount of the Compound 92 or its pharmaceutically acceptable salt by inhalation route.

Thus in a specific embodiment, the present invention relates to Compound 52 or its pharmaceutically acceptable salt for treating a respiratory disorder such as asthma or COPD by reducing eosinophil or neutrophil count and/or increasing FEV1, in a subject by administering an effective amount of Compound 52 or its pharmaceutically acceptable salt by inhalation route, wherein inhibition of human TRPA1 receptor activity is the principal therapeutic mode of action of Compound 52 or its pharmaceutically acceptable salt.

In another specific embodiment, the present invention relates to Compound 73 or its pharmaceutically acceptable salt for treating a respiratory disorder, such as asthma or COPD by reducing eosinophil or neutrophil count and/or increasing FEV1, in a subject by administering an effective amount of Compound 73 or its pharmaceutically acceptable salt by inhalation route, wherein inhibition of human TRPA1 receptor activity is the principal therapeutic mode of action of Compound 73 or its pharmaceutically acceptable salt.

In yet another specific embodiment, the present invention relates to Compound 84 or its pharmaceutically acceptable salt for treating a respiratory disorder, such as asthma or COPD by reducing eosinophil or neutrophil count and/or increasing FEV1, in a subject by administering an effective amount of Compound 84 or its pharmaceutically acceptable salt by inhalation route, wherein inhibition of human TRPA1 receptor activity is the principal therapeutic mode of action of Compound 84 or its pharmaceutically acceptable salt.

In another specific embodiment, the present invention relates to Compound 90 or its pharmaceutically acceptable salt for treating a respiratory disorder, such as asthma or COPD by reducing eosinophil or neutrophil count and/or increasing FEV1, in a subject by administering an effective amount of Compound 90 or its pharmaceutically acceptable salt by inhalation route, wherein inhibition of human TRPA1 receptor activity is the principal therapeutic mode of action of Compound 90 or its pharmaceutically acceptable salt.

In a further specific embodiment, the present invention relates to Compound 92 or its pharmaceutically acceptable salt for treating a respiratory disorder, such as asthma or COPD by reducing eosinophil or neutrophil count and/or increasing FEV1, in a subject by administering an effective amount of Compound 92 or its pharmaceutically acceptable salt by inhalation route, wherein inhibition of human TRPA1 receptor activity is the principal therapeutic mode of action of Compound 92 or its pharmaceutically acceptable salt.

In an embodiment, the present invention relates to a TRPA1 antagonist which has an $IC_{50}$ for inhibiting human TRPA1 receptor activity of less than 2 micromolar or preferably less than 1 micromolar, or even more preferably less than 500 nanomolar for the treating a respiratory disorder, such as asthma or COPD by reducing eosinophil or neutrophil count and/or increasing FEV1, in a subject by administering an effective amount of the TRPA1 antagonist by inhalation route, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar for the treating a respiratory disorder, such as asthma or COPD by reducing eosinophil or neutrophil count and/or increasing FEV1, in a subject by administering an effective amount of the TRPA1 antagonist by inhalation route, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar for the treating a respiratory disorder, such as asthma or COPD by reducing eosinophil or neutrophil count and/or increasing FEV1, in a subject by administering an effective amount of the TRPA1 antagonist by inhalation route, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar for the treating a respiratory disorder, such as asthma or COPD by reducing eosinophil or neutrophil count and/or increasing FEV1, in a subject by administering an effective amount of the TRPA1 antagonist by inhalation route, wherein the TRPA1 antagonist has an $IC_{50}$ for inhibiting human TRPM8 receptor activity greater than at least 10 times the $IC_{50}$ for inhibiting human TRPA1 receptor activity.

The present invention, in an embodiment, also provides use of an effective amount of TRPA1 antagonists which are amides of 4-aryl-2-amino-thiazole compounds, wherein aryl may be substituted or unsubstituted phenyl in the manufacture of a composition for inhalation administration for reducing eosinophil or neutrophil count and/or increasing FEV1 in the treatment of a respiratory disorder in a subject.

The present invention, in an embodiment, also provides use of an effective amount of a TRPA1 antagonist of formulae:

(A) or (B) or (C) or (D)

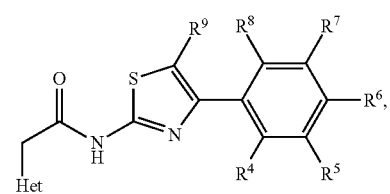
(A)

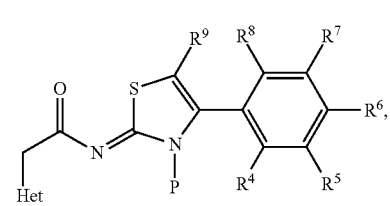
(B)

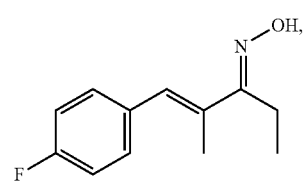
(C)

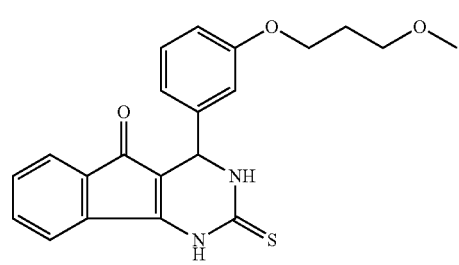
(D)

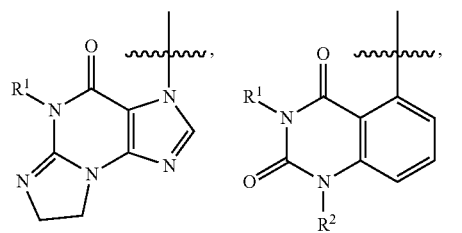

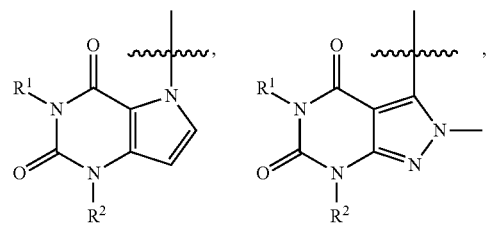

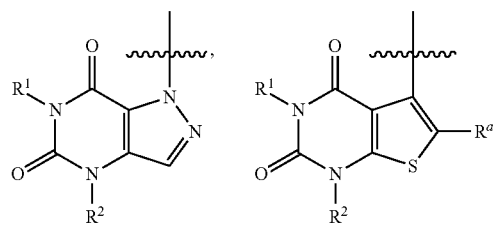

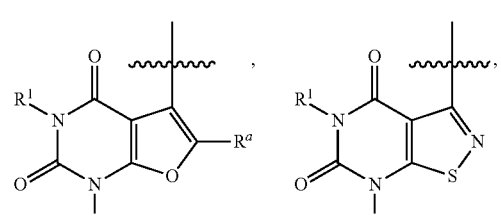

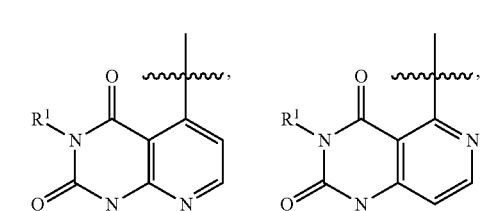

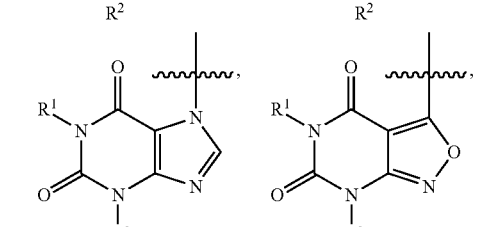

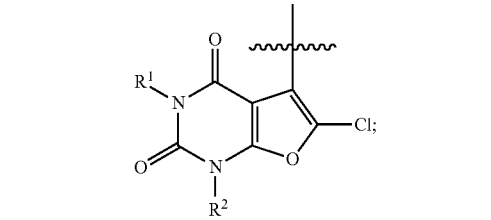

or a pharmaceutically-acceptable salt thereof, wherein, 'Het' is selected from the group consisting of P is selected from

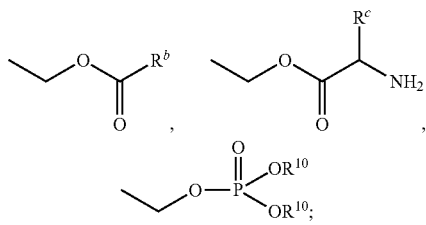

R¹, R² and Rᵃ, which may be the same or different, are each independently hydrogen or $(C_1-C_4)$alkyl;

Rᵇ and Rᶜ independently selected from hydrogen, substituted or unsubstituted alkyl arylalkyl, amino acid and heterocyclic ring;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl;

R¹⁰ is selected from hydrogen, alkyl, arylalkyl and pharmaceutically acceptable cation, in the manufacture of a composition for inhalation administration for reducing eosinophil or neutrophil count and/or increasing FEV1 in the treatment of a respiratory disorder in a subject.

The present invention, in an embodiment, also provides use of an effective amount of a TRPA1 antagonist of formulae (XII) or (D)

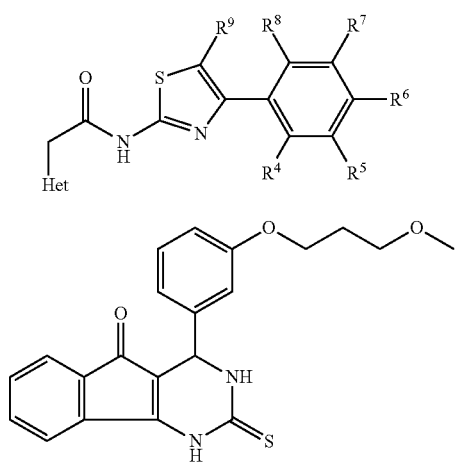

or a pharmaceutically-acceptable salt thereof, wherein, 'Het' is selected from the group consisting of

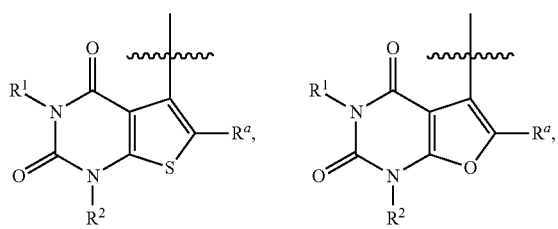

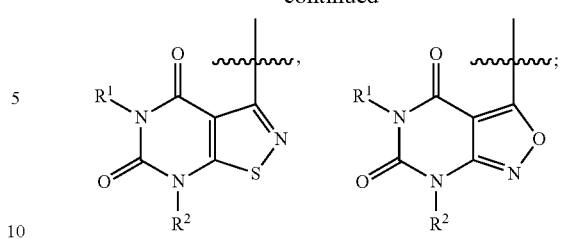

R¹, R² and Rᵃ, which may be the same or different, are each independently hydrogen or $(C_1-C_4)$alkyl;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl, in the manufacture of a composition for inhalation administration for reducing eosinophil or neutrophil count and/or increasing FEV1 in the treatment of a respiratory disorder in a subject.

The present invention, in an embodiment, also provides use of an effective amount of a TRPA1 antagonist, which is

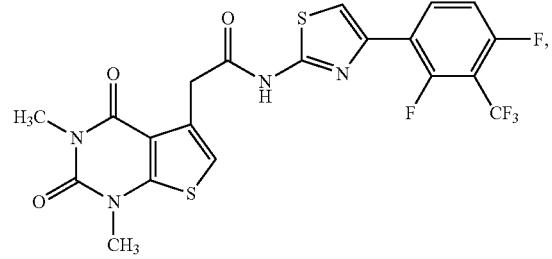

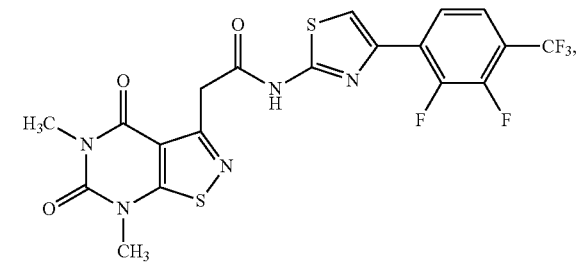

-continued

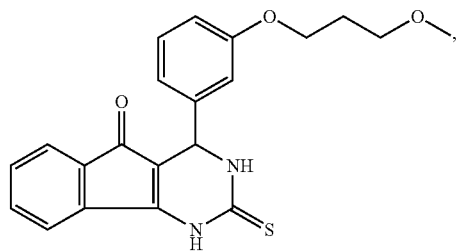
(Compound 90)

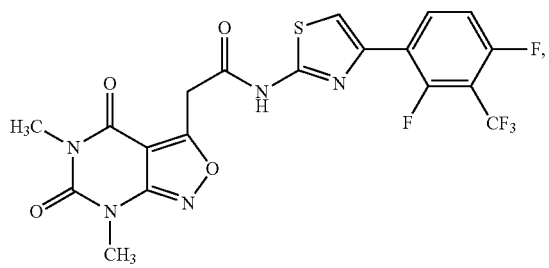
(Compound 92)

or a pharmaceutically acceptable salt thereof, in the manufacture of a composition for inhalation administration for reducing eosinophil or neutrophil count and/or increasing FEV1 in the treatment of a respiratory disorder in a subject.

The present invention, in an embodiment, also provides use of an effective amount of a TRPA1 antagonist which has an $IC_{50}$ for inhibiting human TRPA1 receptor activity of less than 2 micromolar or preferably less than 1 micromolar, in the manufacture of a composition for inhalation administration for reducing eosinophil or neutrophil count and/or increasing FEV1 in the treatment of a respiratory disorder in a subject. Preferably, the TRPA1 antagonist has an $IC_{50}$ for inhibiting human TRPA1 receptor activity of less than 700 nanomolar, or more preferably, less than 500 nanomolar.

Specifically, the TRPA1 antagonist may be selected from Compound 52, Compound 73, Compound 84, Compound 90, Compound 92 or a pharmaceutically acceptable salt thereof.

In another embodiment, the present invention provides use of an effective amount of a TRPA1 antagonist which has an $IC_{50}$ for inhibiting human TRPA1 receptor activity of less than 2 micromolar in the manufacture of a composition for inhalation administration for reducing eosinophil or neutrophil count and/or increasing FEV1 in the treatment of a respiratory disorder in a subject, wherein such inhibition of human TRPA1 receptor activity is the principal therapeutic mode of action of the TRPA1 antagonist. It is contemplated that inhibition of human TRPA1 receptor activity is principal but not exclusive mode of action of the TRPA1 antagonist.

In an embodiment, the present invention relates to use of an effective amount of a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of a TRPA1 antagonist which has an $IC_{50}$ for inhibiting human TRPA1 receptor activity of less 2 micromolar or less than 1 micromolar, preferably less than 700 nanomolar, or even more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of a TRPA1 antagonist which has an $IC_{50}$ for inhibiting human TRPA1 receptor activity of less than 2 micromolar or less than 1 micromolar, or preferably less than 700 nanomolar, or even more preferably less than 500 nanomolar in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

Specifically, In an embodiment, the present invention relates to use of an effective amount of Compound 52 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of Compound 52 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of Compound 52 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of Compound 52 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

Specifically, In an embodiment, the present invention relates to use of an effective amount of Compound 73 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of Compound 73 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of Compound 73 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of Compound 73 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

Specifically, In an embodiment, the present invention relates to use of an effective amount of Compound 84 or its pharmaceutically acceptable salt in the manufacture of a composition for reducing eosinophil or neutrophil count and/or increasing FEV1 in inhalation administration for the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of Compound 84 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of Compound 84 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of Compound 84 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

Specifically, In an embodiment, the present invention relates to use of an effective amount of Compound 90 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of Compound 90 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of Compound 90 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of Compound 90 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

Specifically, In an embodiment, the present invention relates to use of an effective amount of Compound 92 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of Compound 92 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of Compound 92 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of Compound 92 or its pharmaceutically acceptable salt in the manufacture of a composition for inhalation administration for reducing eosinophil or neutrophil count and/or increasing FEV1 in the treatment of a respiratory disorder, such as asthma or COPD, in a subject, wherein the TRPA1 antagonist has an $IC_{50}$ for inhibiting human TRPM8 receptor activity greater than at least 10 times the $IC_{50}$ for inhibiting human TRPA1 receptor activity.

In an embodiment, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar or more preferably less than 500 nanomolar in the manufacture of a composition for inhalation administration for reducing eosinophil or neutrophil count and/or increasing FEV1 in the treatment of a respiratory disorder by reducing the eosinophil or neutrophil count and/or airway hyper-reactivity/responsiveness in a subject, wherein the TRPA1 antagonist has an $IC_{50}$ for inhibiting human TRPV1 receptor activity greater than at least 10 times the $IC_{50}$ for inhibiting human TRPA1 receptor activity.

In another embodiment, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar or more preferably less than 500 nanomolar in the manufacture of a composition for inhalation administration for the treatment of a respiratory disorder by reducing the eosinophil or neutrophil count and/or airway hyper-reactivity/responsiveness in a subject, wherein the TRPA1 antagonist has an $IC_{50}$ for inhibiting human TRPV3 receptor activity greater than at least 10 times the $IC_{50}$ for inhibiting human TRPA1 receptor activity.

In yet another embodiment, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar or more preferably less than 500 nanomolar in the manufacture of a composition for inhalation administration for the treatment of a respiratory disorder by reducing the eosinophil or neutrophil count and/or airway hyper-reactivity/responsiveness in a subject, wherein the TRPA1 antagonist has an $IC_{50}$ for inhibiting human TRPV4 receptor activity greater than at least 10 times the $IC_{50}$ for inhibiting human TRPA1 receptor activity.

In a further embodiment, the present invention relates to use of an effective amount of a TRPA1 antagonist which has an $IC_{50}$ for inhibiting human TRPA1 receptor activity of less than 2 micromolar or less than 1 micromolar or preferably less than 700 nanomolar or more preferably less than 500 nanomolar in the manufacture of a composition for inhalation administration for the treatment of a respiratory disorder by reducing the eosinophil or neutrophil count and/or airway hyper-reactivity/responsiveness in a subject, wherein the TRPA1 antagonist has an $IC_{50}$ for inhibiting human TRPM8 receptor activity greater than at least 10 times the $IC_{50}$ for inhibiting human TRPA1 receptor activity.

In another embodiment, the present invention provides a TRPA1 antagonist which has an $IC_{50}$ for inhibiting human TRPA1 receptor activity of less than 2 micromolar or less than 1 micromolar, or less than 700 nanomolar, for reducing eosinophil or neutrophil count and/or increasing FEV1 in the treatment of a respiratory disorder in a subject, wherein an effective amount of the TRPA1 antagonist is administered to the subject by inhalation route.

In another embodiment, the present invention provides a method of treating a respiratory disorder by reducing eosinophil or neutrophil count and increasing FEV1 in a subject, said method comprising administering a TRPA1 antagonist that has an $IC_{50}$ for inhibiting human TRPV1, TRPV3, TRPV4 and TRPM8 receptor activity greater than at least 10 times the $IC_{50}$ for inhibiting human TRPA1 receptor activity.

In another embodiment, the present invention provides a method of reducing eosinophil or neutrophil count and/or increasing FEV1 in a subject having a respiratory disorder, said method comprising administering to the subject by inhalation route an effective amount of TRPA1 antagonists which are amides of 4-aryl-2-amino-thiazole compounds, wherein aryl may be substituted or unsubstituted phenyl.

In another embodiment, the present invention provides a pharmaceutical composition for inhalation administration comprising a TRPA1 antagonist that has an $IC_{50}$ for inhibiting human TRPA1 receptor activity of less than 2 micromolar for reducing eosinophil or neutrophil count in a subject having a respiratory disorder.

Pharmaceutical Compositions

The present invention also provides pharmaceutical compositions for inhalation administration comprising a TRPA1 antagonist which has an $IC_{50}$ for inhibiting human TRPA1 receptor activity of less than 2 micromolar or preferably less than 1 micromolar, or even more preferably less than 500 nanomolar. The pharmaceutical compositions suitable for administration by inhalation route typically include dry powder inhaler (DPI) formulations, metered dose inhaler (MDI) formulations, nasal sprays, insufflations, and formulations suitable for nebulization. Preferably, the pharmaceutical composition is a DPI or MDI formulation.

The composition may be in the form of pressurized metered dose inhaler, a dry powder inhaler, a nasal spray or a solution/suspension for nebulization. The inhalation delivery device may be a single dose/unit dose type or reservoir type. The inhalation composition may be administered by oral route or nasal route or both.

In a further aspect of the present invention, the pharmaceutical composition may comprise pharmaceutically acceptable excipients in addition to the TRPA1 antagonist.

As set forth above, the pharmaceutical composition includes at least one pharmaceutically acceptable excipient, which includes but is not limited to one or more of the following; diluents, glidants and lubricants, preservatives, buffering agents, chelating agents, polymers, surfactants, propellants, solvents and the like.

It will be understood that various modifications may be made to the embodiments disclosed herein. Therefore the above description should not be construed as limiting, but merely as exemplifications of preferred embodiments.

The following examples are provided to enable one skilled in the art to practice the invention and are merely illustrative of the invention. The examples should not be read as limiting the scope of the invention.

EXAMPLES

Example 1

Determination of $IC_{50}$ and Selectivity of Exemplary TRPA1 Antagonists of the Present Invention

Protocol

The illustrative TRPA1 antagonists of the present invention were screened for TRPA1 activity according to a modified procedure described in Tóth, A. et al., Life Sciences 2003, 73, 487-498. The screening of the compounds can be carried out by other methods and procedures known to persons skilled in the art.

Screening for TRPA1 Antagonist Using the 45Calcium Uptake Assay:

The inhibition of TRPA1 receptor activation was measured as inhibition of allylisothiocyanate (AITC) induced cellular uptake of radioactive calcium. Test compounds were dissolved in DMSO to prepare 10 mM stock solution and then diluted using plain medium with 0.1% BSA and 1.8 mM $CaCl_2$ to get desired concentration. Final concentration of DMSO in the reaction was 0.5% (v/v). Human TRPA1 expressing CHO cells were grown in F-12 DMEM medium with 10% FBS, 1% penicillin-streptomycin solution, and 400 µg/ml of G-418. Cells were seeded 24 h prior to the assay in 96 well plates so as to get ~50,000 cells per well on the day of experiment. Cells were treated with test compounds for 10 min followed by addition of AITC at a final concentration of 30 micromolar and 5 µCi/ml 45Ca+2 for 3 min at 25° C. Cells were washed and lysed using buffer containing 1% Triton X-100, 0.1% deoxycholate and 0.1% SDS. Radioactivity in the lysate was measured in Packard Top count after addition of liquid scintillant.

Concentration response curves were plotted as a % of maximal response obtained in the absence of test antagonist. $IC_{50}$ value was calculated from concentration response curve by nonlinear regression analysis using GraphPad PRISM software.

For selectivity screening, CHO cells stably expressing human TRPV1, human TRPV3, human TRPV4, or human TRPM8 were generated in-house and maintained in DMEM F-12 supplemented with 10% FBS and G418. All the cell types were cultured at 37° C. in humidified air containing 5% CO2. Radiometric calcium assay was performed as described above with some minor modifications. Assay was carried out in total volume of 200 µl at 30° C. (for TRPV1), 32° C. (for TRPV3) and 25° C. (for TRPV4 and TRPM8). Agonists used for selectivity screening of the different TRPs are: Capsaicin for TRPV1, 2-aminoethoxydiphenyl borate for TRPV3, 4α-phorbol 12,13-didecanoate for TRPV4 and Icilin for TRPM8. After 2-5 minutes of agonist treatment, drug was washed and lysed in lysis buffer as mentioned above. Radioactivity in the lysate was measured in Packard Top count after addition of liquid scintillant.

TABLE 1

TRPA1 antagonists which has an $IC_{50}$ for inhibiting human TRPA1 receptor activity of less than 2 micromolar, and selectivity over human TRPV1, human TRPV3, human TRPV4 and human TRPM8 receptors.

| Compound No | $IC_{50}$ values | | | | |
|---|---|---|---|---|---|
| | hTRPA1 | hTRPV1 | hTRPV3 | hTRPV4 | hTRPM8 |
| 1 | 920.9 nM | >10 µM | >10 µM | >10 µM | >10 µM |
| 2 | 381.8 nM | >10 µM | >10 µM | 3.84 µM | >10 µM |
| 3 | 73.35 nM | >10 µM | >10 µM | 969.3 nM | >10 µM |
| 4 | 98.32 nM | >10 µM | >10 µM | >1 µM | >10 µM |
| 5 | 66.28 nM | >10 µM | >10 µM | >1 µM | >10 µM |
| 6 | 97.42 nM | >10 µM | >10 µM | >1 µM | >10 µM |
| 7 | 47.37 nM | >10 µM | 2.1 µM (P) | 1.87 µM | >10 µM |
| 8 | 55.02 nM | >10 µM | >10 µM | >1 µM | >10 µM |
| 9 | 102.5 nM | >10 µM | >1 µM | >1 µM | >10 µM |
| 10 | 46.74 nM | >10 µM | >10 µM | >10 µM | >10 µM |
| 11 | 46.27 nM | >10 µM | >10 µM | 1.5 µM | >10 µM |
| 12 | 51.68 nM | >10 µM | >10 µM | >1 µM | >10 µM |
| 13 | 48.21 nM | >10 µM | >1 µM | 2.8 µM | >10 µM |
| 14 | 60.42 nM | >10 µM | >1 µM | >1 µM | >10 µM |
| 15 | 53.57 nM | >10 µM | >1 µM | >1 µM | >10 µM |
| 16 | 58.94 nM | >10 µM | >10 µM | >10 µM | >10 µM |
| 17 | 56.02 nM | >10 µM | >10 µM | >1 µM | >10 µM |
| 18 | 13.38 nM | >10 µM | >10 µM | 1.32 µM | >10 µM |
| 19 | 26.13 nM | >10 µM | >1 µM | 1.63 µM | >10 µM |
| 20 | 20.09 nM | >10 µM | >1 µM | 1.67 µM | >10 µM |
| 21 | 48.18 nM | >1 µM | >10 µM | 520.2 nM | >10 µM |
| 22 | 79.77 nM | >10 µM | >10 µM | >1 µM | >10 µM |
| 23 | 43.93 nM | >10 µM | >10 µM | >1 µM | >10 µM |
| 24 | 138.1 nM | >10 µM | >1 µM | >10 µM | >10 µM |
| 25 | 58.55 nM | >10 µM | >1 µM | >1 µM | >10 µM |
| 26 | 47.91 nM | >10 µM | >1 µM | >1 µM | >10 µM |
| 27 | 65.45 nM | >10 µM | >10 µM | >10 µM | >10 µM |
| 28 | 6.49 nM | >10 µM | >1 µM | 902.6 nM | >10 µM |
| 29 | 11.38 nM | >10 µM | >1 µM | >10 µM | >10 µM |
| 30 | 34.03 nM | >10 µM | >10 µM | >10 µM | >10 µM |
| 31 | 17.3 nM | >10 µM | >10 µM | >10 µM | >10 µM |
| 32 | 5.96 nM | >10 µM | >10 µM | >1 µM | >10 µM |
| 33 | 5.37 nM | >10 µM | >10 µM | <1 µM | >10 µM |
| 34 | 38.46 nM | >10 µM | >10 µM | >10 µM | >10 µM |
| 35 | 18.05 nM | >10 µM | >10 µM | >10 µM | >10 µM |
| 36 | 49.92 nM | >10 µM | >10 µM | >10 µM | >10 µM |

TABLE 1-continued

TRPA1 antagonists which has an IC$_{50}$ for inhibiting human TRPA1
receptor activity of less than 2 micromolar, and selectivity over human TRPV1,
human TRPV3, human TRPV4 and human TRPM8 receptors.

| Compound No | IC$_{50}$ values | | | | |
|---|---|---|---|---|---|
| | hTRPA1 | hTRPV1 | hTRPV3 | hTRPV4 | hTRPM8 |
| 37 | 12.26 nM | >10 μM | >10 μM | >10 μM | >10 μM |
| 38 | 15.92 nM | >10 μM | >10 μM | >1 μM | >10 μM |
| 39 | 26.56 nM | >10 μM | >10 μM | >1 μM | >10 μM |
| 40 | 22.82 nM | >10 μM | >10 μM | >10 μM | >10 μM |
| 41 | 11.04 nM | >10 μM | >10 μM | >1 μM | >10 μM |
| 42 | 11.38 nM | >10 μM | >10 μM | >10 μM | >10 μM |
| 43 | 18.37 nM | >10 μM | >10 μM | >1 μM | >10 μM |
| 44 | 8.36 nM | >10 μM | >10 μM | >10 μM | >10 μM |
| 45 | 26.39 nM | >10 μM | >1 μM | >1 μM | >10 μM |
| 46 | 41.31 nM | >10 μM | >10 μM | >10 μM | >1 μM |
| 47 | 33.61 nM | >10 μM | >10 μM | >1 μM | >10 μM |
| 48 | 18.12 nM | >10 μM | >10 μM | >10 μM | >10 μM |
| 49 | 3.98 nM | >10 μM | >10 μM | >10 μM | >10 μM |
| 50 | 16.73 nM | >10 μM | >1 μM | 8.89 μM | >10 μM |
| 51 | 4.84 nM | >10 μM | >10 μM | 4.57 μM | >10 μM |
| 52 | 2.49 nM | >10 μM | 2.52 μM | 3.04 μM | >10 μM |
| 53 | 18.20 nM | >10 μM | >10 μM | >1 μM | >10 μM |
| 54 | 17.74 nM | >10 μM | >1 μM | >1 μM | >10 μM |
| 55 | 2.15 nM | >10 μM | >1 μM | >1 μM | >10 μM |
| 56 | 3.38 nM | >10 μM | >10 μM | >1 μM | >10 μM |
| 57 | 1.45 nM | >10 μM | >10 μM | >1 μM | >10 μM |
| 58 | 11.88 nM | >10 μM | >1 μM | >1 μM | >10 μM |
| 59 | 2.21 nM | >10 μM | >1 μM | 2.83 μM (P) | >10 μM |
| 60 | 3.54 nM | >10 μM | >10 μM | >1 μM | >10 μM |
| 61 | 2.93 nM | >10 μM | >10 μM | >10 μM | >10 μM |
| 62 | 1.68 nM | >10 μM | >10 μM | >1 μM | >10 μM |
| 63 | 9.04 nM | >10 μM | >1 μM | >10 μM | >10 μM |
| 64 | 4.52 nM | >10 μM | >1 μM | >10 μM | >10 μM |
| 65 | 6.65 nM | >10 μM | >1 μM | >1 μM | >10 μM |
| 66 | 3.63 nM | >10 μM | >10 μM | >10 μM | >10 μM |
| 67 | 13.59 nM | >10 μM | >1 μM | >10 μM | >10 μM |
| 68 | 4.84 nM | >10 μM | >1 μM | >10 μM | >10 μM |
| 69 | 7.10 nM | >10 μM | >1 μM | >1 μM | >10 μM |
| 70 | 12.57 nM | >10 μM | >1 μM | >1 μM | >10 μM |
| 71 | 3.18 nM | >10 μM | >1 μM | >10 μM | >10 μM |
| 72 | 4.16 nM | >10 μM | >1 μM | >1 μM | >10 μM |
| 73 | 8.54 nM | >10 μM | 4.45 μM | 5.74 μM | >10 μM |
| 74 | 5.29 nM | >10 μM | >10 μM | >10 μM | >10 μM |
| 75 | 3.34 nM | >10 μM | >10 μM | >10 μM | >10 μM |
| 76 | 4.02 nM | 8.01 μM | 2.50 μM | 8.92 μM (P) | >10 μM |
| 77 | 5.60 nM | >10 μM | 1.77 μM | 553.1 nM | >10 μM |
| 78 | 10.57 nM | >10 μM | >1 μM | 152.9 nM | >10 μM |
| 79 | 5.29 nM | >10 μM | >1 μM | 825.8 nM | >10 μM |
| 80 | 6.28 nM | >10 μM | >10 μM | 278.7 nM | >10 μM |
| 81 | 6.74 nM | >10 μM | >1 μM | 161.7 nM | >10 μM |
| 82 | 8.04 nM | >10 μM | >1 μM | 172.0 nM | >10 μM |
| 83 | 4.40 nM | >10 μM | >1 μM | 236.5 nM | >10 μM |
| 84 | 5.35 nM | 17.66 μM | 2.83 μM | 131.9 nM | >10 μM |
| 85 | 8.92 nM | >10 μM | >1 μM | 619.5 nM | >10 μM |
| 86 | 6.91 nM | >10 μM | >10 μM | >1 μM | >10 μM |
| 87 | 19.32 nM | >10 μM | >10 μM | 2.01 μM | >10 μM |
| 88 | 11.45 nM | >10 μM | >1 μM | 158.4 nM | >10 μM |
| 89 | 98.44 nM | >10 μM | >10 μM | >10 μM | >10 μM |
| 90 | 5.61 nM | >10 μM | >10 μM | >10 μM | >10 μM |
| 91 | 451.4 nM | >10 μM | >10 μM | >10 μM | >10 μM |
| 92 | 17.08 nM | >10 μM | >1 μM | >1 μM | >10 μM |
| 93 | 1180.0 nM | >10 μM | >10 μM | >10 μM | >10 μM |
| 94 | 1580.0 nM | >10 μM | >10 μM | >10 μM | >10 μM |
| 95 | 88.50 nM | >10 μM | 2.81 μM | 2.35 μM | >10 μM |
| 96 | 559.3 nM | — | — | — | — |
| 97 | 21.91 nM | — | — | — | — |
| 98 | 54.29 nM | — | — | — | — |
| 99 | 5.06 nM | — | — | 1.47 μM | — |
| 100 | 5.15 nM | — | — | >10 μM | — |
| 101 | 10.10 nM | — | — | >1 μM | — |
| 102 | 7.67 nM | — | — | 1.35 μM | — |
| 103 | 27.41 nM | — | — | 4.02 μM | — |
| 104 | 7.58 nM | — | — | 1.81 μM | — |

Example 2

Efficacy Study of a TRPA1 Antagonist when Administered by Intra-Tracheal (i.t.) Route in Guinea Pigs Healthy male Dunkin Hartley guinea pigs weighing between 300-400 gm were sensitized on day 0 with (5 mg) and on day 2 with (10 mg) of ovalbumin (Ova) and 10 mg of aluminum hydroxide gel given intra peritoneal (i.p.). Guinea pigs were challenged with 0.3% aerosolized ovalbumin on Day 21 following sensitization.

Actively sensitized male guinea pigs with free access to water, were fasted overnight, and used for the studies. Animals were assigned to one of the following groups during each experiment as per Table 2 below.

TABLE 2

Animal grouping in Example 2.

| Groups | Group Code* | Compound/Lactose (Dose, μg/animal.) i.t. | Ova Challenge |
|---|---|---|---|
| A | Saline + Lactose powder (Saline) | 2 mg/animal, i.t. | + |
| B | Ova + Lactose powder (Ova) | 2 mg/animal, i.t. | + |
| C | Ova + Compound 52 | 25 | + |
| D | Ova + Compound 52 | 50 | + |
| E | Ova + Compound 52 | 125 | + |
| F | Ova + Compound 52 | 250 | + |
| G | Ova + Compound 52 | 500 | + |

Guinea pigs were dosed intra-tracheally with Compound 52 or vehicle 4 hours before exposure to aerosolized ovalbumin challenge. The control group of animals received vehicle (Lactose powder—2 mg/animal, i.t.) only.

Broncho Alveolar Lavage (BAL) was performed at 48 hours after challenge with ovalbumin. Animals were anesthetized with an overdose of urethane, trachea was exposed and BAL was performed 5 times using 5 mL PBS. All aspirates of BAL were pooled and total number of cells determined using a hemocytometer. The BAL was centrifuged, and the cell pellet re-suspended in 50 μL guinea pig serum and used for preparation of smears. Slides were stained with Giemsa stain and a differential cell count of 500 cells based on standard morphology was performed manually.

Calculations

The total number of eosinophils in each BAL sample was calculated using the formula:

$$\text{Total No. of eosinophils (in } BAL) = \frac{(\text{Total cell count} \times 10^5/\text{mL} \times \text{Percent eosinophils})}{100}$$

Percent inhibition of eosinophils was calculated using the following formula:

$$\% \text{ Inhibition of eosinophils} = \frac{100 \ [\text{Avg. eosinophils}_{(Ova)} - \text{eosinophils}_{(Compound)}]}{[\text{Avg. eosinophils}_{(Ova)} - \text{Avg. eosinophils}_{(Saline)}]} \times 100$$

The results for the bronchoconstriction part were calculated as percent (%) change in sGaw from saline base-line readings with saline taken just 1 minute before the antigen challenge and reported as peak change (mean±S.E.M.) for every 5 minutes for a total duration of 30 min after OA challenge. Area under the curve (AUC) was determined for each animal using GraphPad Prism. The percent (%) increase in AUC in the treated group relative to the vehicle group was calculated. Data was statistically analyzed using ANOVA and Dunnett's post hoc test.

Figure 2:
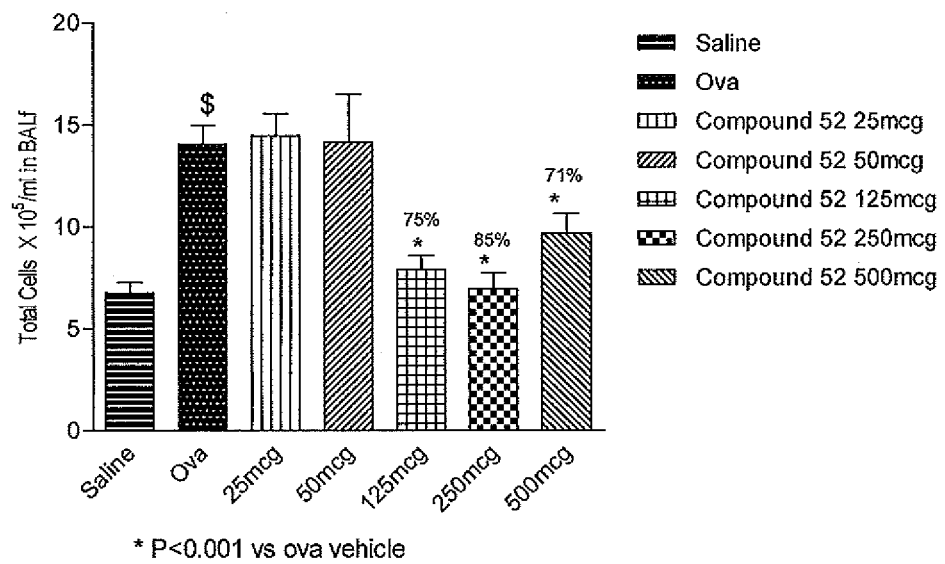
FIG. 2 is a bar graph that represents the effect of Compound 52 on total cell count in ovalbumin induced asthma model in guinea pigs.
Figure 3:
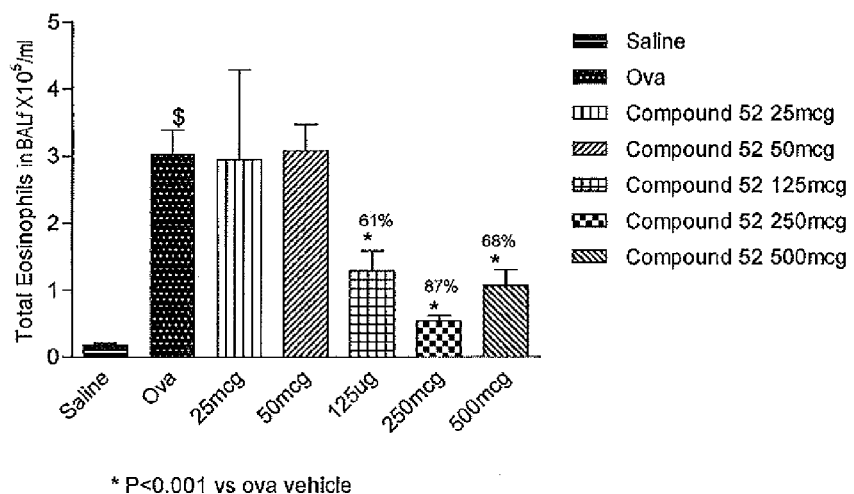
FIG. 3 is a bar graph that represents the effect of Compound 52 on eosinophil count in ovalbumin induced asthma model in guinea pigs.

Results:

Significant decrease in lung compliance and increase in bronchoconstriction was observed in vehicle treated animals compared to Saline treated animals (FIG. 1) upon antigen challenge. Compound 52 (single dose, i.t., 4 hour pretreatment) treatment prevented antigen induced bronchoconstriction. There was significant increase in the eosinophils in the bronchoalveolar lavage fluid ("BALF") of the vehicle treated animals compared to the saline exposed animals. Eosinophil is a major cell type in the BALF of animals recovered from vehicle treated group. Compound 52 had significant effect on the total cell count in ovalbumin induced asthma model in guinea pigs (FIG. 2). Further, there was a significant inhibition of eosinophils (75%) (61%, 87% and 68% at 125, 250 and 500 μg/animal dosing respectively) in Compound 52 treated animals also showed as shown in Table 3 and in FIG. 3.

TABLE 3

Effect of compound 52 when administered by intra-tracheal (i.t.) route in guinea pigs.

| Treatment | Dose (μg/kg) | Airway conductance sGAW (AUC) | Percent improvement in airway conductance | Percent inhibition of eosinophils |
|---|---|---|---|---|
| Saline | — | 2639 | | |
| Ova | — | 1495 | | |
| Ova + Compound 52 | 25 | 1399 | 0 | 0 |
| Ova + Compound 52 | 50 | 1592 | 7 | 0 |
| Ova + Compound 52 | 125 | 1943 | 39 | 61 |
| Ova + Compound 52 | 250 | 2004 | 45 | 87 |
| Ova + Compound 52 | 500 | 1987 | 43 | 68 |

Conclusion

Results of this study show that intra-tracheal (i.t.) administration of Compound 52 at 125, 250 and 500 μg/animal significantly inhibits antigen induced bronchoconstriction as well as pulmonary eosinophilia.

Example 3

Efficacy Study of a TRPA1 Antagonist when Administered by Intra-Tracheal (i.t.) Route in Brown Norway (BN) Rats Male Brown Norway rats were sensitized subcutaneously on day 0, 14 and 21 with 0.5 ml solution containing 20 μg/ml ovalbumin and 40 mg/ml aluminum hydroxide. Simultaneously animals were injected intraperitoneally (i.p.) with 0.25 ml of *B. pertussis* vaccine/rat containing $4 \times 10^8$ heat killed bacilli/ml. Rats were challenged with 1% aerosolized ovalbumin on Day 28 following sensitization. Animals were assigned to one of the following 5 groups during each experiment as given below in Table 4.

TABLE 4

Animal grouping in Example 3.

| Group | Group Code | Dose | Ova Challenge |
|---|---|---|---|
| A | Saline Vehicle | 100 μl/animal i.t. | − |
| B | Ova Vehicle | 100 μl/animal i.t. | + |
| C | Compound 52 | 100 μg/animal i.t. | + |
| D | Compound 52 | 250 μg/animal i.t. | + |
| E | Compound 52 | 500 μg/animal i.t. | + |

Test compounds were triturated and volume was made up with Normal Saline (0.9% NaCl). Animals were administered Compound 52 intra-tracheally 1 hour before ovalbumin challenge. Animals were sacrificed 48 hours after ovalbumin challenge and BAL was performed as mentioned in Example 2. The pooled BAL was used to determined total number of cells using a hemocytometer. Further, cell differential study was performed according to Example 2.

The total number of eosinophils in each BAL sample was calculated using the formula:

$$\text{Total No. of eosinophils (in } BAL) = \frac{(\text{Total cell count} \times 10^5 / \text{mL} \times \text{Percent eosinophils})}{100}$$

Percent inhibition of eosinophils was calculated using the following formula:

$$\% \text{ Inhibition of eosinophils} = \frac{100 \, [\text{Avg. } eosinophils_{(Ova\ Vehicle)} - eosinophils_{(Compound)}]}{[\text{Avg. } eosinophils_{(Ova\ Vehicle)} - \text{Avg. } eosinophils_{(Saline\ Vehicle)}]} \times 100$$

The data was statistically evaluated by ANOVA followed by Dunnett's multiple comparisons test.

In the ovalbumin challenged-vehicle (Ova Vehicle) treated animals, significant increase in the inflammation (based on total cells and total eosinophil count) was observed compared to saline controls (Saline Vehicle). Compound 52 significantly inhibited the total cells and eosinophils in a dose dependent manner as shown in FIGS. 4 and 5.

Conclusion

Figure 4:
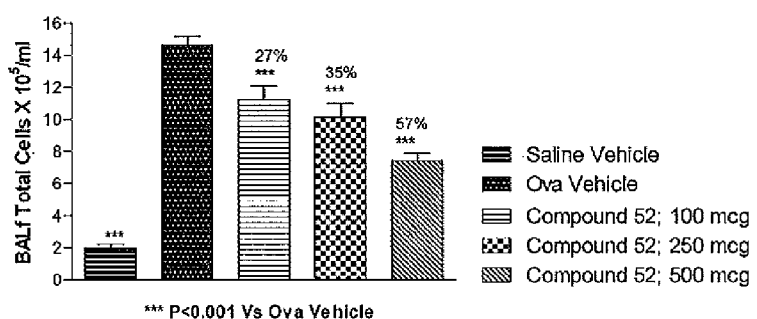
FIG. 4 is a bar graph that represents the effect of Compound 52 treatment on total cell count in BALF.
Figure 5:
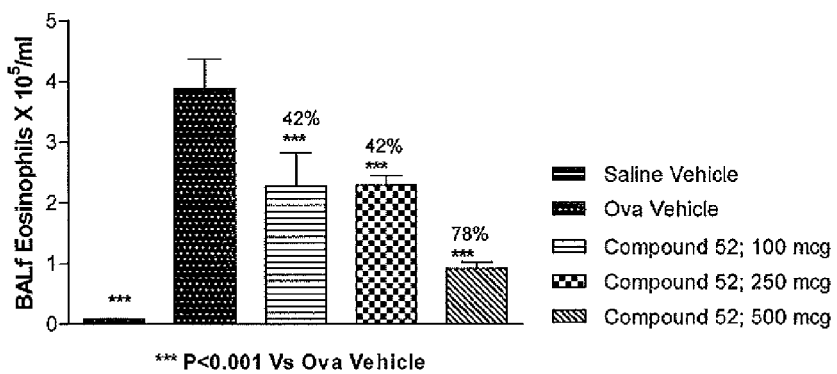
FIG. 5 is a bar graph that represents the effect of Compound 52 treatment on eosinophil count in BALF.

Compound 52 significantly inhibited the total cells (Leukocytes) in a dose dependent manner (FIG. 4). Compound 52 also showed significant and dose dependent inhibition of pulmonary eosinophilia with an $ED_{50}$ of 213 mcg i.t. (FIG. 5).

Example 4

Pharmacokinetic Data of Compound 52 in Guinea Pig Model Upon Intra-Tracheal Administration of 500 mcg Dose Guinea pigs were dosed intra-tracheally with Compound 52 with lactose as a vehicle. At various time points, animals were sacrificed with an overdose of urethane, trachea was exposed and BAL was performed 5 times using 5 mL PBS. Lung tissue was collected and kept at −70° C. until analysis. The BAL was centrifuged, and the cell pellet was collected and kept at −70° C. until analysis. The pharmacokinetic parameters of Compound 52 in Guinea pigs are given in Table 5.

TABLE 5

Pharmacokinetic data of Compound 52 in Guinea pig model

| Organ | *Cmax (ng/ml or g) | $AUC_{0-24}$ (ng · h/ml or g) | Tmax (h) |
|---|---|---|---|
| Lung Tissue | 4989 ± 2548 | 103786 ± 28285 | 8 |
| Cell Pellet | 6726 ± 2049 | 70390 ± 12071 | 0.25 |

*The numbers are mean ± SD (N = 3)

Example 5

Efficacy Study of a TRPA1 Antagonist in Brown Norway (BN) Rats

Male BN rats were sensitized subcutaneously (s.c.) on day 0, 14 and 21 with 0.5 ml solution containing 20 μg/ml ovalbumin (Ova) and 40 mg/ml aluminum hydroxide. Simultaneously the animals were injected intraperitoneally (i.p.) with 0.25 ml of *B. pertussis* vaccine/rat containing $4 \times 10^8$ heat killed bacilli/ml. The rats were challenged with 1% aerosolized ovalbumin on Day 28 following sensitization. The Animals were assigned to one of the following 7 groups during each experiment as given in Table 6.

TABLE 6

Animal grouping in Example 5.

| Group | Group | Dose | Ova Challenge |
|---|---|---|---|
| A | Saline Vehicle | 100 μl/animal i.t. | − |
| B | Ova Vehicle | 100 μl/animal i.t. | + |
| C | Fluticasone | 100 μg/animal i.t. | + |
| D | Compound 92 | 500 μg/animal i.t. | + |
| E | Compound 92 | 1000 μg/animal i.t. | + |
| F | Compound 90 | 500 μg/animal i.t. | + |
| G | Compound 90 | 1000 μg/animal i.t. | + |
| H | Compound 73 | 500 μg/animal i.t. | + |

TABLE 6-continued

Animal grouping in Example 5.

| Group | Group | Dose | Ova Challenge |
|---|---|---|---|
| I | Compound 73 | 2000 µg/animal i.t. | + |
| J | Compound 84 | 500 µg/animal i.t. | + |
| K | Compound 84 | 2000 µg/animal i.t. | + |

Test compounds were triturated and volume was made up with Normal Saline (0.9% NaCl). Animals were administered TRPA1 antagonists (Compound 52, Compound 73, Compound 84, Compound 90 and Compound 92) intra-tracheally (i.t.) 1 hour and fluticasone 24 hours and 1 hour before ovalbumin challenge. Animals were sacrificed 48 hours after ovalbumin challenge.

BAL was performed at approximately 48 hours after ovalbumin challenge and the pooled BAL was used to determined total number of cells and for cell differential study (according to Example 2).

The total number of eosinophils in each BAL sample and % inhibition of eosinophils were calculated according to Example 3

The data was statistically evaluated by ANOVA followed by Dunnett's multiple comparisons test.

Figure 6:
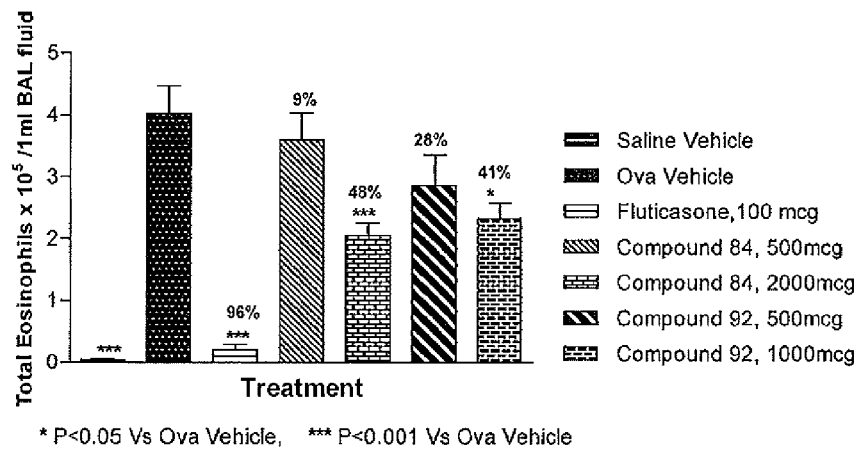
FIG. 6 is a bar graph that represents the effect of Compound 84 and Compound 92 on eosinophil count in BALF.
Figure 7:
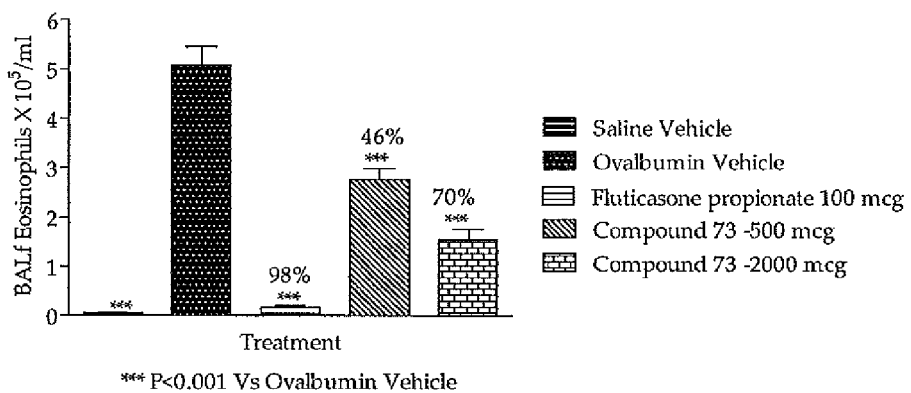
FIG. 7 is a bar graph that represents the effect of Compound 73 on eosinophil count in BALF.
Figure 8:
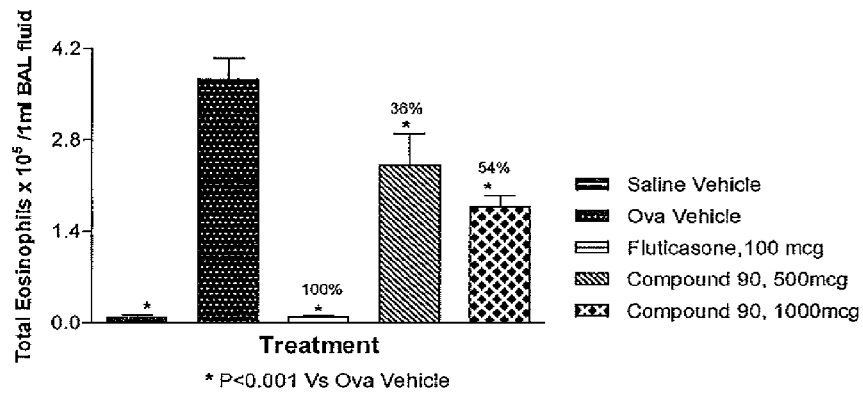
FIG. 8 is a bar graph that represents the effect of Compound 90 on eosinophil count in BALF.

In the ovalbumin challenged-vehicle (Ova Vehicle) treated animals, significant increase in inflammation (eosinophils) was observed compared to saline controls (Saline Vehicle) (FIGS. 6, 7 and 8).

Conclusion

The TRPA1 antagonists (Compound 52, Compound 73, Compound 84, Compound 90 and Compound 92) showed significant inhibition of pulmonary eosinophilia in asthma model in BN rats in a dose dependent manner.

saline (0.9% NaCl). Animals were administered Compound 52 and Compound 90 intra-treacheally 4 hours before LPS aerosolized exposure. Animals were sacrificed 12 hours after aerosolized exposure. The control group of animals received only 2 mg Lactose/100 µl distilled water/animal intratracheally or normal saline 100 µl/animal intratracheally.

TABLE 7

Animal grouping in Example 6

| Group | Group Code | Dose | LPS Exposure |
|---|---|---|---|
| A | PBS Control | 100 µl/animal i.t. | − |
| B | LPS Control | 100 µl/animal i.t. | + |
| C | Compound 52, 1000 µg | 1000 µg/animal i.t. | + |
| D | Compound 90, 2000 µg | 2000 µg/animal i.t. | + |

Broncho alveolar lavage (BAL) was performed at approximately 12 hours after aerosolized exposure. Animals were euthanized with an overdose of urethane, trachea was exposed and BAL was performed 5 times using 2 ml PBS. All aspirates of BAL were pooled and total number of cells determined using a hemocytometer. BALFwas centrifuged. The cell pellet collected after centrifugation was resuspended in 50 µL serum and used for preparation of smears.

For cell differentials, slides were stained with Leishman's stain and a differential cell count of 500 cells based on standard morphology was performed manually.

The total number of neutrophils in each BAL sample was calculated using the formula:

$$\text{Total No. of neutrophils (in } BAL) = \frac{\text{Total cell count} \times 10^5 / \text{mL} \times \text{Percent neutrophils}}{100}$$

Percent inhibition of neutrophils was calculated using the following formula:

$$\% \text{ Inhibition of neutrophils} = \frac{\text{Avg. } neutrophils_{(LPS\ Control)} - neutrophils_{(Treatment)}}{\text{Avg. } neutrophils_{(LPS\ Control)} - \text{Avg. } neutrophils_{(PBS\ Control)}} \times 100$$

Example 6

Efficacy Study of TRPA1 Antagonists in Male Brown Norway Rats

Male Brown Norway rats were exposed to aerosolized Lipopolysaccharide (LPS) (100 µg/ml) for 40 minutes at 1.8 bar pressure using a nebulizer (Hudson Respiratory Care Incorporated), phosphate buffered saline (PBS) control animals were exposed to hyrdroxylamine hydrochloride in PBS.

Rats were randomly assigned to different treatment groups (as shown in table 7). Test compounds were triturated and volume was made up with either distilled water or normal Data was statistically evaluated by ANOVA followed by Dunnett's multiple comparisons test.

Results

Figure 9:
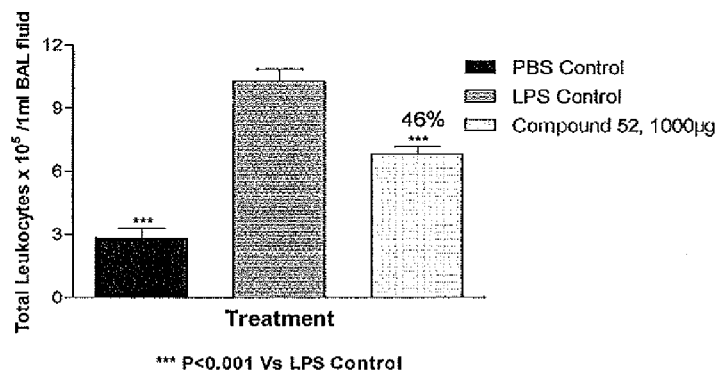
FIG. 9 is a bar graph that represents the effect of compound 52 on total leukocyte count in BALF.
Figure 10:
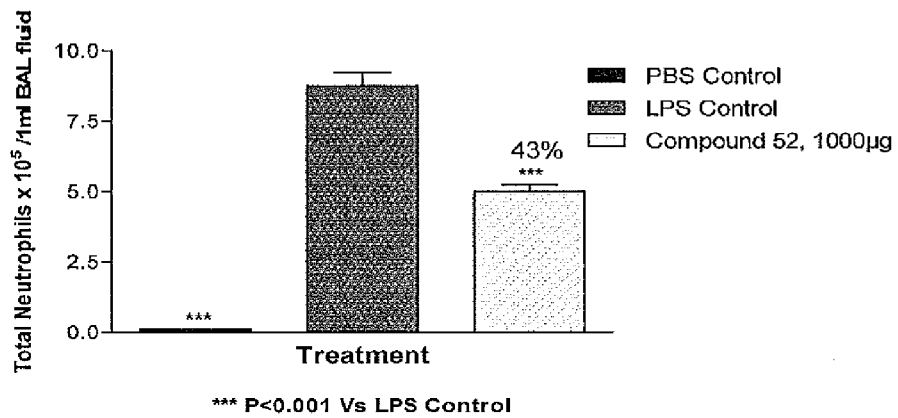
FIG. 10 is a bar graph that represents the effect of compound 52 on neutrophil count in BALF.
Figure 11:
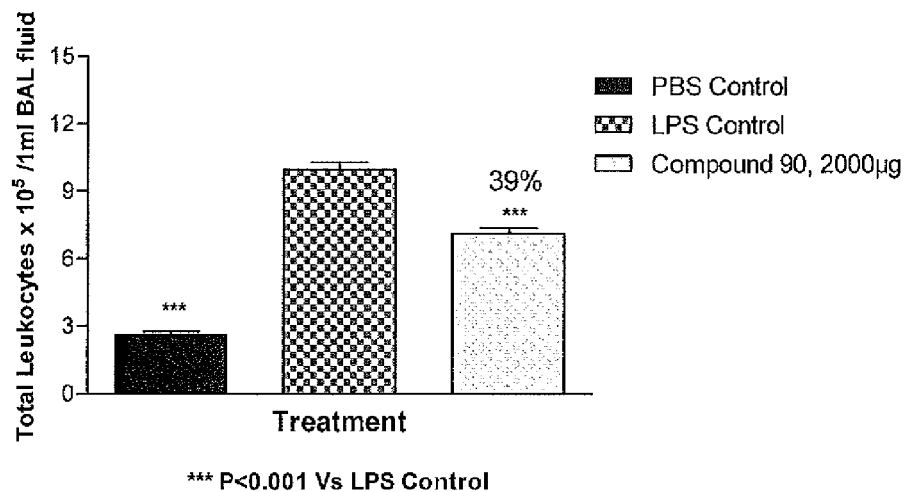
FIG. 11 is a bar graph that represents the effect of compound 90 on total leukocyte count in BALF.
Figure 12:
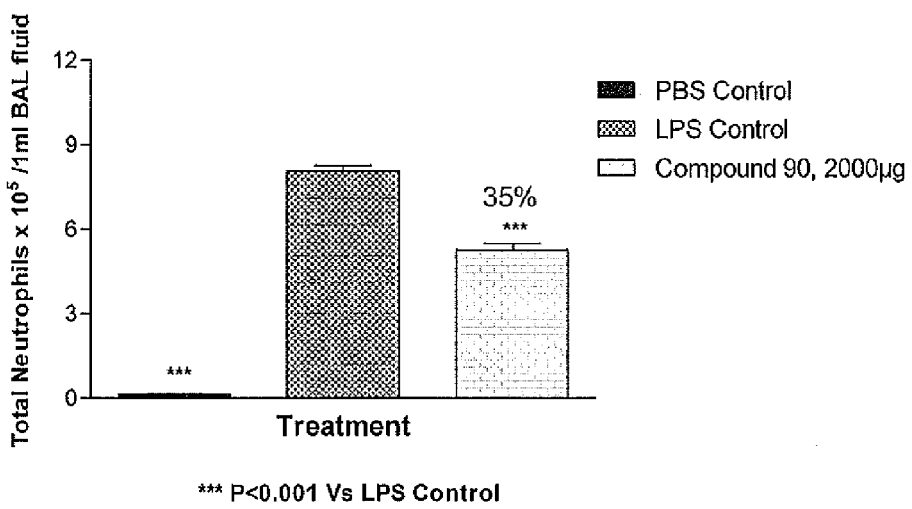
FIG. 12 is a bar graph that represents the effect of compound 90 on neutrophil count in BALF.

In LPS control group, significant increase in inflammation (total cells and neutrophils) was observed compared to PBS control. Compound 52 showed significant inhibition of total leukocytes and neutrophils (FIG. 9 and FIG. 10). Compound 90 also showed significant inhibition of total leukocytes and neutrophils (FIG. 11 and FIG. 12).

Conclusion

Intratracheal administration of Compound 52 and Compound 90 showed significant inhibition of LPS induced leukocyte infiltration and neutrophils in BALF.

Although the invention herein has been described with reference to particular embodiments, it is to be understood that these embodiments are merely illustrative of the principles and application of the present invention. It is therefore to be understood that numerous modifications may be made to the illustrative embodiments.

All publications, patents, and patent applications cited in this application are herein incorporated by reference to the same extent as if each individual publication, patent, or patent application was specifically and individually indicated to be incorporated herein by reference.

We claim:

1. A method of reducing eosinophil or neutrophil count and/or increasing FEV1 in a subject having a respiratory disorder, said method comprising administering to the subject by inhalation route an effective amount of a TRPA1 antagonist of formulae: (XII) or (D)

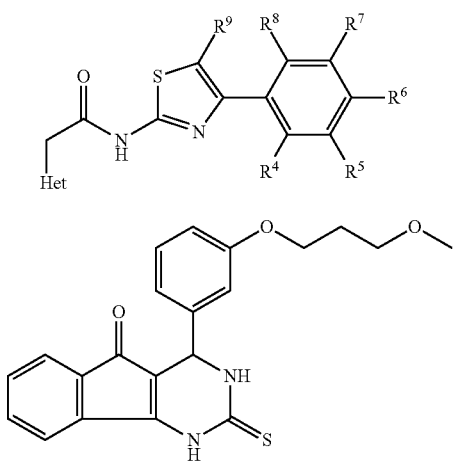

(XII)

(D)

or a pharmaceutically acceptable salt thereof
wherein,
'Het' is selected from the group consisting of

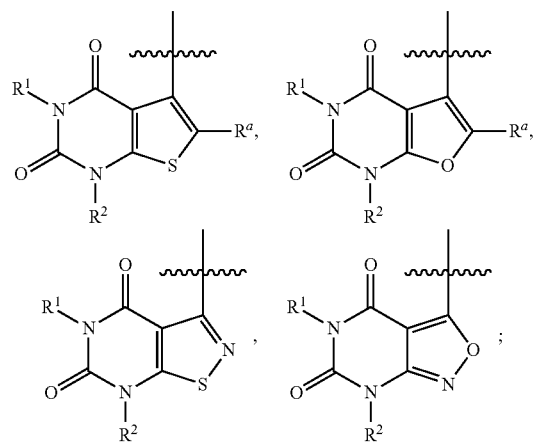

$R^1$, $R^2$ and $R^a$, which may be the same or different, are each independently hydrogen or $(C_1-C_4)$alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

2. The method according to claim 1, wherein the TRPA1 antagonist is

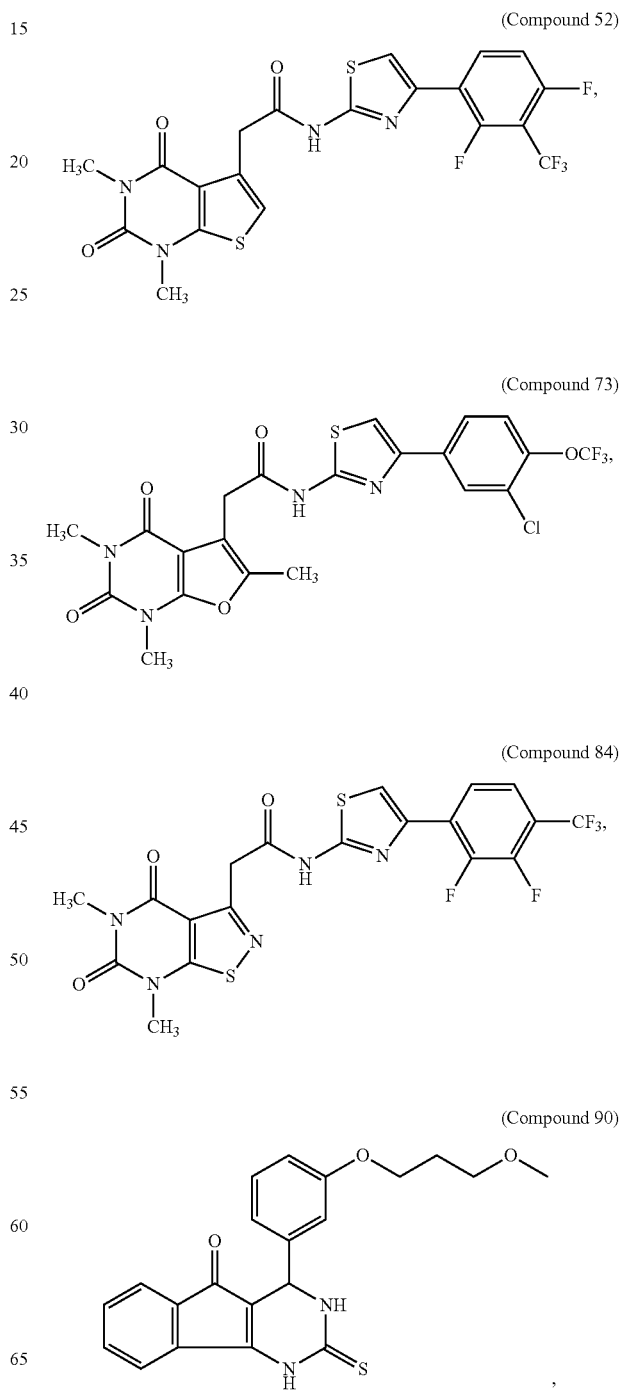

(Compound 52)

(Compound 73)

(Compound 84)

(Compound 90)

-continued

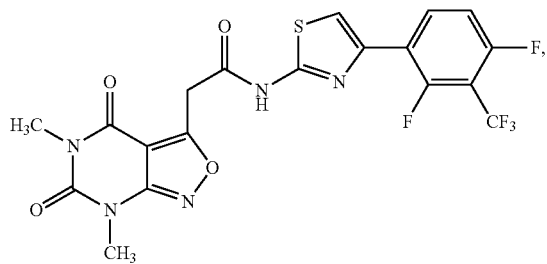
(Compound 92)

or a pharmaceutically acceptable salt thereof.

3. The method according to claim 1, wherein the TRPA1 antagonist has the structure

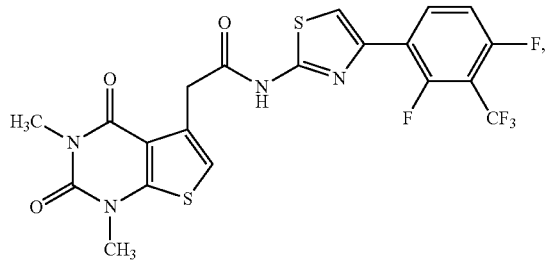
(Compound 52)

or its pharmaceutically acceptable salt, and wherein the effective amount of the TRPA1 antagonist ranges from about 0.1 mcg to about 40 mg.

4. The method according to claim 1, wherein the TRPA1 antagonist has the structure

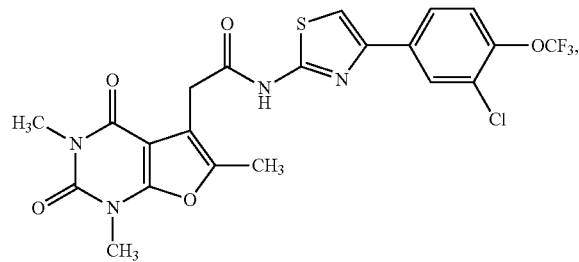
(Compound 73)

or its pharmaceutically acceptable salt, and wherein the effective amount of the TRPA1 antagonist ranges from about 0.1 mcg to about 40 mg.

5. The method according to claim 1, wherein TRPA1 antagonist has the structure

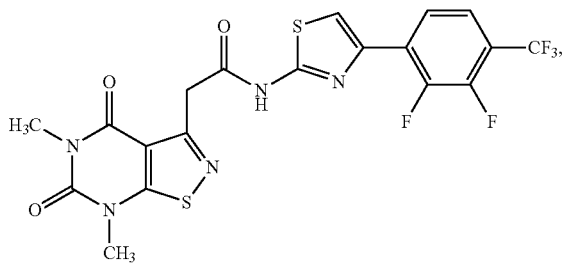
(Compound 84)

or its pharmaceutically acceptable salt, and wherein the effective amount of the TRPA1 antagonist ranges from about 0.1 mcg to about 40 mg.

6. The method according to claim 1, wherein TRPA1 antagonist has the structure

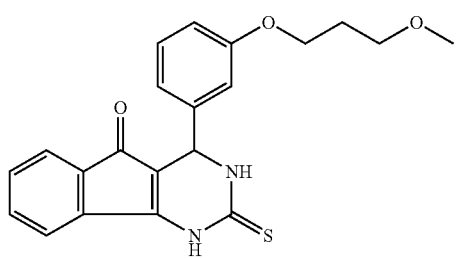
(Compound 90)

or its pharmaceutically acceptable salt, and wherein the effective amount of the TRPA1 antagonist ranges from about 0.1 mcg to about 40 mg.

7. The method according to claim 1, wherein TRPA1 antagonist has the structure

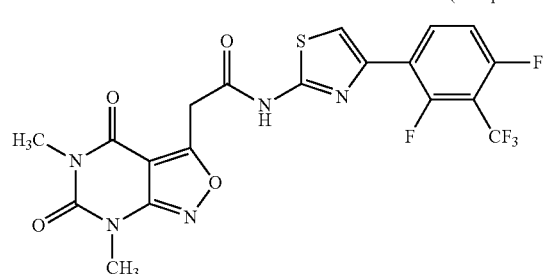
(Compound 92)

or its pharmaceutically acceptable salt, and wherein the effective amount of the TRPA1 antagonist ranges from about 0.1 mcg to about 40 mg.

* * * * *